US007884194B2

(12) United States Patent
Kole et al.

(10) Patent No.: US 7,884,194 B2
(45) Date of Patent: Feb. 8, 2011

(54) SOLUBLE HER2 AND HER3 SPLICE VARIANT PROTEINS, SPLICE-SWITCHING OLIGONUCLEOTIDES, AND THEIR USE IN THE TREATMENT OF DISEASE

(75) Inventors: Ryszard Kole, Corvallis, OR (US); Peter Sazani, Corvallis, OR (US); Jing Wan, Chapel Hill, NC (US)

(73) Assignee: AVI BioPharma Inc., Corvallis, OR (US)

( * ) Notice: Subject to any disclaimer, the term of this patent is extended or adjusted under 35 U.S.C. 154(b) by 0 days.

(21) Appl. No.: 12/157,094

(22) Filed: Jun. 6, 2008

(65) Prior Publication Data

US 2009/0105139 A1 Apr. 23, 2009

Related U.S. Application Data

(60) Provisional application No. 60/956,887, filed on Aug. 20, 2007, provisional application No. 60/942,319, filed on Jun. 6, 2007.

(51) Int. Cl.
C07K 14/485 (2006.01)
C12N 15/11 (2006.01)
(52) U.S. Cl. .................. 530/402; 536/23.5; 530/350
(58) Field of Classification Search ................. None
See application file for complete search history.

(56) References Cited

U.S. PATENT DOCUMENTS

| 4,902,502 | A | * | 2/1990 | Nitecki et al. |
| 5,034,506 | A | | 7/1991 | Summerton et al. |
| 5,142,047 | A | | 8/1992 | Summerton et al. |
| 5,166,315 | A | | 11/1992 | Summerton et al. |
| 5,185,444 | A | | 2/1993 | Summerton et al. |
| 5,217,866 | A | | 6/1993 | Summerton et al. |
| 5,506,337 | A | | 4/1996 | Summerton et al. |
| 5,521,063 | A | | 5/1996 | Summerton et al. |
| 5,698,685 | A | | 12/1997 | Summerton et al. |
| 5,976,879 | A | | 11/1999 | Kole et al. |
| 7,392,823 | B2 | * | 7/2008 | Dong et al. |
| 7,732,157 | B1 | * | 6/2010 | Baron et al. |
| 7,737,253 | B2 | * | 6/2010 | Robins et al. |
| 2003/0228606 | A1 | * | 12/2003 | Tatarewicz et al. |
| 2008/0254031 | A1 | * | 10/2008 | McGowan et al. |
| 2009/0258005 | A1 | * | 10/2009 | Gill et al. |

FOREIGN PATENT DOCUMENTS

| WO | WO 99/14226 A2 | 3/1999 |
| WO | WO 99/14226 A3 | 3/1999 |
| WO | WO 00/56746 A2 | 9/2000 |
| WO | WO 00/56746 A3 | 9/2000 |
| WO | WO 00/56748 A1 | 9/2000 |
| WO | WO 01/25248 A2 | 4/2001 |
| WO | WO 01/25248 A3 | 4/2001 |
| WO | WO 02/28875 A2 | 4/2002 |
| WO | WO 02/28875 A3 | 5/2002 |
| WO | WO 03/006475 A2 | 1/2003 |
| WO | WO 03/095467 A1 | 11/2003 |
| WO | WO 2004007734 A1 | * | 1/2004 |
| WO | WO 03/006475 A3 | 2/2004 |
| WO | WO 2006027693 A2 | * | 3/2006 |

OTHER PUBLICATIONS

Aigner, et al., "Expression of a truncated 100 kDa HER2 splice variant acts as an endogenous inhibitor of tumour cell proliferation",*Oncogene*, 20(17):2101-2111 (2001).
Baselga, J., et al., "Recombinant humanized anti-HER2 antibody (Herceptin) enhances the antitumor activity of paclitaxel and doxorubicin against HER2/neu overexpressing human breast cancer xenografts", Cancer Research 58(13):2825-2831 (1998).
Brodowicz, T., et al., "Soluble HER-2/neu neutralizes biologic effects of anti-HER-2/neu antibody on breast cancer cells in vitro", *Int. J. Cancer*, 73(6):875-879 (1997).
Colomer, R., et al., "Herceptin: from the bench to the clinic", *Cancer Investigation*, 19:49-56 (2001).
Flanagan, W.M., et al., "A cytosine analog that confers enhanced potency to antisense oligonucleotides", *PNAS*, 96:3513-3518 (1999).
Fluiter, K., et al., "In vivo tumor growth inhibition and biodistribution studies of locked nucleic acid (LNA) antisense oligonucleotides", *Nucleic Acids Res.*, 31(3):953-962 (2003).
Geary, R.S., et al., "Pharmacokinetics of a tumor necrosis factor-alpha. phosphorothioate 2'-O-(2-methoxyethyl) modified antisense oligonucleotide: comparison across species", *Drug Metabolism and Disposition*, 31(11):1419-1428 (2003).
Gordon, M.S., et al., "Clinical activity of pertuzumab (rhuMAb 2C4), a HER dimerization inhibitor, in advanced ovarian cancer: potential predictive relationship with tumor HER2 activation status", *J. Clin. Oncol.* 24(26):4324-4332 (2006).
Hengen, P., "Purification of His-Tag fusion proteins from *Escherichia coli*", *Trends Biochem. Sci.*, 20(7):285-86 (1995).
Holmes, S.C., "Steric inhibition of human immunodeficiency virus type-1 Tat-dependent trans-activation in vitro and in cells by oligonucleotides containing 2'-O-methyl G-clamp ribonucleoside analogues", *Nucleic Acids Res.*, 31(11):2759-2768 (2003).
Hynes, N., et al., "The biology of erbB-2/neu/HER-2 and its role in cancer", *Biochem. Biophys. Acta.* 1198(2-3):165-184 (1994).
Jhabvala-Romero, F., et al., "Herstatin inhibits heregulin-mediated breast cancer cell growth and overcomes tamoxifen resistance in breast cancer cells that overexpress HER-2.", *Oncogene*, 22(50):8178-8186 (2003).
Justman, Q., et al., "Herstatin, an autoinhibitor of the human epidermal growth factor receptor 2 tyrosine kinase, modulates epidermal growth factor signaling pathways resulting in growth arrest", *J. Biol. Chem.* 277(23):20618-20624 (2002).
Kute, T., et al., "Development of Herceptin resistance in breast cancer cells", *Cytometry*, Part A 57A:86-93 (2004).

(Continued)

*Primary Examiner*—Lorraine Spector
*Assistant Examiner*—Claire Kaufman
(74) *Attorney, Agent, or Firm*—Seed IP Law Group PLLC

(57) ABSTRACT

Soluble epidermal growth factor receptors 2 and 3 (HER2 and HER3) splice variant proteins with HER2 and HER3 antagonist activity and anti-proliferative properties, as well as the corresponding nucleic acids, are provided for treatment of proliferative diseases, in particular cancer. Also provided are compositions and methods for inducing expression of these splice variants, including splice switching oligonucleotides that modulate splicing of pre-mRNA that codes for these receptors.

4 Claims, 19 Drawing Sheets

OTHER PUBLICATIONS

Marshall, N. B., S. K. Oda, et al. "Arginine-rich cell-penetrating peptides facilitate delivery of antisense oligomers into murine leukocytes and alter pre-mRNA splicing", *J. Immunological Methods*, 325(1-2):114-126 (2007).

Nethery, D.E., et al., "Expression of mutant human epidermal receptor 3 attenuates lung fibrosis and improves survival in mice", *J. Appl. Physiol.*, 99(1):298-307 (2005).

Pegram, M., et al., "The effect of HER-2/neu overexpression on chemotherapeutic drug sensitivity in human breast and ovarian cancer cells", *Oncogene*, 15(5):537-547 (1997).

Sazani, P., et al., "Systemically delivered antisense oligomers upregulate gene expression in mouse tissues", *Nature Biotechnology*, 20(12):1228-1233 (2002).

Slamon, D., et al., "Human breast cancer: correlation of relapse and survival with amplification of the HER-2/neu oncogene", *Science*, 235(4785):177-182 (1987).

Slamon, D., et al., "Studies of the HER-2/neu proto-oncogene in human breast and ovarian cancer", *Science*, 244(4905):707-712 1989.

Slamon, D., et al., "Use of chemotherapy plus a monoclonal antibody against HER2 for metastatic breast cancer that overexpresses HER2", *N. Engl. J. Med.* 344(11):783-792 2001.

Stevenson, J., et al., 1999, "Phase I clinical/pharmacokinetic and pharmacodynamic trial of the c-raf-1 antisense oligonucleotide ISIS 5132 (CGP 69846A)", *J. Clinical Oncology*, 17(7):2227-2236 (1999).

Stix, G., 2006, "A new assault on HIV", *Scientific American*, 294(6):76-79 (2006).

Summerton, J. and D. Weller, "Morpholino antisense oligomers: design, preparation, and properties", *Antisense Nucleic Acid Drug Dev.*, 7(3):187-95 (1997).

Wierzbicka, E., et al., 2006, Brit. J. of Dermatol., 155: 207-229 (2006).

Xu, K.P., 2007, "Cross talk between c-Met and epidermal growth factor receptor during retinal pigment epithelial wound healing", *Investig. Ophthal. and Visual Sci.*, 48(5):2242-2248 (2007).

Yacysyhn, B.R., et al., "Double blind, placebo controlled trial of the remission inducing and steroid sparing properties of an ICAM-1 antisense oligodeoxynucleotide, alicaforsen (ISIS 2302), in active steroid dependent Crohn's disease", *Gut*, 51(1):30-36 (2002).

Yarden, Y.,"Biology of HER2 and its importance in breast cancer", *Oncology*, 61(Suppl 2):1-13 (2001).

* cited by examiner cctgggggtgtcagtgccagccccccacaaatctttctgccccccagg<u>aggctgaccagtgtgt</u>

<u>ggcctgtgccactataaggaccccctctgctgccgctgccagcggtgtgaaacctgac</u>

EXON 15

<u>ctctcctacatgcccatctggaagtttccagatgaggagggcgcatgccagccttgcccatcaact</u>

<u>gcacccactc</u>gtgagtccaacggtctttctgcagaaaggagactttcctttcagggt ...

INTRON 15 ... tcccaagagggtggttcccagaattgttgatgagactgtttctccctgcag

<u>ctgtgtggacctgga</u>tga|caagggctgccccgccgagcagagagccag

Δ15  EXON 16

Figure 11 cttgctgtggagtcctcagatcctctcctccttccttccagtggcagagggcaaagtgtgt
gacccactgtgctcctctggggatgctgggcccaggccctgtcagtgcttgtcctgtcgaaattata

EXON 13 gccgagaggtgtctgtgtgaccactgcaacttctgaatggtacagtagggagccagtcaaggat
gggtgggggtggggccctgcaatgaactgttcaggtgcatacaa[taa]aagtctttagacagctttctg
                                           p85

INTRON 13 catgtgccttggtgggattgaggtaggagacctgtggttgtgagatcggagcatgaaggtcaggacttga
agtgacccccccctccctttattcccactacagggagctcgagaatttgcccatgagccgaatgctt

EXON 14 ctcctgccaccgaatgccaacccatggagggcactgccacatgcaatgctcggtatactagtagcac
caggatctccaaggagacagagagaagggcaatactggagcatctgggaatgatatgctaaggatag
cacagagaggccagataatgctaggcctgcagatagaatctgaatgtctggttggtctttgctgg
gaggtatggaattgacctggatctgattctcctgaccttctctcttccactcagggctctgatactt

INTRON 14 gtgctcaatgtgccattttcgagatgggccccactgtg[tga]gcagctgccccatggagtcctaggtgc
                                        Δ13, Δ14
caaggcccaatctacaagtaccagatgttcagatgaatgtcggccctgccatgagaactgcaccag

EXON 15 gggtcagtgatggataataaggagaggggtcaggtggaaggtaggagca ... INTRON 15

... gagcctctgctgtccaagctctcatttaaggtggtgacttttcctccctaggtg[taa]aggaccagag
                                                                                    Δ15
cttcaagactgtttaggacaaacactggtgctgatcgg

EXON 16

Figure 12

SEQUENCE LISTING

<160> NUMBER OF SEQ ID NOS: 95

<210> SEQ ID NO 1

```
<211> LENGTH: 3768
<212> TYPE: DNA
<213> ORGANISM: Homo sapiens

<400> SEQUENCE: 1
atggagctgg cggccttgtg ccgctggggg ctcctcctcg ccctcttgcc ccccggagcc      60
gcgagcaccc aagtgtgcac cggcacagac atgaagctgc ggctccctgc cagtcccgag     120
acccacctgg acatgctccg ccacctctac cagggctgcc aggtggtgca gggaaacctg     180
gaactcacct acctgcccac caatgccagc ctgtccttcc tgcaggatat ccaggaggtg     240
cagggctacg tgctcatcgc tcacaaccaa gtgaggcagg tcccactgca gaggctgcgg     300
attgtgcgag cacccagct ctttgaggac aactatgccc tggccgtgct agacaatgga     360
gacccgctga caataccac ccctgtcaca ggggcctccc caggaggcct gcgggagctg     420
cagcttcgaa gcctcacaga gatcttgaaa ggaggggtct tgatccagcg gaacccccag     480
ctctgctacc aggacacgat tttgtggaag gacatcttcc acaagaacaa ccagctggct     540
ctcacactga tagacaccaa ccgctctcgg gcctgccacc cctgttctcc gatgtgtaag     600
ggctcccgct gctgggggaga gagttctgag gattgtcaga gcctgacgcg cactgtctgt     660
gccggtggct gtgcccgctg caaggggcca ctgcccactg actgctgcca tgagcagtgt     720
gctgccggct gcacgggccc caagcactct gactgcctgg cctgcctcca cttcaaccac     780
agtggcatct gtgagctgca ctgcccagcc ctggtcacct acaacacaga cacgtttgag     840
tccatgccca tcccgagg ccggtataca ttcggcgcca gctgtgtgac tgcctgtccc     900
tacaactacc tttctacgga cgtgggatcc tgcacccctcg tctgccccct gcacaaccaa     960
gaggtgacag cagaggatgg aacacagcgg tgtgagaagt gcagcaagcc ctgtgcccga    1020
gtgtgctatg gtctgggcat ggagcacttg cgagaggtga gggcagttac cagtgccaat    1080
atccaggagt ttgctggctg caagaagatc tttgggagcc tggcatttct gccggagagc    1140
tttgatgggg acccagcctc caacactgcc ccgctccagc cagagcagct ccaagtgttt    1200
gagactctgg aagagatcac aggttaccta tacatctcag catggccgga cagcctgcct    1260
gacctcagcg tcttccagaa cctgcaagta atccggggac gaattctgca caatggcgcc    1320
tactcgctga cctgcaagg gctgggcatc agctggctgg gctgcgctc actgagggaa    1380 ctgggcagtg gactggccct catccaccat aacacccacc tctgcttcgt gcacacggtg    1440
ccctgggacc agctctttcg gaacccgcac caagctctgc tccacactgc caaccggcca    1500
gaggacgagt gtgtgggcga gggcctggcc tgccaccagc tgtgcgcccg agggcactgc    1560
tggggtccag ggcccaccca gtgtgtcaac tgcagccagt ccttcggggg ccaggagtgc    1620
gtggaggaat gccgagtact gcaggggctc ccagggagt atgtgaatgc caggcactgt    1680
ttgccgtgcc accctgagtg tcagccccag aatggctcag tgacctgttt tggaccggag    1740
gctgaccagt gtgtggcctg tgcccactat aaggaccctc ccttctgcgt ggcccgctgc    1800
cccagcggtg tgaaacctga cctctcctac atgcccatct ggaagtttcc agatgaggag    1860
ggcgcatgcc agccttgccc catcaactgc acccactcct gtgtggacct ggatgacaag    1920
ggctgccccg ccgagcagag agccagccct ctgacgtcca tcatctctgc ggtggttggc    1980
attctgctgg tcgtggtctt gggggtggtc tttgggatcc tcatcaagcg acggcagcag    2040
aagatccgga agtacacgat gcggagactg ctgcaggaaa cggagctggt ggagccgctg    2100
acacctagcg gagcgatgcc caaccaggcg cagatgcgga tcctgaaaga gacggagctg    2160
aggaaggtga aggtgcttgg atctggcgct tttggcacag tctacaaggg catctggatc    2220
```

```
cctgatgggg agaatgtgaa aattccagtg gccatcaaag tgttgaggga aaacacatcc    2280
cccaaagcca acaaagaaat cttagacgaa gcatacgtga tggctggtgt gggctcccca    2340
tatgtctccc gccttctggg catctgcctg acatccacgg tgcagctggt gacacagctt    2400
atgccctatg ctgcctctt agaccatgtc cgggaaaacc gcggacgcct gggctcccag    2460
gacctgctga actggtgtat gcagattgcc aaggggatga gctacctgga ggatgtgcgg    2520
ctcgtacaca gggacttggc cgctcggaac gtgctggtca agagtcccaa ccatgtcaaa    2580
attacagact tcgggctggc tcggctgctg acattgacg agacagagta ccatgcagat    2640
gggggcaagg tgcccatcaa gtggatggcg ctggagtcca ttctccgccg gcggttcacc    2700
caccagagtg atgtgtggag ttatggtgtg actgtgtggg agctgatgac ttttggggcc    2760
aaaccttacg atgggatccc agcccggag atccctgacc tgctggaaaa ggggagcgg    2820 ctgccccagc cccccatctg caccattgat gtctacatga tcatggtcaa atgttggatg    2880
attgactctg aatgtcggcc aagattccgg gagttggtgt ctgaattctc ccgcatggcc    2940 agggacccc agcgctttgt ggtcatccag aatgaggact tgggcccagc cagtcccttg    3000
gacagcacct tctaccgctc actgctggag gacgatgaca tggggggacct ggtgatgct    3060 gaggagtatc tggtacccca gcagggcttc ttctgtccag accctgcccc gggcgctggg    3120
ggcatggtcc accacaggca ccgcagctca tctaccagga gtggcggtgg ggacctgaca    3180
ctagggctgg agccctctga agaggaggcc cccaggtctc cactggcacc ctccgaaggg    3240
gctggctccg atgtatttga tggtgacctg ggaatggggg cagccaaggg gctgcaaagc    3300
ctccccacac atgaccccag ccctctacag cggtacagtg aggaccccac agtacccctg    3360
ccctctgaga ctgatggcta cgttgccccc ctgacctgca gcccccagcc tgaatatgtg    3420
aaccagccag atgttcggcc ccagcccct tcgccccgag agggccctct gcctgctgcc    3480
cgacctgctg gtgccactct ggaaaggcc aagactctct ccccagggaa gaatggggtc    3540
gtcaaagacg ttttgccttt tgggggtgcc gtggagaacc ccgagtactt gacaccccag    3600
ggaggagctg ccctcagcc ccaccctcct cctgccttca gcccagcctt cgacaacctc    3660
tattactggg accaggaccc accagagcgg ggggctccac ccagcacctt caaagggaca    3720
cctacggcag agaacccaga gtacctgggt ctggacgtgc cagtgtga                3768
```

<210> SEQ ID NO 2
<211> LENGTH: 1255
<212> TYPE: PRT
<213> ORGANISM: Homo sapiens

<400> SEQUENCE: 2

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

```
Ala Leu Ala Val Leu Asp Asn Gly Asp Pro Leu Asn Asn Thr Thr Pro
            115                 120                 125
Val Thr Gly Ala Ser Pro Gly Gly Leu Arg Glu Leu Gln Leu Arg Ser
        130                 135                 140
Leu Thr Glu Ile Leu Lys Gly Gly Val Leu Ile Gln Arg Asn Pro Gln
145                 150                 155                 160
Leu Cys Tyr Gln Asp Thr Ile Leu Trp Lys Asp Ile Phe His Lys Asn
            165                 170                 175
Asn Gln Leu Ala Leu Thr Leu Ile Asp Thr Asn Arg Ser Arg Ala Cys
            180                 185                 190
His Pro Cys Ser Pro Met Cys Lys Gly Ser Arg Cys Trp Gly Glu Ser
            195                 200                 205
Ser Glu Asp Cys Gln Ser Leu Thr Arg Thr Val Cys Ala Gly Gly Cys
            210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
            245                 250                 255
His Phe Asn His Ser Gly Ile Cys Glu Leu His Cys Pro Ala Leu Val
            260                 265                 270
Thr Tyr Asn Thr Asp Thr Phe Glu Ser Met Pro Asn Pro Glu Gly Arg
            275                 280                 285
Tyr Thr Phe Gly Ala Ser Cys Val Thr Ala Cys Pro Tyr Asn Tyr Leu
            290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
            325                 330                 335
Pro Cys Ala Arg Val Cys Tyr Gly Leu Gly Met Glu His Leu Arg Glu
            340                 345                 350
Val Arg Ala Val Thr Ser Ala Asn Ile Gln Glu Phe Ala Gly Cys Lys
            355                 360                 365
Lys Ile Phe Gly Ser Leu Ala Phe Leu Pro Glu Ser Phe Asp Gly Asp
            370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
            405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
            435                 440                 445
Gly Ile Ser Trp Leu Gly Leu Arg Ser Leu Arg Glu Leu Gly Ser Gly
            450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
            485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
            515                 520                 525
Val Asn Cys Ser Gln Phe Leu Arg Gly Gln Glu Cys Val Glu Glu Cys
```

```
                    530                 535                 540
Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                    565                 570                 575

Phe Gly Pro Glu Ala Asp Gln Cys Val Ala Cys Ala His Tyr Lys Asp
                    580                 585                 590

Pro Pro Phe Cys Val Ala Arg Cys Pro Ser Gly Val Lys Pro Asp Leu
                    595                 600                 605

Ser Tyr Met Pro Ile Trp Lys Phe Pro Asp Glu Glu Gly Ala Cys Gln
610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                    645                 650                 655

Ala Val Val Gly Ile Leu Leu Val Val Val Leu Gly Val Val Phe Gly
                    660                 665                 670

Ile Leu Ile Lys Arg Arg Gln Gln Lys Ile Arg Lys Tyr Thr Met Arg
                    675                 680                 685

Arg Leu Leu Gln Glu Thr Glu Leu Val Glu Pro Leu Thr Pro Ser Gly
690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                    725                 730                 735

Gly Ile Trp Ile Pro Asp Gly Glu Asn Val Lys Ile Pro Val Ala Ile
                    740                 745                 750

Lys Val Leu Arg Glu Asn Thr Ser Pro Lys Ala Asn Lys Glu Ile Leu
                    755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                    805                 810                 815

Leu Gly Ser Gln Asp Leu Leu Asn Trp Cys Met Gln Ile Ala Lys Gly
                    820                 825                 830

Met Ser Tyr Leu Glu Asp Val Arg Leu Val His Arg Asp Leu Ala Ala
                    835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                    885                 890                 895

Arg Arg Phe Thr His Gln Ser Asp Val Trp Ser Tyr Gly Val Thr Val
                    900                 905                 910

Trp Glu Leu Met Thr Phe Gly Ala Lys Pro Tyr Asp Gly Ile Pro Ala
                    915                 920                 925

Arg Glu Ile Pro Asp Leu Leu Glu Lys Gly Glu Arg Leu Pro Gln Pro
                    930                 935                 940

Pro Ile Cys Thr Ile Asp Val Tyr Met Ile Met Val Lys Cys Trp Met
945                 950                 955                 960
```

```
Ile Asp Ser Glu Cys Arg Pro Arg Phe Arg Glu Leu Val Ser Glu Phe
            965                 970                 975
Ser Arg Met Ala Arg Asp Pro Gln Arg Phe Val Val Ile Gln Asn Glu
            980                 985                 990
Asp Leu Gly Pro Ala Ser Pro Leu Asp Ser Thr Phe Tyr Arg Ser Leu
            995                1000                1005
Leu Glu Asp Asp Asp Met Gly Asp Leu Val Asp Ala Glu Glu Tyr Leu
           1010                1015                1020
Val Pro Gln Gln Gly Phe Phe Cys Pro Asp Pro Ala Pro Gly Ala Gly
1025                1030                1035                1040
Gly Met Val His His Arg His Arg Ser Ser Ser Thr Arg Ser Gly Gly
           1045                1050                1055
Gly Asp Leu Thr Leu Gly Leu Glu Pro Ser Glu Glu Glu Ala Pro Arg
           1060                1065                1070
Ser Pro Leu Ala Pro Ser Glu Gly Ala Gly Ser Asp Val Phe Asp Gly
           1075                1080                1085
Asp Leu Gly Met Gly Ala Ala Lys Gly Leu Gln Ser Leu Pro Thr His
           1090                1095                1100
Asp Pro Ser Pro Leu Gln Arg Tyr Ser Glu Asp Pro Thr Val Pro Leu
1105                1110                1115                1120
Pro Ser Glu Thr Asp Gly Tyr Val Ala Pro Leu Thr Cys Ser Pro Gln
           1125                1130                1135
Pro Glu Tyr Val Asn Gln Pro Asp Val Arg Pro Gln Pro Pro Ser Pro
           1140                1145                1150
Arg Glu Gly Pro Leu Pro Ala Ala Arg Pro Ala Gly Ala Thr Leu Glu
           1155                1160                1165
Arg Pro Lys Thr Leu Ser Pro Gly Lys Asn Gly Val Val Lys Asp Val
           1170                1175                1180
Phe Ala Phe Gly Gly Ala Val Glu Asn Pro Glu Tyr Leu Thr Pro Gln
1185                1190                1195                1200
Gly Gly Ala Ala Pro Gln Pro His Pro Pro Ala Phe Ser Pro Ala
           1205                1210                1215
Phe Asp Asn Leu Tyr Tyr Trp Asp Gln Asp Pro Pro Glu Arg Gly Ala
           1220                1225                1230
Pro Pro Ser Thr Phe Lys Gly Thr Pro Thr Ala Glu Asn Pro Glu Tyr
           1235                1240                1245
Leu Gly Leu Asp Val Pro Val
           1250                1255

<210> SEQ ID NO 3
<211> LENGTH: 4029
<212> TYPE: DNA
<213> ORGANISM: Homo sapiens

<400> SEQUENCE: 3
atgagggcga acgacgctct gcaggtgctg ggcttgcttt tcagcctggc ccggggctcc      60
gaggtgggca actctcaggc agtgtgtcct gggactctga atggcctgag tgtgaccggc     120
gatgctgaga accaatacca gacactgtac aagctctacg agaggtgtga ggtggtgatg     180
gggaaccttg agattgtgct cacgggcaca aatgccgacc tctccttcct gcagtggatt     240
cgagaagtga caggctatgt cctcgtggcc atgaatgaat ctctactctc caccattgcc     300
aacctccgcg tggtgcgagg gacccaggtc tacgatggga gtttgccat cttcgtcatg     360 ttgaactata caccaactc cagccacgct ctgcgccagc tccgcttgac tcagctcacc     420
gagattctgt caggggggtgt ttatattgag aagaacgata agctttgtca catggacaca     480
```

| | |
|---|---|
| attgactgga gggacatcgt gagggaccga gatgctgaga tagtggtgaa ggacaatggc | 540 |
| agaagctgtc cccctgtca tgaggtttgc aaggggcgat gctgggtcc tggatcagaa | 600 |
| gactgccaga cattgaccaa gaccatctgt gctcctcagt gtaatggtca ctgctttggg | 660 |
| cccaacccca accagtgctg ccatgatgag tgtgccgggg gctgctcagg ccctcaggac | 720 |
| acagactgct ttgcctgccg gcacttcaat gacagtggag cctgtgtacc tcgctgtcca | 780 |
| cagcctcttg tctacaacaa gctaactttc cagctggaac ccaatcccca caccaagtat | 840 |
| cagtatggag gagtttgtgt agccagctgt ccccataact ttgtggtgga tcaaacatcc | 900 |
| tgtgtcaggg cctgtcctcc tgacaagatg gaagtagata aaaatgggct caagatgtgt | 960 |
| gagccttgtg ggggactatg tcccaaagcc tgtgagggaa caggctctgg gagccgcttc | 1020 |
| cagactgtgg actcgagcaa cattgatgga tttgtgaact gcaccaagat cctgggcaac | 1080 |
| ctggactttc tgatcaccgg cctcaatgga gaccctggc acaagatccc tgccctggac | 1140 |
| ccagagaagc tcaatgtctt ccggacagta cgggagatca caggttacct gaacatccag | 1200 |
| tcctggccgc cccacatgca caacttcagt gttttttcca atttgacaac cattggaggc | 1260 |
| agaagcctct acaaccgggg cttctcattg ttgatcatga agaacttgaa tgtcacatct | 1320 |
| ctgggcttcc gatccctgaa ggaaattagt gctgggcgta tctatataag tgccaatagg | 1380 |
| cagctctgct accaccactc tttgaactgg accaaggtgc ttcgggggcc tacgaagag | 1440 |
| cgactagaca tcaagcataa tcggccgcgc agagactgcg tggcagaggg caaagtgtgt | 1500 |
| gacccactgt gctcctctgg gggatgctgg ggcccaggcc ctggtcagtg cttgtcctgt | 1560 |
| cgaaattata gccgaggagg tgtctgtgtg acccactgca actttctgaa tggggagcct | 1620 |
| cgagaatttg cccatgaggc cgaatgcttc tcctgccacc cggaatgcca acccatggag | 1680 |
| ggcactgcca catgcaatgg ctcgggctct gatacttgtg ctcaatgtgc ccattttcga | 1740 |
| gatgggcccc actgtgtgag cagctgcccc catggagtcc taggtgccaa gggcccaatc | 1800 |
| tacaagtacc cagatgttca gaatgaatgt cggccctgcc atgagaactg cacccagggg | 1860 |
| tgtaaaggac cagagcttca agactgttta ggacaaacac tggtgctgat cggcaaaacc | 1920 |
| catctgacaa tggctttgac agtgatagca ggattggtag tgattttcat gatgctgggc | 1980 |
| ggcacttttc tctactggcg tgggcgccgg attcagaata aagggctat gaggcgatac | 2040 |
| ttggaacggg gtgagagcat agagcctctg gaccccagtg agaaggctaa caaagtcttg | 2100 |
| gccagaatct tcaaagagac agagctaagg aagcttaaag tgcttggctc gggtgtctt | 2160 |
| ggaactgtgc acaaaggagt gtggatccct gagggtgaat caatcaagat tccagtctgc | 2220 |
| attaaagtca ttgaggacaa gagtggacgg cagagttttc aagctgtgac agatcatatg | 2280 |
| ctggccattg gcagcctgga ccatgcccac attgtaaggc tgctgggact atgcccaggg | 2340 |
| tcatctctgc agcttgtcac tcaatatttg cctctgggtt ctctgctgga tcatgtgaga | 2400 |
| caacaccggg gggcactggg gccacagctg ctgctcaact ggggagtaca aattgccaag | 2460 |
| ggaatgtact accttgagga acatggtatg gtgcatagaa acctggctgc ccgaaacgtg | 2520 |
| ctactcaagt cacccagtca ggttcaggtg gcagattttg gtgtggctga cctgctgcct | 2580 |
| cctgatgata gcagctgct atacagtgag gccaagactc caattaagtg gatggccctt | 2640 |
| gagagtatcc actttgggaa atacacacac cagagtgatg tctggagcta tggtgtgaca | 2700 |
| gtttgggagt tgatgacctt cggggcagag ccctatgcag ggctacgatt ggctgaagta | 2760 |
| ccagacctgc tagagaaggg ggagcggttg gcacagcccc agatctgcac aattgatgtc | 2820 |
| tacatggtga tggtcaagtg ttggatgatt gatgagaaca ttcgcccaac cttttaaagaa | 2880 |

```
ctagccaatg agttcaccag gatggcccga gacccaccac ggtatctggt cataaagaga    2940
gagagtgggc ctggaatagc ccctgggcca gagccccatg gtctgacaaa caagaagcta    3000
gaggaagtag agctggagcc agaactagac ctagacctag acttggaagc agaggaggac    3060
aacctggcaa ccaccacact gggctccgcc ctcagcctac cagttggaac acttaatcgg    3120
ccacgtggga gccagagcct tttaagtcca tcatctggat acatgccat gaaccagggt     3180 aatcttgggg agtcttgcca ggagtctgca gtttctggga gcagtgaacg gtgccccgt     3240 ccagtctctc tacacccaat gccacgggga tgcctggcat cagagtcatc agaggggcat    3300
gtaacaggct ctgaggctga gctccaggag aaagtgtcaa tgtgtaggag ccggagcagg    3360
agccggagcc cacggccacg cggagatagc gcctaccatt cccagcgcca cagtctgctg    3420
actcctgtta ccccactctc cccacccggg ttagaggaag aggatgtcaa cggttatgtc    3480
atgccagata cacacctcaa aggtactccc tcctcccggg aaggcaccct ttcttcagtg    3540
ggtctcagtt ctgtcctggg tactgaagaa gaagatgaag atgaggagta tgaatacatg    3600
aaccggagga gaaggcacag tccacctcat cccctaggc caagttccct tgaggagctg     3660
ggttatgagt acatggatgt ggggtcagac ctcagtgcct ctctgggcag cacacagagt    3720
tgcccactcc accctgtacc catcatgccc actgcaggca caactccaga tgaagactat    3780
gaatatatga atcggcaacg agatggaggt ggtcctgggg gtgattatgc agccatgggg    3840
gcctgcccag catctgagca agggtatgaa gagatgagag cttttcaggg gcctggacat    3900
caggcccccc atgtccatta tgcccgccta aaaactctac gtagcttaga ggctacagac    3960
tctgcctttg ataaccctga ttactggcat agcaggcttt tccccaaggc taatgcccag    4020
agaacgtaa                                                           4029
```

<210> SEQ ID NO 4
<211> LENGTH: 1342
<212> TYPE: PRT
<213> ORGANISM: Homo sapiens

<400> SEQUENCE: 4

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val

```
                         165                 170                 175
Lys Asp Asn Gly Arg Ser Cys Pro Pro Cys His Glu Val Cys Lys Gly
                180                 185                 190

Arg Cys Trp Gly Pro Gly Ser Glu Asp Cys Gln Thr Leu Thr Lys Thr
            195                 200                 205

Ile Cys Ala Pro Gln Cys Asn Gly His Cys Phe Gly Pro Asn Pro Asn
        210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
        290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
        355                 360                 365

Asn Gly Asp Pro Trp His Lys Ile Pro Ala Leu Asp Pro Glu Lys Leu
370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
        435                 440                 445

Ile Ser Ala Gly Arg Ile Tyr Ile Ser Ala Asn Arg Gln Leu Cys Tyr
        450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
        515                 520                 525

Cys Val Thr His Cys Asn Phe Leu Asn Gly Glu Pro Arg Glu Phe Ala
        530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
                565                 570                 575

Ala His Phe Arg Asp Gly Pro His Cys Val Ser Ser Cys Pro His Gly
            580                 585                 590
```

```
Val Leu Gly Ala Lys Gly Pro Ile Tyr Lys Tyr Pro Asp Val Gln Asn
        595                 600                 605

Glu Cys Arg Pro Cys His Glu Asn Cys Thr Gln Gly Cys Lys Gly Pro
    610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
            645                 650                 655

Met Met Leu Gly Gly Thr Phe Leu Tyr Trp Arg Gly Arg Arg Ile Gln
        660                 665                 670

Asn Lys Arg Ala Met Arg Arg Tyr Leu Glu Arg Gly Glu Ser Ile Glu
        675                 680                 685

Pro Leu Asp Pro Ser Glu Lys Ala Asn Lys Val Leu Ala Arg Ile Phe
690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
            725                 730                 735

Ile Pro Val Cys Ile Lys Val Ile Glu Asp Lys Ser Gly Arg Gln Ser
        740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
    770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
            805                 810                 815

Gln Ile Ala Lys Gly Met Tyr Tyr Leu Glu Glu His Gly Met Val His
        820                 825                 830

Arg Asn Leu Ala Ala Arg Asn Val Leu Leu Lys Ser Pro Ser Gln Val
    835                 840                 845

Gln Val Ala Asp Phe Gly Val Ala Asp Leu Leu Pro Pro Asp Asp Lys
850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
            885                 890                 895

Tyr Gly Val Thr Val Trp Glu Leu Met Thr Phe Gly Ala Glu Pro Tyr
        900                 905                 910

Ala Gly Leu Arg Leu Ala Glu Val Pro Asp Leu Leu Glu Lys Gly Glu
        915                 920                 925

Arg Leu Ala Gln Pro Gln Ile Cys Thr Ile Asp Val Tyr Met Val Met
    930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
            965                 970                 975

Val Ile Lys Arg Glu Ser Gly Pro Gly Ile Ala Pro Gly Pro Glu Pro
        980                 985                 990

His Gly Leu Thr Asn Lys Lys Leu Glu Glu Val Glu Leu Glu Pro Glu
        995                 1000                1005

Leu Asp Leu Asp Leu Asp Leu Glu Ala Glu Glu Asp Asn Leu Ala Thr
    1010                1015                1020
```

-continued

Thr Thr Leu Gly Ser Ala Leu Ser Leu Pro Val Gly Thr Leu Asn Arg
1025                1030                1035                1040

Pro Arg Gly Ser Gln Ser Leu Leu Ser Pro Ser Ser Gly Tyr Met Pro
            1045                1050                1055

Met Asn Gln Gly Asn Leu Gly Glu Ser Cys Gln Glu Ser Ala Val Ser
        1060                1065                1070

Gly Ser Ser Glu Arg Cys Pro Arg Pro Val Ser Leu His Pro Met Pro
    1075                1080                1085

Arg Gly Cys Leu Ala Ser Glu Ser Ser Glu Gly His Val Thr Gly Ser
1090                1095                1100

Glu Ala Glu Leu Gln Glu Lys Val Ser Met Cys Arg Ser Arg Ser Arg
1105                1110                1115                1120

Ser Arg Ser Pro Arg Pro Arg Gly Asp Ser Ala Tyr His Ser Gln Arg
            1125                1130                1135

His Ser Leu Leu Thr Pro Val Thr Pro Leu Ser Pro Pro Gly Leu Glu
        1140                1145                1150

Glu Glu Asp Val Asn Gly Tyr Val Met Pro Asp Thr His Leu Lys Gly
    1155                1160                1165

Thr Pro Ser Ser Arg Glu Gly Thr Leu Ser Ser Val Gly Leu Ser Ser
1170                1175                1180

Val Leu Gly Thr Glu Glu Glu Asp Glu Asp Glu Glu Tyr Glu Tyr Met
1185                1190                1195                1200

Asn Arg Arg Arg Arg His Ser Pro Pro His Pro Pro Arg Pro Ser Ser
            1205                1210                1215

Leu Glu Glu Leu Gly Tyr Glu Tyr Met Asp Val Gly Ser Asp Leu Ser
        1220                1225                1230

Ala Ser Leu Gly Ser Thr Gln Ser Cys Pro Leu His Pro Val Pro Ile
    1235                1240                1245

Met Pro Thr Ala Gly Thr Thr Pro Asp Glu Asp Tyr Glu Tyr Met Asn
1250                1255                1260

Arg Gln Arg Asp Gly Gly Gly Pro Gly Gly Asp Tyr Ala Ala Met Gly
1265                1270                1275                1280

Ala Cys Pro Ala Ser Glu Gln Gly Tyr Glu Glu Met Arg Ala Phe Gln
            1285                1290                1295

Gly Pro Gly His Gln Ala Pro His Val His Tyr Ala Arg Leu Lys Thr
        1300                1305                1310

Leu Arg Ser Leu Glu Ala Thr Asp Ser Ala Phe Asp Asn Pro Asp Tyr
    1315                1320                1325

Trp His Ser Arg Leu Phe Pro Lys Ala Asn Ala Gln Arg Thr
1330                1335                1340

<210> SEQ ID NO 5
<211> LENGTH: 1755
<212> TYPE: DNA
<213> ORGANISM: Homo sapiens

<400> SEQUENCE: 5
atggagctgg cggccttgtg ccgctggggg ctcctcctcg ccctcttgcc ccccggagcc     60
gcgagcaccc aagtgtgcac cggcacagac atgaagctgc ggctccctgc cagtcccgag    120
acccaccctg acatgctccg ccacctctac cagggctgcc aggtggtgca gggaaacctg    180
gaactcacct acctgcccac caatgccagc ctgtccttcc tgcaggatat ccaggaggtg    240
cagggctacg tgctcatcgc tcacaaccaa gtgaggcagg tcccactgca gaggctgcgg    300
attgtgcgag gcacccagct ctttgaggac aactatgccc tggccgtgct agacaatgga    360

-continued

```
gacccgctga acaataccac ccctgtcaca ggggcctccc caggaggcct gcgggagctg    420
cagcttcgaa gcctcacaga gatcttgaaa ggaggggtct tgatccagcg gaaccccag    480 ctctgctacc aggacacgat tttgtggaag acatcttcc acaagaacaa ccagctggct    540
ctcacactga tagacaccaa ccgctctcgg gcctgccacc cctgttctcc gatgtgtaag    600
ggctcccgct gctggggaga gagttctgag gattgtcaga gcctgacgcg cactgtctgt    660
gccggtggct gtgcccgctg caaggggcca ctgcccactg actgctgcca tgagcagtgt    720
gctgccggct gcacgggccc caagcactct gactgcctgg cctgcctcca cttcaaccac    780
agtggcatct gtgagctgca ctgcccagcc ctggtcacct acaacacaga cacgtttgag    840
tccatgccca atcccgaggg ccggtataca ttcggcgcca gctgtgtgac tgcctgtccc    900
tacaactacc tttctacgga cgtgggatcc tgcaccctcg tctgccccct gcacaaccaa    960
gaggtgacag cagaggatgg aacacagcgg tgtgagaagt gcagcaagcc ctgtgcccga    1020
gtgtgctatg gtctgggcat ggagcacttg cgagaggtga gggcagttac cagtgccaat    1080
atccaggagt ttgctggctg caagaagatc tttgggagcc tggcatttct gccggagagc    1140
tttgatgggg acccagcctc caacactgcc ccgctccagc cagagcagct ccaagtgttt    1200
gagactctgg aagagatcac aggttaccta tacatctcag catggccgga cagcctgcct    1260
gacctcagcg tcttccagaa cctgcaagta atccggggac gaattctgca caatggcgcc    1320
tactcgctga ccctgcaagg gctgggcatc agctggctgg gctgcgctc actgagggaa    1380 ctgggcagtg gactggccct catccaccat aacacccacc tctgcttcgt gcacacggtg    1440
ccctgggacc agctctttcg gaacccgcac caagctctgc tccacactgc caaccggcca    1500
gaggacgagt gtgtgggcga gggcctggcc tgccaccagc tgtgcgcccg agggcactgc    1560
tggggtccag ggcccaccca gtgtgtcaac tgcagccagt tccttcgggg ccaggagtgc    1620
gtggaggaat gccgagtact gcaggggctc cccaggggag atgtgaatgc caggcactgt    1680
ttgccgtgcc accctgagtg tcagccccag aatggctcag tgacctgttt tggaccgctg    1740
tgtggacctg gatga                                                     1755
```

<210> SEQ ID NO 6
<211> LENGTH: 584
<212> TYPE: PRT
<213> ORGANISM: Homo sapiens

<400> SEQUENCE: 6

```
Met Glu Leu Ala Ala Leu Cys Arg Trp Gly Leu Leu Ala Leu Leu
 1               5                  10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125
```

Val Thr Gly Ala Ser Pro Gly Gly Leu Arg Glu Leu Gln Leu Arg Ser
    130                 135                 140

Leu Thr Glu Ile Leu Lys Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys

```
                 545                 550                 555                 560
Leu Pro Cys His Pro Glu Cys Gln Pro Gln Asn Gly Ser Val Thr Cys
                 565                 570                 575

Phe Gly Pro Leu Cys Gly Pro Gly
            580

<210> SEQ ID NO 7
<211> LENGTH: 1626
<212> TYPE: DNA
<213> ORGANISM: Homo sapiens

<400> SEQUENCE: 7
atgagggcga acgacgctct gcaggtgctg ggcttgcttt tcagcctggc ccggggctcc      60
gaggtgggca actctcaggc agtgtgtcct gggactctga atggcctgag tgtgaccggc     120
gatgctgaga accaatacca gacactgtac aagctctacg agaggtgtga ggtggtgatg     180
gggaaccttg agattgtgct cacgggacac aatgccgacc tctccttcct gcagtggatt     240
cgagaagtga caggctatgt cctcgtggcc atgaatgaat tctctactct accattgccc     300
aacctccgcg tggtgcgagg gacccaggtc tacgatggga gtttgccat cttcgtcatg     360
ttgaactata caccaactc cagccacgct ctgcgccagc tccgcttgac tcagctcacc     420
gagattctgt caggggtgt ttatattgag aagaacgata agctttgtca catggacaca     480
attgactgga gggacatcgt gagggaccga gatgctgaga tagtggtgaa ggacaatggc     540
agaagctgtc cccctgtca tgaggtttgc aaggggcgat gctggggtcc tggatcagaa     600
gactgccaga cattgaccaa gaccatctgt gctcctcagt gtaatggtca ctgctttggg     660
cccaacccca accagtgctg ccatgatgag tgtgccgggg gctgctcagg ccctcaggac     720
acagactgct ttgcctgccg gcacttcaat gacagtggag cctgtgtacc tcgctgtcca     780
cagcctcttg tctacaacaa gctaactttc cagctgaac ccaatccca caccaagtat     840
cagtatggag gagtttgtgt agccagctgt ccccataact ttgtggtgga tcaaacatcc     900
tgtgtcaggg cctgtcctcc tgacaagatg gaagtagata aaatgggct caagatgtgt     960
gagccttgtg gggactatg tcccaaagcc tgtgaggaa caggctctgg gagccgcttc    1020
cagactgtgg actcgagcaa cattgatgga tttgtgaact gcaccaagat cctgggcaac    1080
ctggactttc tgatcaccgg cctcaatgga gaccccctggc acaagatccc tgccctggac    1140
ccagagaagc tcaatgtctt ccggacagta cgggagatca caggttacct gaacatccag    1200
tcctggccgc cccacatgca caacttcagt gttttttcca atttgacaac cattggaggc    1260
agaagcctct acaaccgggg cttctcattg ttgatcatga agaacttgaa tgtcacatct    1320
ctgggcttcc gatccctgaa ggaaattagt gctgggcgta tctatataag tgccaatagg    1380
cagctctgct accaccactc tttgaactgg accaaggtgc ttcggggggcc tacggaagag    1440
cgactagaca tcaagcataa tcggccgcgc agagactgcg ggagcctcga gaatttgccc    1500
atgaggccga atgcttctcc tgccacccgg aatgccaacc catggagggc actgccacat    1560
gcaatggctc gggctctgat acttgtgctc aatgtgccca ttttcgagat gggcccccact    1620
gtgtga                                                               1626

<210> SEQ ID NO 8
<211> LENGTH: 541
<212> TYPE: PRT
<213> ORGANISM: Homo sapiens

<400> SEQUENCE: 8
```

```
Met Arg Ala Asn Asp Ala Leu Gln Val Leu Gly Leu Leu Phe Ser Leu
  1               5                  10                  15
Ala Arg Gly Ser Glu Val Gly Asn Ser Gln Ala Val Cys Pro Gly Thr
             20                  25                  30
Leu Asn Gly Leu Ser Val Thr Gly Asp Ala Glu Asn Gln Tyr Gln Thr
             35                  40                  45
Leu Tyr Lys Leu Tyr Glu Arg Cys Glu Val Val Met Gly Asn Leu Glu
         50                  55                  60
Ile Val Leu Thr Gly His Asn Ala Asp Leu Ser Phe Leu Gln Trp Ile
 65                  70                  75                  80
Arg Glu Val Thr Gly Tyr Val Leu Val Ala Met Asn Glu Phe Ser Thr
                 85                  90                  95
Leu Pro Leu Pro Asn Leu Arg Val Val Arg Gly Thr Gln Val Tyr Asp
             100                 105                 110
Gly Lys Phe Ala Ile Phe Val Met Leu Asn Tyr Asn Thr Asn Ser Ser
             115                 120                 125
His Ala Leu Arg Gln Leu Arg Leu Thr Gln Leu Thr Glu Ile Leu Ser
 130                 135                 140
Gly Gly Val Tyr Ile Glu Lys Asn Asp Lys Leu Cys His Met Asp Thr
145                 150                 155                 160
Ile Asp Trp Arg Asp Ile Val Arg Asp Arg Asp Ala Glu Ile Val Val
                 165                 170                 175
Lys Asp Asn Gly Arg Ser Cys Pro Pro Cys His Glu Val Cys Lys Gly
             180                 185                 190
Arg Cys Trp Gly Pro Gly Ser Glu Asp Cys Gln Thr Leu Thr Lys Thr
             195                 200                 205
Ile Cys Ala Pro Gln Cys Asn Gly His Cys Phe Gly Pro Asn Pro Asn
 210                 215                 220
Gln Cys Cys His Asp Glu Cys Ala Gly Gly Cys Ser Gly Pro Gln Asp
225                 230                 235                 240
Thr Asp Cys Phe Ala Cys Arg His Phe Asn Asp Ser Gly Ala Cys Val
             245                 250                 255
Pro Arg Cys Pro Gln Pro Leu Val Tyr Asn Lys Leu Thr Phe Gln Leu
             260                 265                 270
Glu Pro Asn Pro His Thr Lys Tyr Gln Tyr Gly Gly Val Cys Val Ala
             275                 280                 285
Ser Cys Pro His Asn Phe Val Val Asp Gln Thr Ser Cys Val Arg Ala
             290                 295                 300
Cys Pro Pro Asp Lys Met Glu Val Asp Lys Asn Gly Leu Lys Met Cys
305                 310                 315                 320
Glu Pro Cys Gly Gly Leu Cys Pro Lys Ala Cys Glu Gly Thr Gly Ser
                 325                 330                 335
Gly Ser Arg Phe Gln Thr Val Asp Ser Ser Asn Ile Asp Gly Phe Val
             340                 345                 350
Asn Cys Thr Lys Ile Leu Gly Asn Leu Asp Phe Leu Ile Thr Gly Leu
             355                 360                 365
Asn Gly Asp Pro Trp His Lys Ile Pro Ala Leu Asp Pro Glu Lys Leu
         370                 375                 380
Asn Val Phe Arg Thr Val Arg Glu Ile Thr Gly Tyr Leu Asn Ile Gln
385                 390                 395                 400
Ser Trp Pro Pro His Met His Asn Phe Ser Val Phe Ser Asn Leu Thr
                 405                 410                 415
Thr Ile Gly Gly Arg Ser Leu Tyr Asn Arg Gly Phe Ser Leu Leu Ile
             420                 425                 430
```

```
Met Lys Asn Leu Asn Val Thr Ser Leu Gly Phe Arg Ser Leu Lys Glu
            435                 440                 445

Ile Ser Ala Gly Arg Ile Tyr Ile Ser Ala Asn Arg Gln Leu Cys Tyr
    450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Asp Cys Gly Ser Leu
                485                 490                 495

Glu Asn Leu Pro Met Arg Pro Asn Ala Ser Pro Ala Thr Arg Asn Ala
                500                 505                 510

Asn Pro Trp Arg Ala Leu Pro His Ala Met Ala Arg Ala Leu Ile Leu
                515                 520                 525

Val Leu Asn Val Pro Ile Phe Glu Met Gly Pro Thr Val
                530                 535                 540

<210> SEQ ID NO 9
<211> LENGTH: 1668
<212> TYPE: DNA
<213> ORGANISM: Homo sapiens

<400> SEQUENCE: 9
atgagggcga acgacgctct gcaggtgctg ggcttgcttt tcagcctggc ccggggctcc      60
gaggtgggca actctcaggc agtgtgtcct gggactctga atggcctgag tgtgaccggc     120
gatgctgaga accaatacca gacactgtac aagctctacg agaggtgtga ggtggtgatg     180
gggaaccttg agattgtgct cacgggacac aatgccgacc tctccttcct gcagtggatt     240
cgagaagtga caggctatgt cctcgtggcc atgaatgaat ctctactctc accattgccc     300
aacctccgcg tggtgcgagg gacccaggtc tacgatggga agtttgccat cttcgtcatg     360
ttgaactata caccaactc cagccacgct ctgcgccagc tccgcttgac tcagctcacc     420
gagattctgt caggggtgt ttatattgag aagaacgata agctttgtca catggacaca     480
attgactgga gggacatcgt gagggaccga gatgctgaga tagtggtgaa ggacaatggc     540
agaagctgtc ccccctgtca tgaggtttgc aaggggcgat gctggggtcc tggatcagaa     600
gactgccaga cattgaccaa gaccatctgt gctcctcagt gtaatggtca ctgctttggg     660
cccaaccca accagtgctg ccatgatgag tgtgccgggg gctgctcagg ccctcaggac     720
acagactgct tgcctgccg gcacttcaat gacagtggag cctgtgtacc tcgctgtcca     780
cagcctcttg tctacaacaa gctaactttc agctggaac ccaatcccca caccaagtat     840
cagtatggag gagtttgtgt agccagctgt ccccataact tgtggtgga tcaaacatcc     900
tgtgtcaggg cctgtcctcc tgacaagatg gaagtagata aaatgggct caagatgtgt     960
gagccttgtg ggggactatg tcccaaagcc tgtgagggaa caggctctgg gagccgcttc    1020
cagactgtgg actcgagcaa cattgatgga tttgtgaact gcaccaagat cctgggcaac    1080
ctggactttc tgatcaccgg cctcaatgga gacccctggc acaagatccc tgccctggac    1140
ccagagaagc tcaatgtctt ccggacagta cgggagatca caggttacct gaacatccag    1200
tcctggccgc cccacatgca caacttcagt gttttttcca atttgacaac cattggaggc    1260
agaagcctct acaaccgggg cttctcattg ttgatcatga gaacttgaa tgtcacatct    1320
ctgggcttcc gatccctgaa ggaaattagt gctgggcgta tctatataag tgccaatagg    1380
cagctctgct accaccactc tttgaactgg accaaggtgc ttcgggggcc tacgaagag    1440
cgactagaca tcaagcataa tcggccgcgc agagactgcg tggcagaggg caaagtgtgt    1500
```

```
gacccactgt gctcctctgg gggatgctgg ggcccaggcc ctggtcagtg cttgtcctgt    1560
cgaaattata gccgaggagg tgtctgtgtg acccactgca actttctgaa tggggctctg    1620
atacttgtgc tcaatgtgcc cattttcgag atgggcccca ctgtgtga                1668
```

<210> SEQ ID NO 10
<211> LENGTH: 555
<212> TYPE: PRT
<213> ORGANISM: Homo sapiens

<400> SEQUENCE: 10

```
Met Arg Ala Asn Asp Ala Leu Gln Val Leu Gly Leu Leu Phe Ser Leu
 1               5                  10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
           100                 105                 110

Gly Lys Phe Ala Ile Phe Val Met Leu Asn Tyr Asn Thr Asn Ser Ser
       115                 120                 125

His Ala Leu Arg Gln Leu Arg Leu Thr Gln Leu Thr Glu Ile Leu Ser
   130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
           180                 185                 190

Arg Cys Trp Gly Pro Gly Ser Glu Asp Cys Gln Thr Leu Thr Lys Thr
       195                 200                 205

Ile Cys Ala Pro Gln Cys Asn Gly His Cys Phe Gly Pro Asn Pro Asn
   210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
           260                 265                 270

Glu Pro Asn Pro His Thr Lys Tyr Gln Tyr Gly Gly Val Cys Val Ala
       275                 280                 285

Ser Cys Pro His Asn Phe Val Val Asp Gln Thr Ser Cys Val Arg Ala
   290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
           340                 345                 350
```

```
Asn Cys Thr Lys Ile Leu Gly Asn Leu Asp Phe Leu Ile Thr Gly Leu
    355                 360                 365

Asn Gly Asp Pro Trp His Lys Ile Pro Ala Leu Asp Pro Glu Lys Leu
    370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
                420                 425                 430

Met Lys Asn Leu Asn Val Thr Ser Leu Gly Phe Arg Ser Leu Lys Glu
                435                 440                 445

Ile Ser Ala Gly Arg Ile Tyr Ile Ser Ala Asn Arg Gln Leu Cys Tyr
    450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                485                 490                 495

Gly Lys Val Cys Asp Pro Leu Cys Ser Ser Gly Gly Cys Trp Gly Pro
                500                 505                 510

Gly Pro Gly Gln Cys Leu Ser Cys Arg Asn Tyr Ser Arg Gly Gly Val
                515                 520                 525

Cys Val Thr His Cys Asn Phe Leu Asn Gly Ala Leu Ile Leu Val Leu
                530                 535                 540

Asn Val Pro Ile Phe Glu Met Gly Pro Thr Val
545                 550                 555

<210> SEQ ID NO 11
<211> LENGTH: 1710
<212> TYPE: DNA
<213> ORGANISM: Homo sapiens

<400> SEQUENCE: 11
atgagggcga acgacgctct gcaggtgctg ggcttgcttt tcagcctggc ccggggctcc        60
gaggtgggca actctcaggc agtgtgtcct gggactctga atggcctgag tgtgaccggc       120
gatgctgaga accaatacca gacactgtac aagctctacg agaggtgtga ggtggtgatg       180
gggaaccttg agattgtgct cacgggacac aatgccgacc tctccttcct gcagtggatt       240
cgagaagtga caggctatgt cctcgtggcc atgaatgaat ctctactctc accattgccc       300
aacctccgcg tggtgcgagg gacccaggtc tacgatggga gtttgccat cttcgtcatg       360 ttgaactata acaccaactc cagccacgct ctgcgccagc tccgcttgac tcagctcacc       420
gagattctgt caggggtgt ttatattgag aagaacgata agctttgtca catggacaca       480
attgactgga gggacatcgt gagggaccga gatgctgaga tagtggtgaa ggacaatggc       540
agaagctgtc cccctgtca tgaggtttgc aaggggcgat gctgggtcc tggatcagaa       600 gactgccaga cattgaccaa gaccatctgt gctcctcagt gtaatggtca ctgctttggg       660
cccaacccca accagtgctg ccatgatgag tgtgccgggg ctgctcagg ccctcaggac       720 acagactgct tgcctgccg gcacttcaat gacagtggag cctgtgtacc tcgctgtcca       780
cagcctcttg tctacaacaa gctaactttc agctggaac ccaatcccca caccaagtat       840
cagtatggag agtttgtgt agccagctgt ccccataact ttgtggtgga tcaaacatcc       900
tgtgtcaggg cctgtcctcc tgacaagatg gaagtagata aaaatgggct caagatgtgt       960
gagccttgtg ggggactatg tcccaaagcc tgtgagggaa caggctctgg gagccgcttc      1020
```

-continued

```
cagactgtgg actcgagcaa cattgatgga tttgtgaact gcaccaagat cctgggcaac      1080
ctggactttc tgatcaccgg cctcaatgga gaccctggc acaagatccc tgccctggac      1140
ccagagaagc tcaatgtctt ccggacagta cgggagatca caggttacct gaacatccag      1200
tcctggccgc cccacatgca aacttcagt gttttttcca atttgacaac cattggaggc      1260
agaagcctct acaacgggg cttctcattg ttgatcatga agaacttgaa tgtcacatct      1320
ctgggcttcc gatccctgaa ggaaattagt gctgggcgta tctatataag tgccaatagg      1380
cagctctgct accaccactc tttgaactgg accaaggtgc ttcgggggcc tacgaagag      1440 cgactagaca tcaagcataa tcggccgcgc agagactgcg tggcagaggg caaagtgtgt      1500
gacccactgt gctcctctgg gggatgctgg ggcccaggcc ctggtcagtg cttgtcctgt      1560
cgaaattata gccgaggagg tgtctgtgtg acccactgca acttctctgaa tggggagcct      1620 cgagaatttg cccatgaggc cgaatgcttc tcctgccacc cggaatgcca acccatggag      1680
ggcactgcca catgcaatgg ctcggtgtaa                                      1710
```

<210> SEQ ID NO 12
<211> LENGTH: 569
<212> TYPE: PRT
<213> ORGANISM: Homo sapiens

<400> SEQUENCE: 12

```
Met Arg Ala Asn Asp Ala Leu Gln Val Leu Gly Leu Leu Phe Ser Leu
 1               5                  10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255
```

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
            275                 280                 285

Ser Cys Pro His Asn Phe Val Val Asp Gln Thr Ser Cys Val Arg Ala
            290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
            325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
            355                 360                 365

Asn Gly Asp Pro Trp His Lys Ile Pro Ala Leu Asp Pro Glu Lys Leu
            370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
            405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
            435                 440                 445

Ile Ser Ala Gly Arg Ile Tyr Ile Ser Ala Asn Arg Gln Leu Cys Tyr
450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
            485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
            515                 520                 525

Cys Val Thr His Cys Asn Phe Leu Asn Gly Glu Pro Arg Glu Phe Ala
            530                 535                 540

His Glu Ala Glu Cys Phe Ser Cys His Pro Glu Cys Gln Pro Met Glu
545                 550                 555                 560

Gly Thr Ala Thr Cys Asn Gly Ser Val
                565

<210> SEQ ID NO 13
<211> LENGTH: 1689
<212> TYPE: DNA
<213> ORGANISM: Homo sapiens

<400> SEQUENCE: 13
atgagggcga acgacgctct gcaggtgctg ggcttgcttt tcagcctggc ccggggctcc      60
gaggtgggca actctcaggc agtgtgtcct gggactctga atggcctgag tgtgaccggc     120
gatgctgaga accaatacca gacactgtac aagctctacg agaggtgtga ggtggtgatg     180
gggaaccttg agattgtgct cacgggacac aatgccgacc tctccttcct gcagtggatt     240
cgagaagtga caggctatgt cctcgtggcc atgaatgaat ctctactcta accattgccc     300
aacctccgcg tggtgcgagg gacccaggtc tacgatggga agtttgccat cttcgtcatg     360

```
ttgaactata acaccaactc cagccacgct ctgcgccagc tccgcttgac tcagctcacc     420
gagattctgt cagggggtgt ttatattgag aagaacgata agctttgtca catggacaca     480
attgactgga gggacatcgt gagggaccga gatgctgaga tagtggtgaa ggacaatggc     540
agaagctgtc cccctgtca tgaggtttgc aagggcgat gctgggtcc tggatcagaa       600 gactgccaga cattgaccaa gaccatctgt gctcctcagt gtaatggtca ctgctttggg     660 cccaaccca accagtgctg ccatgatgag tgtgccgggg gctgctcagg ccctcaggac      720
acagactgct ttgcctgccg gcacttcaat gacagtggag cctgtgtacc tcgctgtcca    780
cagcctcttg tctacaacaa gctaactttc cagctggaac ccaatcccca caccaagtat    840
cagtatggag gagtttgtgt agccagctgt ccccataact ttgtggtgga tcaaacatcc    900
tgtgtcaggg cctgtcctcc tgacaagatg gaagtagata aaaatgggct caagatgtgt   960
gagccttgtg ggggactatg tcccaaagcc tgtgagggaa caggctctgg gagccgcttc   1020
cagactgtgg actcgagcaa cattgatgga tttgtgaact gcaccaagat cctgggcaac   1080
ctggactttc tgatcaccgg cctcaatgga ccccctggc acaagatccc tgccctggac    1140
ccagagaagc tcaatgtctt ccggacagta cgggagatca caggttaccc tgaacatccag 1200 tcctggccgc cccacatgca caacttcagt gttttttcca attgacaac cattggaggc    1260 agaagcctct acaaccgggg cttctcattg ttgatcatga agaacttgaa tgtcacatct   1320
ctgggcttcc gatccctgaa ggaaattagt gctgggcgta tctatataag tgccaatagg   1380
cagctctgct accaccactc tttgaactgg accaaggtgc ttcgggggcc tacgaagag    1440 cgactagaca tcaagcataa tcggccgcgc agagactgcg tggcagaggg caaagtgtgt   1500
gacccactgt gctcctctgg gggatgctgg ggcccaggcc ctggtcagtg cttgtcctgt   1560
cgaaattata gccgaggagg tgtctgtgtg acccactgca actttctgaa tgggtacagt   1620
aaggggagcc agtcaaggat gggtgggggt ggggccctgc aatggaactg ttcaggtggc   1680
atacaataa                                                           1689
```

<210> SEQ ID NO 14
<211> LENGTH: 562
<212> TYPE: PRT
<213> ORGANISM: Homo sapiens

<400> SEQUENCE: 14

```
Met Arg Ala Asn Asp Ala Leu Gln Val Leu Gly Leu Leu Phe Ser Leu
  1               5                  10                  15

Ala Arg Gly Ser Glu Val Gly Asn Ser Gln Ala Val Cys Pro Gly Thr
                 20                  25                  30

Leu Asn Gly Leu Ser Val Thr Gly Asp Ala Glu Asn Gln Tyr Gln Thr
             35                  40                  45

Leu Tyr Lys Leu Tyr Glu Arg Cys Glu Val Val Met Gly Asn Leu Glu
         50                  55                  60

Ile Val Leu Thr Gly His Asn Ala Asp Leu Ser Phe Leu Gln Trp Ile
 65                  70                  75                  80

Arg Glu Val Thr Gly Tyr Val Leu Val Ala Met Asn Glu Phe Ser Thr
                 85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
```

```
                130                 135                 140
Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
                180                 185                 190

Arg Cys Trp Gly Pro Gly Ser Glu Asp Cys Gln Thr Leu Thr Lys Thr
                195                 200                 205

Ile Cys Ala Pro Gln Cys Asn Gly His Cys Phe Gly Pro Asn Pro Asn
                210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
                260                 265                 270

Glu Pro Asn Pro His Thr Lys Tyr Gln Tyr Gly Gly Val Cys Val Ala
                275                 280                 285

Ser Cys Pro His Asn Phe Val Val Asp Gln Thr Ser Cys Val Arg Ala
                290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
                340                 345                 350

Asn Cys Thr Lys Ile Leu Gly Asn Leu Asp Phe Leu Ile Thr Gly Leu
                355                 360                 365

Asn Gly Asp Pro Trp His Lys Ile Pro Ala Leu Asp Pro Glu Lys Leu
                370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
                420                 425                 430

Met Lys Asn Leu Asn Val Thr Ser Leu Gly Phe Arg Ser Leu Lys Glu
                435                 440                 445

Ile Ser Ala Gly Arg Ile Tyr Ile Ser Ala Asn Arg Gln Leu Cys Tyr
                450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                485                 490                 495

Gly Lys Val Cys Asp Pro Leu Cys Ser Ser Gly Gly Cys Trp Gly Pro
                500                 505                 510

Gly Pro Gly Gln Cys Leu Ser Cys Arg Asn Tyr Ser Arg Gly Gly Val
                515                 520                 525

Cys Val Thr His Cys Asn Phe Leu Asn Gly Tyr Ser Lys Gly Ser Gln
                530                 535                 540

Ser Arg Met Gly Gly Gly Ala Leu Gln Trp Asn Cys Ser Gly Gly
545                 550                 555                 560
```

Ile Gln

<210> SEQ ID NO 15
<211> LENGTH: 261
<212> TYPE: DNA
<213> ORGANISM: Homo sapiens

<400> SEQUENCE: 15

| | | | | | |
|---|---|---|---|---|---|
| cctggggtg | tcagtgccag | ccccccacaa | atcttttctg | ccccccccag | gaggctgacc | 60 |
| agtgtgtggc | ctgtgcccac | tataaggacc | ctcccttctg | cgtggcccgc | tgccccagcg | 120 |
| gtgtgaaacc | tgacctctcc | tacatgccca | tctggaagtt | tccagatgag | gagggcgcat | 180 |
| gccagccttg | ccccatcaac | tgcacccact | cgtgagtcca | acggtctttt | ctgcagaaag | 240 |
| gaggactttc | ctttcagggg | t | | | | 261 |

<210> SEQ ID NO 16
<211> LENGTH: 893
<212> TYPE: DNA
<213> ORGANISM: Homo sapiens

<400> SEQUENCE: 16

| | | | | | |
|---|---|---|---|---|---|
| cttgctggga | gtcctcagac | tcctctccta | acccaccccct | tcctttccag | tggcagaggg | 60 |
| caaagtgtgt | gacccactgt | gctcctctgg | gggatgctgg | ggcccaggcc | ctggtcagtg | 120 |
| cttgtcctgt | cgaaattata | gccgaggagg | tgtctgtgtg | acccactgca | actttctgaa | 180 |
| tgggtacagt | aaggggagcc | agtcaaggat | gggtgggggt | ggggccctgc | aatggaactg | 240 |
| ttcaggtggc | atacaataaa | agtctttaga | cagctttctg | catgtgcctt | ggtgggattg | 300 |
| aggtaggaga | cctgtggttg | tgagatcgga | gcatgaaggt | caggacttgg | aagtgacccc | 360 |
| cccctcccctt | tattccccac | tacagggagc | ctcgagaatt | tgcccatgag | gccgaatgct | 420 |
| tctcctgcca | cccggaatgc | caacccatgg | agggcactgc | cacatgcaat | ggctcggtat | 480 |
| actagtagca | ccaggatctc | caagggagac | agagaagggg | caatacttgg | agcatctggg | 540 |
| gaatgatatg | gctaaggata | gcacagagag | gccagataat | gctagggcct | gcagatagaa | 600 |
| gatcctgaat | gtctgggttg | gtcttttgctg | ggaggtatgg | aattgacctt | gggatctgat | 660 |
| tcttcctgac | cttctctctt | ccactcaggg | ctctgatact | tgtgctcaat | gtgcccattt | 720 |
| tcgagatggg | ccccactgtg | tgagcagctg | ccccccatgga | gtcctaggtg | ccaagggccc | 780 |
| aatctacaag | tacccagatg | ttcagaatga | atgtcggccc | tgccatgaga | actgcaccca | 840 |
| ggggtcagtg | atgggataat | aaggagaggg | ggtcaggtgg | aagggtagga | gca | 893 |

<210> SEQ ID NO 17
<211> LENGTH: 180
<212> TYPE: DNA
<213> ORGANISM: Homo sapiens

<400> SEQUENCE: 17

| | | | | | |
|---|---|---|---|---|---|
| gccagcactt | tgggaggctg | agatgggaag | atcacttgag | cccagaatta | gagataagcc | 60 |
| tatggaaaca | tagcaagaca | ctgtctctac | agggggaaaaa | aaaaaaagaa | actgagcctt | 120 |
| aaagagatga | aataaattaa | gcagtagatc | caggatgcaa | aatcctccca | attcctgtgc | 180 |

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotides

```
<400> SEQUENCE: 18
gggcagaaaa gatttgtggg                                          20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 19
cacactggtc agcctcctgg                                          20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 20
gccacacact ggtcagcctc                                          20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 21
ctcacgagtg ggtgcagttg                                          20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 22
gttggactca cgagtgggtg                                          20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 23
gaccgttgga ctcacgagtg                                          20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 24
gaccgttgga ctcacgagtg                                          20

<210> SEQ ID NO 25
<211> LENGTH: 16
<212> TYPE: DNA
```

```
<213> ORGANISM: Artificial Sequence
<220> FEATURE:
<223> OTHER INFORMATION: Synthetic oligonucleotides

<400> SEQUENCE: 25
cgttggactc acgagt                                                       16

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 26
gggtcacttc caagtcctga                                                   20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 27
gtcacttcca agtcctgacc                                                   20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 28
cacttccaag tcctgacctt                                                   20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 29
cttccaagtc ctgaccttca                                                   20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 30
cccttactgt acccattcag                                                   20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 31
ctccccttac tgtacccatt                                                   20
```

```
<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 32
tggctcccct tactgtaccc                                               20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 33
ctcgaggctc cctgtagtgg                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 34
attctcgagg ctccctgtag                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 35
caaattctcg aggctccctg                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 36
ctagtatacc gagccattgc                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 37
gtgctactag tataccgagc                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotides
```

```
<400> SEQUENCE: 38
caagtatcag agccctgagt                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 39
ttatcccatc actgacccct                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 40
tattatccca tcactgaccc                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 41
atttcatctc tttaaggctc                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 42
ctggatctac tgcttaattt                                               20

<210> SEQ ID NO 43
<211> LENGTH: 18
<212> TYPE: DNA
<213> ORGANISM: Artificial Sequence
<220> FEATURE:
<223> OTHER INFORMATION: Synthetic oligonucleotides

<400> SEQUENCE: 43
gctattacct taacccag                                                 18

<210> SEQ ID NO 44
<211> LENGTH: 100
<212> TYPE: DNA
<213> ORGANISM: Homo sapiens

<400> SEQUENCE: 44
cctgggggtg tcagtgccag ccccccacaa atcttttctg cccccccag gaggctgacc    60 agtgtgtggc ctgtgcccac tataaggacc ctcccttctg                        100

<210> SEQ ID NO 45
<211> LENGTH: 100
<212> TYPE: DNA
```

-continued

```
<213> ORGANISM: Homo sapiens

<400> SEQUENCE: 45
ccagatgagg agggcgcatg ccagccttgc cccatcaact gcacccactc gtgagtccaa    60
cggtcttttc tgcagaaagg aggactttcc tttcaggggt                         100

<210> SEQ ID NO 46
<211> LENGTH: 100
<212> TYPE: DNA
<213> ORGANISM: Homo sapiens

<400> SEQUENCE: 46
cttgctggga gtcctcagac tcctctccta acccacccct tcctttccag tggcagaggg    60
caaagtgtgt gacccactgt gctcctctgg gggatgctgg                         100

<210> SEQ ID NO 47
<211> LENGTH: 100
<212> TYPE: DNA
<213> ORGANISM: Homo sapiens

<400> SEQUENCE: 47
aattatagcc gaggaggtgt ctgtgtgacc cactgcaact ttctgaatgg gtacagtaag    60
gggagccagt caaggatggg tgggggtggg gccctgcaat                         100

<210> SEQ ID NO 48
<211> LENGTH: 100
<212> TYPE: DNA
<213> ORGANISM: Homo sapiens

<400> SEQUENCE: 48
aaggtcagga cttggaagtg acccccccct ccctttattc cccactacag ggagcctcga    60
gaatttgccc atgaggccga atgcttctcc tgccacccgg                         100

<210> SEQ ID NO 49
<211> LENGTH: 100
<212> TYPE: DNA
<213> ORGANISM: Homo sapiens

<400> SEQUENCE: 49
gccacccgga atgccaaccc atggagggca ctgccacatg caatggctcg gtatactagt    60
agcaccagga tctccaaggg agacagagaa ggggcaatac                         100

<210> SEQ ID NO 50
<211> LENGTH: 100
<212> TYPE: DNA
<213> ORGANISM: Homo sapiens

<400> SEQUENCE: 50
ggaattgacc ttgggatctg attcttcctg accttctctc ttccactcag ggctctgata    60
cttgtgctca atgtgcccat tttcgagatg ggccccactg                         100

<210> SEQ ID NO 51
<211> LENGTH: 100
<212> TYPE: DNA
<213> ORGANISM: Homo sapiens

<400> SEQUENCE: 51
ccagatgttc agaatgaatg tcggccctgc catgagaact gcacccaggg gtcagtgatg    60
ggataataag gagagggggt caggtggaag ggtaggagca                         100
```

<210> SEQ ID NO 52
<211> LENGTH: 10
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (9)..(9)
<223> OTHER INFORMATION: Xaa is 6-aminohexanoic acid
<220> FEATURE:
<221> NAME/KEY: MOD_RES
<222> LOCATION: (10)..(10)
<223> OTHER INFORMATION: Xaa is beta-alanine

<400> SEQUENCE: 52

Arg Arg Arg Arg Arg Arg Arg Arg Xaa Xaa
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2), (8), (13)
<223> OTHER INFORMATION: Xaa is 6-aminohexanoic acid
<220> FEATURE:
<221> NAME/KEY: MOD_RES
<222> LOCATION: (5), (11), (14)
<223> OTHER INFORMATION: Xaa is beta-alanine

<400> SEQUENCE: 53

Arg Xaa Arg Arg Xaa Arg Arg Xaa Arg Arg Xaa Arg Xaa Xaa
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2), (5), (8), (13)
<223> OTHER INFORMATION: Xaa is 6-aminohexanoic acid
<220> FEATURE:
<221> NAME/KEY: MOD_RES
<222> LOCATION: (11), (14)
<223> OTHER INFORMATION: Xaa is beta-alanine

<400> SEQUENCE: 54

Arg Xaa Arg Arg Xaa Arg Arg Xaa Arg Arg Xaa Arg Xaa Xaa
1               5                   10

<210> SEQ ID NO 55
<211> LENGTH: 17
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2), (4), (6), (8), (10), (14), (17)
<223> OTHER INFORMATION: Xaa is beta-alanine
<220> FEATURE:
<221> NAME/KEY: MOD_RES
<222> LOCATION: (12), (16)
<223> OTHER INFORMATION: Xaa is 6-aminohexanoic acid

<400> SEQUENCE: 55

Arg Xaa Arg Xaa Arg Xaa Arg Xaa Arg Xaa Arg Xaa Arg Xaa Arg Xaa Xaa
1               5                   10                  15

<210> SEQ ID NO 56
<211> LENGTH: 17
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2), (4), (6), (10), (12), (14)
<223> OTHER INFORMATION: Xaa is beta-alanine
<220> FEATURE:
<221> NAME/KEY: MOD_RES
<222> LOCATION: (8), (16), (17)
<223> OTHER INFORMATION: Xaa is 6-aminohexanoic acid

<400> SEQUENCE: 56

Arg Xaa Arg Xaa Arg Xaa Arg Xaa Arg Xaa Arg Xaa Arg Xaa Arg Xaa Xaa
1               5                   10                  15

<210> SEQ ID NO 57
<211> LENGTH: 17
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (1), (9), (17)
<223> OTHER INFORMATION: Xaa is 6-aminohexanoic acid
<220> FEATURE:
<221> NAME/KEY: MOD_RES
<222> LOCATION: (3), (5), (7), (11), (13), (15)
<223> OTHER INFORMATION: Xaa is beta-alanine

<400> SEQUENCE: 57

Xaa Arg Xaa Arg Xaa Arg Xaa Arg Xaa Arg Xaa Arg Xaa Arg Xaa Arg Xaa
1               5                   10                  15

<210> SEQ ID NO 58
<211> LENGTH: 17
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2), (6), (10), (14), (17)
<223> OTHER INFORMATION: Xaa is beta-alanine
<220> FEATURE:
<221> NAME/KEY: MOD_RES
<222> LOCATION: (4), (8), (12), (16)
<223> OTHER INFORMATION: Xaa is 6-aminohexanoic acid

<400> SEQUENCE: 58

Arg Xaa Arg Xaa Arg Xaa Arg Xaa Arg Xaa Arg Xaa Arg Xaa Arg Xaa Xaa
1               5                   10                  15

<210> SEQ ID NO 59
<211> LENGTH: 17
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2), (4), (6), (8), (17)
<223> OTHER INFORMATION: Xaa is beta-alanine
<220> FEATURE:
<221> NAME/KEY: MOD_RES

```
<222> LOCATION: (10), (12), (14, (16)
<223> OTHER INFORMATION: Xaa is 6-aminohexanoic acid

<400> SEQUENCE: 59

Arg Xaa Arg Xaa Arg Xaa Arg Xaa Arg Xaa Arg Xaa Arg Xaa Arg Xaa
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2), (8), (16)
<223> OTHER INFORMATION: Xaa is 6-aminohexanoic acid
<220> FEATURE:
<221> NAME/KEY: MOD_RES
<222> LOCATION: (4), (6), (10), (12), (14)
<223> OTHER INFORMATION: Xaa is beta-alanine

<400> SEQUENCE: 60

Arg Xaa Arg Xaa Arg Xaa Arg Xaa Arg Xaa Arg Xaa Arg Xaa Arg Xaa
1               5                   10                  15

<210> SEQ ID NO 61
<211> LENGTH: 14
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)...(13)
<223> OTHER INFORMATION: Xaa is 6-aminohexanoic acid
<220> FEATURE:
<221> NAME/KEY: MOD_RES
<222> LOCATION: (14)...(14)
<223> OTHER INFORMATION: Xaa is beta-alanine

<400> SEQUENCE: 61

Arg Xaa Arg Arg Xaa Arg Arg Xaa Arg Arg Xaa Arg Xaa Xaa
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)...(13)
<223> OTHER INFORMATION: Xaa is 6-aminohexanoic acid
<220> FEATURE:
<221> NAME/KEY: MOD_RES
<222> LOCATION: (14)...(14)
<223> OTHER INFORMATION: Xaa is beta-alanine

<400> SEQUENCE: 62

Arg Xaa Arg Arg Xaa Arg Arg Xaa Arg Arg Xaa Arg Xaa Xaa
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
```

```
<222> LOCATION: (3)...(12)
<223> OTHER INFORMATION: Xaa is 6-aminohexanoic acid
<220> FEATURE:
<221> NAME/KEY: MOD_RES
<222> LOCATION: (13)...(13)
<223> OTHER INFORMATION: Xaa is beta-alanine

<400> SEQUENCE: 63

Arg Arg Xaa Arg Arg Xaa Arg Arg Xaa Arg Arg Xaa Xaa
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (1)...(13)
<223> OTHER INFORMATION: Xaa is 6-aminohexanoic acid
<220> FEATURE:
<221> NAME/KEY: MOD_RES
<222> LOCATION: (14)...(14)
<223> OTHER INFORMATION: Xaa is beta-alanine

<400> SEQUENCE: 64

Xaa Arg Arg Xaa Arg Arg Xaa Arg Arg Xaa Arg Arg Xaa Xaa
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)...(12)
<223> OTHER INFORMATION: Xaa is 6-aminohexanoic acid
<220> FEATURE:
<221> NAME/KEY: MOD_RES
<222> LOCATION: (13)...(13)
<223> OTHER INFORMATION: Xaa is beta-alanine

<400> SEQUENCE: 65

Arg Xaa Arg Xaa Arg Xaa Arg Xaa Arg Xaa Arg Xaa Xaa
1               5                   10

<210> SEQ ID NO 66
<211> LENGTH: 15
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)...(14)
<223> OTHER INFORMATION: Xaa is 6-aminohexanoic acid
<220> FEATURE:
<221> NAME/KEY: MOD_RES
<222> LOCATION: (15)...(15)
<223> OTHER INFORMATION: Xaa is beta-alanine

<400> SEQUENCE: 66

Arg Xaa Arg Xaa Arg Xaa Arg Xaa Arg Xaa Arg Xaa Arg Xaa Xaa
1               5                   10                  15

<210> SEQ ID NO 67
<211> LENGTH: 11
<212> TYPE: PRT
<213> ORGANISM: Artificial Sequence
```

```
<220> FEATURE:
<223> OTHER INFORMATION: Synthetic arginine-rich peptide
<220> FEATURE:
<221> NAME/KEY: MOD_RES
<222> LOCATION: (2)...(10)
<223> OTHER INFORMATION: Xaa is 6-aminohexanoic acid
<220> FEATURE:
<221> NAME/KEY: MOD_RES
<222> LOCATION: (11)...(11)
<223> OTHER INFORMATION: Xaa is beta-alanine

<400> SEQUENCE: 67

Arg Xaa Arg Arg Xaa Arg Arg Xaa Arg Xaa Xaa
1               5                   10

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
caccatggag ctggcggcct                                                   20

<210> SEQ ID NO 69
<211> LENGTH: 21
<212> TYPE: DNA
<213> ORGANISM: Artificial Sequence
<220> FEATURE:
<223> OTHER INFORMATION: Primer

<400> SEQUENCE: 69
tccaggtcca cacagcggtc c                                                 21

<210> SEQ ID NO 70
<211> LENGTH: 98
<212> TYPE: DNA
<213> ORGANISM: Homo sapiens

<400> SEQUENCE: 70
tcccaagagg gtggttccca gaattgttga tgagactgtt tctcctgcag ctgtgtggac       60
ctggatgaca agggctgccc cgccgagcag agagccag                              98

<210> SEQ ID NO 71
<211> LENGTH: 104
<212> TYPE: DNA
<213> ORGANISM: Homo sapiens

<400> SEQUENCE: 71
gagcctctgc tgtccaagct ctcatttaag gtggtgactt tcttccctag gtgtaaagga      60
ccagagcttc aagactgttt aggacaaaca ctggtgctga tcgg                      104

<210> SEQ ID NO 72
<211> LENGTH: 6
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 1,3,5
<223> OTHER INFORMATION: n = any locked nucleic acid
<220> FEATURE:
<221> NAME/KEY: misc_feature
<222> LOCATION: 2, 4, 6
<223> OTHER INFORMATION: n = any base
```

```
<400> SEQUENCE: 72 nnnnnn                                                              6

<210> SEQ ID NO 73
<211> LENGTH: 6
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 1, 2, 4, 5
<223> OTHER INFORMATION: n = any locked nucleic acid
<220> FEATURE:
<221> NAME/KEY: misc_feature
<222> LOCATION: 3, 6
<223> OTHER INFORMATION: n = any base

<400> SEQUENCE: 73 nnnnnn                                                              6

<210> SEQ ID NO 74
<211> LENGTH: 6
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 1, 4
<223> OTHER INFORMATION: n = any locked nucleic acid
<220> FEATURE:
<221> NAME/KEY: misc_feature
<222> LOCATION: 2, 3, 5, 6
<223> OTHER INFORMATION: n = any base

<400> SEQUENCE: 74 nnnnnn                                                              6

<210> SEQ ID NO 75
<211> LENGTH: 15
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 1, 3, 6, 7, 10, 12, 14, 15
<223> OTHER INFORMATION: n = any locked nucleic acid
<220> FEATURE:
<221> NAME/KEY: misc_feature
<222> LOCATION: 2, 4, 5, 8, 9, 11, 13
<223> OTHER INFORMATION: n = any base

<400> SEQUENCE: 75 nnnnnnnnn nnnnn                                                    15

<210> SEQ ID NO 76
<211> LENGTH: 15
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 1, 3, 5, 6, 7, 10, 11, 12, 14, 15
<223> OTHER INFORMATION: n = any locked nucleic acid
<220> FEATURE:
<221> NAME/KEY: misc_feature
<222> LOCATION: 2, 4, 8, 9, 13
<223> OTHER INFORMATION: n = any base
```

```
<400> SEQUENCE: 76
nnnnnnnnnn nnnnn                                                    15

<210> SEQ ID NO 77
<211> LENGTH: 15
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 1, 3, 6, 7, 10, 12, 14, 15
<223> OTHER INFORMATION: n = any locked nucleic acid
<220> FEATURE:
<221> NAME/KEY: modified_base
<222> LOCATION: 2, 4, 5, 8, 9, 11, 13
<223> OTHER INFORMATION: n = any 2' MOE modified base

<400> SEQUENCE: 77
nnnnnnnnnn nnnnn                                                    15

<210> SEQ ID NO 78
<211> LENGTH: 15
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 1, 3, 5, 6, 7, 10, 11, 12, 14, 15
<223> OTHER INFORMATION: n = any locked nucleic acid
<220> FEATURE:
<221> NAME/KEY: modified_base
<222> LOCATION: 2, 4, 8, 9, 13
<223> OTHER INFORMATION: n = any 2' MOE modified base

<400> SEQUENCE: 78
nnnnnnnnnn nnnnn                                                    15

<210> SEQ ID NO 79
<211> LENGTH: 15
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 1, 3, 6, 7, 10, 12, 14, 15
<223> OTHER INFORMATION: n = any locked nucleic acid
<220> FEATURE:
<221> NAME/KEY: modified_base
<222> LOCATION: 2, 4, 5, 8, 9, 11, 13
<223> OTHER INFORMATION: n = any 2' fluoro modified base

<400> SEQUENCE: 79
nnnnnnnnnn nnnnn                                                    15

<210> SEQ ID NO 80
<211> LENGTH: 15
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 1, 3, 5, 6, 7, 10, 11, 12, 14, 15
<223> OTHER INFORMATION: n = any locked nucleic acid
<220> FEATURE:
<221> NAME/KEY: modified_base
<222> LOCATION: 2, 4, 8, 9, 13
<223> OTHER INFORMATION: n = any 2' fluoro modified base
```

```
<400> SEQUENCE: 80
nnnnnnnnnn nnnnn                                                    15

<210> SEQ ID NO 81
<211> LENGTH: 10
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 1, 4, 7, 10
<223> OTHER INFORMATION: n = any locked nucleic acid
<220> FEATURE:
<221> NAME/KEY: misc_feature
<222> LOCATION: 2, 3, 5, 6, 8, 9
<223> OTHER INFORMATION: n = any base

<400> SEQUENCE: 81 nnnnnnnnnn                                                          10

<210> SEQ ID NO 82
<211> LENGTH: 10
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 2, 5, 8
<223> OTHER INFORMATION: n = any locked nucleic acid
<220> FEATURE:
<221> NAME/KEY: misc_feature
<222> LOCATION: 1, 3, 4, 6, 7, 9, 10
<223> OTHER INFORMATION: n = any base

<400> SEQUENCE: 82 nnnnnnnnnn                                                          10

<210> SEQ ID NO 83
<211> LENGTH: 10
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 3, 6, 9
<223> OTHER INFORMATION: n = any locked nucleic acid
<220> FEATURE:
<221> NAME/KEY: misc_feature
<222> LOCATION: 1, 2, 4, 5, 7, 8, 10
<223> OTHER INFORMATION: n = any base

<400> SEQUENCE: 83 nnnnnnnnnn                                                          10

<210> SEQ ID NO 84
<211> LENGTH: 10
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 1, 4, 7, 10
<223> OTHER INFORMATION: n = any locked nucleic acid
<220> FEATURE:
<221> NAME/KEY: modified_base
<222> LOCATION: 2, 3, 5, 6, 8, 9
<223> OTHER INFORMATION: n = any 2' MOE modified base
```

```
<400> SEQUENCE: 84 nnnnnnnnnn                                                        10

<210> SEQ ID NO 85
<211> LENGTH: 10
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 2, 5, 8
<223> OTHER INFORMATION: n = any locked nucleic acid
<220> FEATURE:
<221> NAME/KEY: modified_base
<222> LOCATION: 1, 3, 4, 6, 7, 9, 10
<223> OTHER INFORMATION: n = any 2' MOE modified base

<400> SEQUENCE: 85 nnnnnnnnnn                                                        10

<210> SEQ ID NO 86
<211> LENGTH: 10
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 3, 6, 9
<223> OTHER INFORMATION: n = any locked nucleic acid
<220> FEATURE:
<221> NAME/KEY: modified_base
<222> LOCATION: 1, 2, 4, 5, 7, 8, 10
<223> OTHER INFORMATION: n = any 2' MOE modified base

<400> SEQUENCE: 86 nnnnnnnnnn                                                        10

<210> SEQ ID NO 87
<211> LENGTH: 10
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 1, 4, 7, 10
<223> OTHER INFORMATION: n = any locked nucleic acid
<220> FEATURE:
<221> NAME/KEY: modified_base
<222> LOCATION: 2, 3, 5 , 6, 8, 9
<223> OTHER INFORMATION: n = any 2' fluoro modified base

<400> SEQUENCE: 87 nnnnnnnnnn                                                        10

<210> SEQ ID NO 88
<211> LENGTH: 10
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 2, 5, 8
<223> OTHER INFORMATION: n = any locked nucleic acid
<220> FEATURE:
<221> NAME/KEY: modified_base
<222> LOCATION: 1, 3, 4, 6, 7, 9, 10
<223> OTHER INFORMATION: n = any 2' fluoro modified base
```

<400> SEQUENCE: 88 nnnnnnnnnn                                                                          10

<210> SEQ ID NO 89
<211> LENGTH: 10
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 3, 6, 9
<223> OTHER INFORMATION: n = any locked nucleic acid
<220> FEATURE:
<221> NAME/KEY: modified_base
<222> LOCATION: 1, 2, 4, 5, 7, 8, 10
<223> OTHER INFORMATION: n = any 2' fluoro modified base

<400> SEQUENCE: 89 nnnnnnnnnn                                                                          10

<210> SEQ ID NO 90
<211> LENGTH: 10
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 2, 4, 6, 8, 10
<223> OTHER INFORMATION: n = any locked nucleic acid
<220> FEATURE:
<221> NAME/KEY: misc_feature
<222> LOCATION: 1, 3, 5, 7, 9
<223> OTHER INFORMATION: n = any base

<400> SEQUENCE: 90 nnnnnnnnnn                                                                          10

<210> SEQ ID NO 91
<211> LENGTH: 9
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 1, 3, 5, 7, 9
<223> OTHER INFORMATION: n = any locked nucleic acid
<220> FEATURE:
<221> NAME/KEY: misc_feature
<222> LOCATION: 2, 4, 6, 8
<223> OTHER INFORMATION: n = any base

<400> SEQUENCE: 91 nnnnnnnnn                                                                            9

<210> SEQ ID NO 92
<211> LENGTH: 10
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 2, 4, 6, 8, 10
<223> OTHER INFORMATION: n = any locked nucleic acid
<220> FEATURE:
<221> NAME/KEY: modified_base
<222> LOCATION: 1, 3, 5, 7, 9
<223> OTHER INFORMATION: n = any 2' MOE modified base

```
<400> SEQUENCE: 92 nnnnnnnnnn                                                              10

<210> SEQ ID NO 93
<211> LENGTH: 9
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 1, 3, 5, 7, 9
<223> OTHER INFORMATION: n = any locked nucleic acid
<220> FEATURE:
<221> NAME/KEY: modified_base
<222> LOCATION: 2, 4, 6, 8
<223> OTHER INFORMATION: n = and 2' MOE modified base

<400> SEQUENCE: 93 nnnnnnnnn                                                               9

<210> SEQ ID NO 94
<211> LENGTH: 10
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 2, 4, 6, 8, 10
<223> OTHER INFORMATION: n = any locked nucleic acid
<220> FEATURE:
<221> NAME/KEY: modified_base
<222> LOCATION: 1, 3, 5, 7, 9
<223> OTHER INFORMATION: n = any 2' fluoro modified base

<400> SEQUENCE: 94 nnnnnnnnnn                                                              10

<210> SEQ ID NO 95
<211> LENGTH: 9
<212> TYPE: DNA
<213> ORGANISM: Artificial Sequence
<220> FEATURE:
<223> OTHER INFORMATION: Splice switching oligomer
<220> FEATURE:
<221> NAME/KEY: modified_base
<222> LOCATION: 1, 3, 5, 7, 9
<223> OTHER INFORMATION: n = any locked nucleic acid
<220> FEATURE:
<221> NAME/KEY: modified_base
<222> LOCATION: 2 ,4, 6, 8
<223> OTHER INFORMATION: n = any 2' fluoro modified base

<400> SEQUENCE: 95 nnnnnnnnn                                                               9
```

SOLUBLE HER2 AND HER3 SPLICE VARIANT PROTEINS, SPLICE-SWITCHING OLIGONUCLEOTIDES, AND THEIR USE IN THE TREATMENT OF DISEASE

This application claims priority to U.S. Provisional Patent Application No. 60/956,887 filed Aug. 20, 2007 and U.S. Provisional Patent Application No. 60/942,319 filed Jun. 6, 2007, both of which are incorporated herein in their entirety by reference.

The Sequence Listing associated with this application is provided in text format in lieu of a paper copy, and is hereby incorporated by reference into the specification. The name of the text file containing the Sequence Listing is 120178_444_SEQUENCE_LISTING.txt. The text file is 86 KB, was created on Jun. 30, 2010, and is being submitted electronically via EFS-Web.

FIELD OF THE INVENTION

The present invention relates generally to the fields of protein and nucleotide chemistry and biochemistry, and to biotechnology and medicine. More specifically, it relates to epidermal growth factor receptor (EGFR) antagonists, nucleic acids derived from epidermal growth factor receptors and their use in the treatment of proliferative diseases, such as cancer.

BACKGROUND OF THE INVENTION

Breast cancer is the most common cancer in women, aside from skin cancer. In 2006, according to the National Cancer Institute, approximately 41,000 women per year in the United States die from the disease. Based on current rates, 13.2% of women born today will be diagnosed with breast cancer at some time in their lives. Intensive research has led to advances in diagnosis and treatment; however, serious problems still exist, including low cure rates, substantial adverse effects and resistance to certain therapies. Given that breast cancer is a group of diseases, each having distinct molecular properties, molecularly targeted drugs have emerged as important anti-cancer therapeutics in recent years.

In 25-30% of breast cancers, amplification and overexpression of the growth factor receptor gene HER2 (human epidermal growth factor receptor-2, also known as neu/erbB2) is associated with enhanced tumor aggressiveness and a high risk of relapse and death (Slamon, D., et al., 1987, Science 235:177; Yarden, Y., 2001, Oncology 1:1). This oncogene encodes a 185 kilodalton (kDa) transmembrane receptor tyrosine kinase. As one of the four members of the human epidermal growth factor receptor (EGFR) family, HER2 distinguishes itself in several ways. First, HER2 is an orphan receptor. No high-affinity ligand has been identified. Second, HER2 is a preferred partner for other EGFR family members (HER1/EGFR, HER3, and HER4) for the formation of heterodimers, which show high ligand affinity and superior signaling activity. Third, full-length HER2 undergoes proteolytic cleavage, releasing a soluble extracellular domain (ECD). Shedding of the ECD has been shown to represent an alternative activation mechanism of full-length HER2 both in vitro and in vivo, as it leaves a membrane-anchored fragment with kinase activity. The central role of HER2 in EGFR family signaling correlates with its involvement in the oncogenesis of several types of cancers, such as breast, ovarian, colon, and gastric cancers, regardless of its expression level (Slamon, D., et al., 1989, Science 244:707; Hynes, N., et al., 1994, Biochem. Biophys. Acta. 1198:165). HER2 may also render tumor cells resistant to certain chemotherapeutics (Pegram, M., et al., 1997, Oncogene 15:537). Given its vital role in tumorigenesis, HER2 is an important target for cancer therapeutics.

As a cell membrane receptor, HER2 is composed of an extracellular domain (ECD) (632 amino acids), a transmembrane domain (22 amino acids), and an intracellular domain with tyrosine kinase activity (580 amino acids). As initially transcribed, the pre-mRNA for HER2 contains 27 exons and 26 introns. The fully spliced HER2 mRNA from which the introns have been spliced out is composed of 27 exons. Upon expression, HER2 protein is translocated to the cell surface. Activated through constitutive homo-dimerization and ligand-stimulated hetero-dimerization, HER2 protein directs subsequent steps in signal transduction, which affect cell growth, survival, and differentiation.

HER2 has been validated as a therapeutic target for several epithelial malignancies, including those originating in the breast, lung and colon. Currently there is only one FDA-approved therapeutic for HER2 positive breast cancer, Herceptin® (Colomer, R., et al., 2001, Cancer Investigation 19:49). Herceptin is a recombinant humanized monoclonal antibody that selectively binds to the HER2 extracellular domain with high affinity ($K_d$=5 nM). Alone or in combination with chemotherapy, Herceptin has been shown to inhibit the proliferation of human tumor cells that overexpress HER2 (Slamon, D., et al., 2001, N. Engl. J. Med. 344:783; Baselga, J., et al., 1998, Cancer Research 58:2825).

However, this antibody-based therapeutic reagent has certain limitations. First, its inhibitory effect is restricted to the HER2 displayed on the cell surface; intracellular HER2 molecules are still available for mitogenic signaling. Second, Herceptin can be bound and thus "neutralized" by circulating ECDs that are released by proteolysis of membrane-bound HER2 (Brodowicz, T., et al., 1997, Int. J. Cancer 73:875). Finally, as with many other drugs, prolonged treatment with Herceptin leads to acquired resistance (Kute, T., et al., 2004, Cytometry Part A 57A:86). Another anti-HER2 antibody, pertuzumab, has been shown in a phase II clinical trial to have activity in ovarian cancer (Gordon, M. S., et al., 2006, J. Clin. Oncol. 24:4324).

At least two autoinhibitors of HER2, translated from alternatively spliced HER2 mRNA species, have been reported. These are HER2-68 and HER2-100. Retention of intron 8 in the HER2 mRNA produces a variant mRNA that encodes a 68-kDa HER2 protein, HER2-68 or Herstatin. Retention of Intron 15 produces a variant mRNA that encodes a 100-kDa truncated HER2 protein, HER2-100. Both HER2 splice variants are soluble and act as dominant-negative inhibitors of HER2, most likely through interfering with receptor dimerization.

When HER2-100 is overexpressed in MCF-7 breast cancer cells, spontaneous proliferation and heregulin-mediated soft agar colony formation of MCF-7 cells decreases (Aigner, et al., 2001, Oncogene, 20(17):2101). Downstream signaling pathways are also negatively affected.

The 68-kDa variant, or Herstatin, has been characterized in more detail. Upon expression in tumor cells, Herstatin is secreted and binds to HER2-presenting cells with high affinity ($K_d$=14 nM); Herstatin also binds to HER1 and HER4. Herstatin interferes with the activity of HER2 and other EGFR family members, and thus interferes with their downstream signal transduction. Herstatin has been reported to cause tumor growth arrest and inhibition of breast cancer cell growth. Herstatin overcomes tamoxifen resistance in HER2 positive breast cancer cells (Justman, Q., et al., 2003, J. Biol. Chem. 277:20618; Jhavala-Romero, F., et al., 2003, Oncogene 22:8178). Therefore, Herstatin has been recognized as a promising anti-cancer drug candidate (Stix, G., 2006, Scientific American 294:60). With both HER2-100 and Herstatin, a progressive loss of their expression in more advanced tumors has been observed.

HER3 (human epidermal growth factor receptor-3, erbB3) is a receptor protein that plays an important role in regulating normal cell growth. HER3 lacks an intrinsic kinase activity and relies on the presence of HER2 to transduce signals across the cell membrane. As initially transcribed, the pre-mRNA for HER3 contains 28 exons and 27 introns. The fully spliced HER3 mRNA from which the introns have been spliced out is composed of 28 exons.

Two natural splice variants of HER3, p45 and p85, have been reported. Both are soluble, secreted, truncated proteins generated through alternative splicing of HER3 pre-mRNA. The mRNAs that code for each of these splice variants do not allow translation of the full-length HER3 protein, and instead generate truncated proteins. In particular, the p85 form results from the retention of Intron 13 (FIG. 12). These proteins block Heregulin-stimulated activation of HER3, HER2 and HER4, thereby inhibiting the growth of cells through the EGFR signaling pathway. Using a dominant negative truncated form of HER3 to inhibit HER2/HER3 signaling, it is possible to protect against pulmonary fibrosis (Nethery, D. E., et al., 2005, J. Appl. Physiol. 99:298).

SUMMARY OF THE INVENTION

The invention includes, in one aspect, an isolated, soluble, human epidermal growth factor receptor-2 (HER2) protein lacking the region encoded by exon 15 of the full-length mRNA transcript of the HER2 gene, and truncated, at its C terminus, in the region encoded by exon 16 of the HER2 transcript. The sequence of the protein may be, for example, one having at least 90%, preferably at least 95% sequence homology with SEQ ID No: 6 or amino acids 23-584 of SEQ ID No: 6, and the protein may be pegylated, that is, derivatized with polyethyleneglycol chains, to improve its pharmacokinetic properties, e.g., circulation time in the blood.

Also disclosed, as part of the invention, is a coding sequence for the above soluble HER2 protein. The coding sequence corresponds to a processed HER2 mRNA lacking exon 15, with exon 14 joined directly to exon 16, and may take the form of a processed HER2 mRNA, the corresponding cDNA, or a vector containing the coding sequence. An exemplary coding sequence is that having at least 80%, preferably at least 85% sequence homology to SEQ ID NO: SEQ ID NO: 5, or that portion of the sequence terminating at a stop codon within exon 16.

In another aspect, the invention includes a method of treating a female subject having an ovarian or breast cancer characterized by overexpression of human epidermal growth factor receptor-2 (HER2). The method includes the steps of (i) administering to the subject, a pharmaceutically effective amount of a soluble, human epidermal growth factor receptor-2 (HER2) protein lacking the region encoded by exon 15 of the full-length mRNA transcript of the HER2 gene, and truncated, at its C terminus, in the region encoded by exon 16 of the HER2 transcript, and (ii) continuing the administering, at periodic intervals, until a defined end point in the status of the cancer is obtained. The soluble HER2 protein employed in the method are as described above. More generally, the method may be applied to the treatment of other cell-proliferative diseases or conditions.

In still another aspect, the invention provides a splice-switching oligonucleotide compound comprising an oligonucleotide containing between 12-30 bases and at least 12 contiguous bases complementary to an exon-15 acceptor or donor splice site region contained within SEQ ID. NO: 15 of the full-length mRNA transcript of human epidermal growth factor receptor-2 (HER2) protein. The oligonucleotide may contain between 12 and 25 bases and a sequence of at least 12 contiguous bases complementary to a region contained with SEQ ID NOS: 44 or 45, both of which are contained in SEQ ID NO: 15. The oligonucleotide, may be, for example, a locked nucleic acid (LNA), 2'O-methoxyethyl oligoribonucleotide, or a phosphorodiamidate morpholino oligonucleotide. The compound may further include, conjugated to the 5'- or 3'-end of the oligonucleotide, an arginine-rich polypeptide effective to promote uptake of the compound into cells. Exemplary arginine-rich peptides include those identified by SEQ ID NOS: 52-67, and preferably those identified by SEQ ID NOS: 56-60 and 62.

In one general embodiment, the compound is composed of morpholino subunits and phosphorus-containing intersubunit linkages joining a morpholino nitrogen of one subunit to a 5' exocyclic carbon of an adjacent subunit. The morpholino subunits may be joined by phosphorodiamidate linkages having the structure:

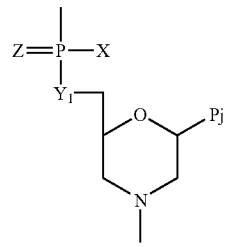

where $Y_1$=O, Z=O, Pj is a purine or pyrimidine base-pairing moiety effective to bind, by base-specific hydrogen bonding, to a base in a polynucleotide, and X is an amino or alkyl amino, including dialkylamino.

In still another aspect of the invention, there is provided a method of treating a female subject having an ovarian or breast cancer characterized by overexpression of human epidermal growth factor receptor-2 (HER2), by the steps of:

(i) administering to the subject, a pharmaceutically effective amount of a compound comprising an oligonucleotide containing between 12-30 bases and at least 12 contiguous bases complementary to an exon-15 acceptor or donor splice site region contained within SEQ ID. NO: 15 of the full-length mRNA transcript of human epidermal growth factor receptor-2 (HER2) protein, and (ii) continuing the administering, at periodic intervals, until a defined end point in the status of the cancer is obtained. The oligonucleotide compound employed in the method may have the features noted above. More generally, the method may be applied to the treatment of other cell-proliferative diseases or conditions.

The method may further include administering to the subject, a pharmaceutically effective amount of a soluble, human epidermal growth factor receptor-2 (HER2) protein lacking the region encoded by exon 15 of the full-length mRNA transcript of the HER2 gene, and truncated, at its C terminus, in the region encoded by exon 16 of the HER2 transcript.

In still another aspect, the invention includes an isolated, soluble, human epidermal growth factor receptor-3 (HER3)

protein lacking the region encoding by one of (i) exon 13 of the full-length mRNA transcript of the HER3 gene, and truncated, at its C terminus, in the region encoded by exon 15 of the HER3 transcript, (ii) exon 14 of the full-length mRNA transcript of the HER3 gene, and truncated, at its C terminus, in the region encoded by exon 15 of the HER3 transcript, or (iii) exon 15 of the full-length mRNA transcript of the HER3 gene, and truncated, at its C terminus, in the region encoded by exon 16 of the HER3 transcript. The protein may have a sequence that is at least 90%, preferably at least 95% homologous to one of (i) SEQ ID No: 8 or amino acids 20-541 of SEQ ID No:8, (ii) SEQ ID No: 10 or amino acids 20-555 of SEQ ID No:10, or (iii) SEQ ID NO: 12 or amino acids 20-569 of SEQ ID No:12. The soluble HER3 protein may be pegylated, that is, derivatized with polyethyleneglycol chains, to improve its pharmacokinetic properties, e.g., circulation time in the blood.

Also disclosed, as part of the invention, is a coding sequence for the above soluble HER3 protein. The coding sequence corresponds to a processed HER3 mRNA (i) lacking exon 13, with exon 12 joined directly to exon 14, (ii) (i) lacking exon 14, with exon 13 joined directly to exon 15, or (iii) lacking exon 15, with exon 14 joined directly to exon 16, and may take the form of a processed HER3 mRNA, the corresponding cDNA, or a vector containing the coding sequence. Exemplary coding sequences are those having at least 80%, preferably at least 85% sequence homology to SEQ ID NOS: 7, 9, or 11, or that portion of the sequence terminating at a stop codon within exon 15 (for SEQ ID NOS: 7 and 9), or a stop codon within exon 16 (for SEQ ID NO:11).

In another aspect, the invention includes a method of treating a female subject having an ovarian or breast cancer characterized by overexpression of human epidermal growth factor receptor-2 (HER2). The method includes the steps of (i) administering to the subject, a pharmaceutically effective amount of soluble, human epidermal growth factor receptor-3 (HER3) protein lacking the region encoding by one of (i) exon 13 of the full-length mRNA transcript of the HER3 gene, and truncated, at its C terminus, in the region encoded by exon 15 of the HER3 transcript, (ii) exon 14 of the full-length mRNA transcript of the HER3 gene, and truncated, at its C terminus, in the region encoded by exon 15 of the HER3 transcript, or (iii) exon 15 of the full-length mRNA transcript of the HER3 gene, and truncated, at its C terminus, in the region encoded by exon 16 of the HER3 transcript, and (ii) continuing the administering, at periodic intervals, until a defined end point in the status of the cancer is obtained. The soluble HER2 protein employed in the method are as described above. More generally, the method may be applied to the treatment of other cell-proliferative diseases or conditions.

In still another aspect, the invention provides a splice-switching oligonucleotide compound comprising an oligonucleotide containing between 12-30 bases and at least 12 contiguous bases complementary to one of (i) an exon-13 acceptor or donor splice site region contained within SEQ ID. NO: 16 of the full-length mRNA transcript of human epidermal growth factor receptor-3 (HER3) protein; (ii) an exon-13 acceptor or donor splice site region contained within SEQ ID. NO: 16 of the full-length mRNA transcript of human epidermal growth factor receptor-3 (HER3) protein; or (iii) an exon-15 acceptor or donor splice site region contained within SEQ ID. NO: 16 of the full-length mRNA transcript of human epidermal growth factor receptor-3 (HER3) protein. The oligonucleotide may contain between 12 and 25 bases and a sequence of at least 12 contiguous bases complementary to a region contained within one or SEQ ID NOS: 46-51, all of which are contained in SEQ ID NO: 16. The oligonucleotide, may be, for example, a locked nucleic acid (LNA), 2'-O-methoxyethyl oligoribonucleotide or a phosphorodiamidate morpholino oligonucleotide (PMO). The compound may further include, conjugated to the 5'- or 3'-end of the oligonucleotide, an arginine-rich polypeptide effective to promote uptake of the compound into cells. Exemplary arginine-rich peptides include those identified by SEQ ID NOS: 52-67, and preferably those identified by SEQ ID NOS: 56-60 and 62.

In one general embodiment, the compound is composed of morpholino subunits and phosphorus-containing intersubunit linkages joining a morpholino nitrogen of one subunit to a 5' exocyclic carbon of an adjacent subunit. The morpholino subunits may be joined by phosphorodiamidate linkages having the structure:

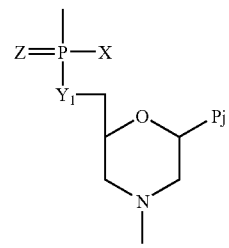

where $Y_1$=O, Z=O, Pj is a purine or pyrimidine base-pairing moiety effective to bind, by base-specific hydrogen bonding, to a base in a polynucleotide, and X is an amino or alkyl amino, including dialkylamino.

In still another aspect of the invention, there is provided a method of treating a female subject having an ovarian or breast cancer characterized by overexpression of human epidermal growth factor receptor-3 (HER3), by the steps of:

(i) administering to the subject, a pharmaceutically effective amount of a compound comprising an oligonucleotide containing between 12-30 bases and at (i) administering to the subject, a pharmaceutically effective amount of a compound comprising an oligonucleotide containing between 12-30 bases and at least 12 contiguous bases complementary to one of (i) an exon-13 acceptor or donor splice site region contained within SEQ ID. NO: 16 of the full-length mRNA transcript of human epidermal growth factor receptor-3 (HER3) protein; (ii) an exon-13 acceptor or donor splice site region contained within SEQ ID. NO: 16 of the full-length mRNA transcript of human epidermal growth factor receptor-3 (HER3) protein; or (iii) an exon-15 acceptor or donor splice site region contained within SEQ ID. NO: 16 of the full-length mRNA transcript of human epidermal growth factor receptor-3 (HER3) protein, and (ii) continuing the administering, at periodic intervals, until a defined end point in the status of the cancer is obtained. The oligonucleotide compound employed in the method may have the features noted above. More generally, the method may be applied to the treatment of other cell-proliferative diseases or conditions.

The method may further include administering to the subject, a pharmaceutically effective amount of a soluble human epidermal growth factor receptor-2 (HER2) protein lacking the region encoding by exon 15 of the full-length mRNA transcript of the HER2 gene, and truncated, at its C terminus, in the region encoded by exon 16 of the HER2 transcript.

These and other and features of the invention will become more fully apparent when the following detailed description of the invention is read in conjunction with the accompanying drawings.

BRIEF DESCRIPTION OF THE DRAWINGS

FIG. 11: The sequence of a portion of the human HER2 gene is presented (SEQ ID NOS: 15 and 70). The sequence shown is from the middle of intron 14 through a portion of exon 16. Exon sequences are underlined and in bold. The stop codon in exon 16 for the Δ15HER2 protein is boxed.

FIG. 12: The sequence of a portion of the human HER3 gene is presented (SEQ ID NOS: 16 and 71). The sequence shown is from the middle of intron 12 through a portion of exon 16. Exon sequences are underlined and in bold.

DETAILED DESCRIPTION OF THE DRAWINGS

I Definitions

Figure 1:
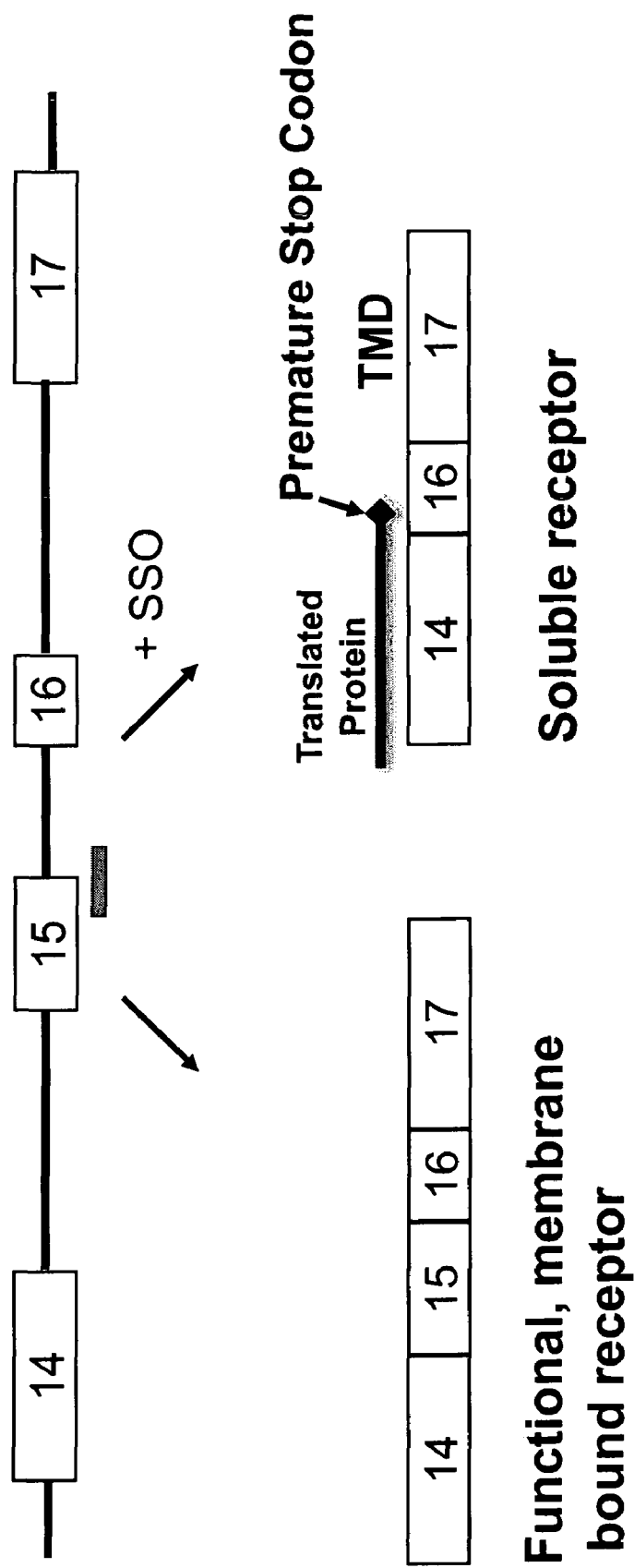
FIG. 1: Oligonucleotides (bars) directed toward exon 15 elicit the induction of a novel HER2 mRNA that lacks exon 15, such that downstream exons, including exon 16 which encodes the transmembrane domain, have an improper reading frame that introduces a stop codon in the exon, as indicated.

As used herein, the terms "epidermal growth factor receptor", "EGF receptor", and "EGFR" refer to proteins having amino acid sequences of or which are substantially similar to native mammalian epidermal growth factor receptor family sequences, preferably HER1, HER2, HER3 and HER4. In this context, a "native" receptor or gene for such a receptor, means a full-length receptor or gene that occurs in nature, as well as the naturally-occurring allelic variations of such receptors and genes.

As used herein, the terms "soluble epidermal growth factor receptor", "soluble EGF receptor", and "sEGFR" refer to soluble proteins whose sequences are or are substantially similar to those encoded by an mRNA derived from a native EGFR mRNA where a single exon has been skipped or a single intron has been retained during splicing.

The term "mature" as used in connection with a protein means a protein expressed in a form lacking a leader or signal sequence as may be encoded in full-length transcripts of a native gene.

The terms "secreted" and "soluble" are used interchangeably herein and mean that the protein is soluble, i.e., that it is not bound to the cell membrane. In this context, a form will be soluble if, using conventional assays known to one of skill in the art, most of this form can be detected in fractions that are not associated with the membrane, e.g., in cellular supernatants from lysed or intact cells or in serum.

The term "stable" means that the sEGFR is detectable using conventional assays known to one of skill in the art, such as for example, western blots or ELISA assays of harvested cells, cellular supernatants, or serum.

As used herein, the term "a cell-proliferative disease or condition" refers to a disease, disorder, or other medical condition that, at least in part, results from or is aggravated by either an increase in cell division or cell survival or a decrease in apoptosis. Such diseases or conditions include, but are not limited to, those associated with increased levels of EGFR ligands, increased levels of EGF receptors, or increased sensitization or deregulation of an EGFR signaling pathway, and in particular, increased levels of HER2 and/or HER3. The term also encompasses diseases and conditions for which known EGFR antagonists have been shown useful. Examples of proliferative diseases or conditions include, but are not limited to, cancer and pulmonary fibrosis. Psoriasis (Wierzbicka, E., et al., 2006, Brit. J. of Dermatol., 155: 207-229) and diabetic retinopathy (Xu, K. P., 2007, Investig. Opthal. and Visual Sci., 48: 2242-2248) can also be treated with HER2 antagonists.

As used herein, the term "HER2 antagonist" means that the protein is capable of causing a measurable increase in cytotoxicity in HER2 expressing cells, either by directly antagonizing HER2 function or by binding and inactivating EGFR ligands such as heregulin, using standard assays as are well known in the art. (See, e.g., the cell viability assay in the examples herein).

As used herein, the term "induce apoptosis" means to cause cell death by apoptosis. Induction of apoptosis can be measured using conventional assays know to one of skill in the art. These assays include but are not limited to: i) Annexin V-FITC staining (Invitrogen) and FACS, which can detect phosphatidylserine displayed on the surface of cells undergoing apoptotic death; ii) ApoAlert® CPP32 colorimetric assay (Clontech), which detects CPP32 protease activity, a key early event in apoptosis; and iii) Western blot for specific intracellular proteins, such as poly(ADP ribose) polymerase (PARP) and cyclin B, which are degraded by caspases during apoptosis (See, e.g., the PARP cleavage assay in the examples herein).

As used herein, the terms "transformation" or "transfection" refer to the insertion of an exogenous nucleic acid into a cell, irrespective of the method used for the insertion, for example, lipofection, transduction, infection or electroporation. The exogenous nucleic acid can be maintained as a non-integrated vector, for example, a plasmid, or alternatively, can be integrated into the cell's genome.

As used herein, the term "vector" refers to a nucleic acid molecule capable of transporting into a cell another nucleic acid to which it has been linked As used herein, the term "isolated protein" refers to a protein or polypeptide that is not naturally-occurring and is separated from one or more components that are associated with it at its synthesis or is naturally-occurring and is separated from one or more components that are naturally associated with it.

As used herein, the term "isolated nucleic acid" refers to a nucleic acid that is in the form of a separate fragment or as a component of a larger construct, which has been derived from a nucleic acid isolated at least once in substantially pure form, i.e., free of contaminating endogenous materials, and in a quantity or concentration enabling identification and manipulation by standard biochemical methods, for example, using a cloning vector.

As used herein the term "purified protein" refers to a protein that is present in the substantial absence of other proteins. However, such purified proteins can contain other proteins added as stabilizers, carriers, excipients, or co-therapeutics. The term "purified" as used herein preferably means at least 80% by dry weight, more preferably in the range of 95-99% by weight, and most preferably at least 99.8% by weight, of protein present, excluding proteins added as stabilizers, carriers, excipients, or co-therapeutics.

As used herein, the term "altering the splicing of a pre-mRNA" refers to altering the splicing of a cellular pre-mRNA target resulting in an altered ratio of spliced products. Such an alteration of splicing can be detected by a variety of techniques well known to one of skill in the art. For example, RT-PCR can be used on total cellular RNA to detect the ratio of splice products in the presence and the absence of an SSO.

As used herein, the term "complementary" is used to indicate a sufficient degree of complementarity or precise pairing such that stable and specific binding occurs between an oligonucleotide and a DNA or RNA containing the target sequence. It is understood in the art that the sequence of an oligonucleotide need not be 100% complementary to that of its target. For example, for an SSO there is a sufficient degree of complementarity when, under conditions which permit splicing, binding to the target will occur and non-specific binding will be substantially avoided.

As used here, a protein or nucleic acid has at least a specified percentage of sequence homology with a given SEQ ID NO, if the protein or nucleic acid in question has the same amino acid residues or bases, in the same sequence, in at least the specified percentage of residues or bases of the identified SEQ ID NO. In making nucleic acids with at least a given degree of sequence homology to a specified coding sequence, one skilled in the art, with the aid of a computer, could readily generate all nucleic acid sequences that would encode a given protein sequence. In making proteins with at least a given degree of sequence homology to specified protein sequence, one skilled in the art, guided by a knowledge of the physicochemical properties of amino acids, the position of a given residue within a protein, the known effects of certain amino acids on the conformation of proteins, and with the aid of a computer, could readily select certain amino acid substitutions at certain residue positions that would, with reasonable predictability, preserve the functional properties of the protein.

IIA. Splice Variant Her2 and Her3 Proteins

One embodiment of the present invention is a protein, either full length or mature, which is encoded by a cDNA derived from a native epidermal growth factor receptor (EGFR) gene, particularly either HER2 or HER3, where a single exon in the cDNA is skipped resulting in a soluble protein (sEGFR). Furthermore the sEGFR can act as an EGFR, preferably HER2, antagonist. "Mammalian sEGFR", according to the present invention, includes but is not limited to soluble human, primate, murine, canine, feline, bovine, ovine, equine, and porcine EGFR. Furthermore, mammalian sEGFR according to the present invention includes, but is not limited to, a protein sequence that results from one or more single nucleotide polymorphisms, as long as the protein retains a comparable biological activity to the reference sEGFR with which it is being compared.

In one embodiment, the soluble mammalian EGFR is a mammalian HER2, preferably a human HER2. In particular, in the cDNA for this protein exon 14 is followed directly by exon 16 and as a result exon 15 is skipped (FIG. 11). For soluble human HER2, two non-limiting examples of this embodiment are given by Δ15HER2 that includes the signal sequence as shown in SEQ ID No: 6 and mature Δ15HER2 (amino acids 23-584 of SEQ ID No: 6) that lacks the signal sequence.

In another embodiment, the soluble mammalian EGFR is a mammalian HER3, preferably a human HER3. In one aspect of this embodiment, exon 12 is followed directly by exon 14 and as a result exon 13 is skipped (FIG. 12). For soluble human HER3, two non-limiting examples of this embodiment are given by Δ13HER3 that includes the signal sequence as shown in SEQ ID No: 8 and mature Δ13HER3 (amino acids 20-541 of SEQ ID No: 8) that lacks the signal sequence. In another aspect, exon 13 is followed directly by exon 15 and as a result exon 14 is skipped (FIG. 12). For soluble human HER3, two non-limiting examples of this embodiment are given by Δ14HER3 that includes the signal sequence as shown in SEQ ID No: 10 and mature Δ14HER3 (amino acids 20-555 of SEQ ID No: 10) that lacks the signal sequence. In yet another aspect, exon 14 is followed directly by exon 16 and as a result exon 15 is skipped (FIG. 12). For soluble human HER3, two non-limiting examples of this embodiment are given by Δ15HER3 that includes the signal sequence as shown in SEQ ID No: 12 and mature Δ115HER3 (amino acids 20-569 of SEQ ID No: 12) that lacks the signal sequence.

The proteins of the present invention also include those proteins that are chemically modified. Chemical modification of a protein refers to a protein where at least one of its amino acid residues is modified by either natural processes, such as processing or other post-translational modifications, or by chemical modification techniques known in the art. Such modifications include, but are not limited to, acetylation, acylation, amidation, ADP-ribosylation, glycosylation, methylation, pegylation, prenylation, phosphorylation, or cholesterol conjugation.

IIB. Protein Expression and Purification

When mammalian or insect cells are used, properly expressed sEGFR will be secreted into the extracellular media. The protein is recovered from the media, and is concentrated and purified using standard biochemical techniques. After expression in mammalian cells by lentiviral or AAV transduction, plasmid transfection, or any similar procedure, or in insect cells after baculoviral transduction, the extracellular media of these cells is concentrated using concentration filters with an appropriate molecular weight cutoff, such as Amicon® filtration units.

When sEGFR is expressed in bacterial culture it can be purified by standard biochemical techniques. Bacteria are lysed, and the cellular extract containing the sEGFR is desalted and concentrated.

In either case, the sEGFR can be purified by affinity chromatography. The use of column chromatography with an affinity matrix comprising an EGFR ligand can be used to purify HER3 splice variants. Alternatively, an affinity purification tag can be added to either the N- or the C-terminus of the sEGFR. For example, a polyhistidine-tag (His-tag), which is an amino acid motif with at least six histidines, can be used for this purpose (Hengen, P., 1995, Trends Biochem. Sci. 20:285-86). The addition of a His-tag can be achieved by the in-frame addition of a nucleotide sequence encoding the His-tag directly to either the 5' or 3' end of the sEGFR open reading frame in an expression vector. When a His-tag is incorporated into the protein, a nickel or cobalt affinity column is employed to purify the tagged sEGFR, and the His-tag can optionally then be cleaved. Other suitable affinity purification tags and methods of purification of proteins with those tags are well known in the art.

Alternatively, a non-affinity based purification scheme can be used, involving fractionation of the sEGFR extracts on a series of columns that separate the proteins based on size (size exclusion chromatography), charge (anion and cation exchange chromatography) and hydrophobicity (reverse phase chromatography). High performance liquid chromatography can be used to facilitate these steps.

IIC. Use of Proteins for the Treatment of Proliferative Diseases

For therapeutic use, sEGFR of the present invention is administered to a patient, preferably a human, for treating HER2-dependent proliferative diseases, such as cancer. In the treatment of humans, the use of soluble human EGFR is preferred. The sEGFR of the present invention can be administered by bolus injection, continuous infusion, sustained release from implants, or other suitable techniques. Typically, therapeutic sEGFR will be administered in the form of a composition comprising purified protein in conjunction with physiologically acceptable carriers, excipients or diluents. Such carriers will be nontoxic to recipients at the dosages and concentrations employed. Ordinarily, the preparation of such compositions entails combining the sEGFR with buffers, antioxidants such as ascorbic acid, polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product is formulated as a lyophilizate using appropriate excipient solutions, for example, sucrose, as diluents. Preservatives, such as benzyl alcohol can also be added. The amount and frequency of administration will depend of course, on such factors as the nature and the severity of the indication being treated, the desired response, the condition of the patient and so forth.

sEGFR of the present invention is administered systemically in therapeutically effective amounts preferably ranging from about 0.1 mg/kg/week to about 100 mg/kg/week. In preferred embodiments, sEGFR is administered in amounts ranging from about 0.5 mg/kg/week to about 50 mg/kg/week. For local administration, dosages preferably range from about 0.01 mg/kg to about 1.0 mg/kg per injection.

IID. Treatment Methods Using the Splice Variant Proteins

The present invention provides for the use of proteins as set forth above for the preparation of a medicament for treating a patient afflicted with a proliferative disorder involving excessive EGFR, preferably HER2, activity, as discussed below. In the manufacture of a medicament according to the present invention, the proteins of the present invention are typically admixed with, inter alia, an acceptable carrier. The carrier must, of course, be acceptable in the sense of being compatible with other ingredients in the formulation and must not be deleterious to the patient. The carrier can be a solid or liquid. The proteins of the present invention are incorporated in formulations, which can be prepared by any of the well known techniques of pharmacy consisting essentially of admixing the components, optionally including one or more accessory therapeutic ingredients.

Formulations of the present invention can comprise sterile aqueous and non-aqueous injection solutions of the active compounds, which preparations are preferably isotonic with the blood of the intended recipient and essentially pyrogen free. These preparations can contain anti-oxidants, buffers, bacteriostats, and solutes which render the formulation isotonic with the blood of the intended recipient. Aqueous and non-aqueous sterile suspensions can include, but are not limited to, suspending agents and thickening agents. The formulations can be presented in unit dose or multi-dose containers, for example, sealed ampoules and vials, and can be stored in freeze-dried (lyophilized) condition requiring only the addition of the sterile liquid carrier, for example, saline or water-for-injection immediately prior to use.

In the formulations, the nucleic acids and proteins of the present invention can be contained within a particle or vesicle, such as a liposome or microcrystal, which can be suitable for parenteral administration. The particles can be of any suitable structure, such as dendritic, hyper-branched, unilamellar or plurilameller, so long as the nucleic acids and proteins of the present invention are contained therein. Positively charged lipids such as N-[1-(2,3-dioleoyloxy)propyl]-N,N,N-trimethyl-ammoniummethylsulfate, or "DOTAP," are particularly preferred for such particles and vesicles. The preparation of such lipid particles is well known (See references in U.S. Pat. No. 5,976,879 col. 6).

IIIA. Splice Variant Nucleic Acids

One embodiment of the present invention is a nucleic acid that encodes a protein, either full length or mature, which is encoded by a cDNA derived from an epidermal growth factor receptor (EGFR) gene, particularly either HER2 or HER3, where a single exon in the cDNA is skipped resulting in a soluble protein. Furthermore the encoded protein can act as an HER2 antagonist.

Such sequences are preferably provided in the form of an open reading frame uninterrupted by internal nontranslated sequences, or introns, which are typically present in eukaryotic genes. Genomic DNA containing the relevant sequences can also be used. In one embodiment, the nucleic acid is either an mRNA or a cDNA. In another embodiment, it is genomic DNA.

In one embodiment, the soluble mammalian EGFR is a mammalian HER2, preferably a human HER2. For soluble human HER2, two non-limiting examples of this embodiment are nucleic acids that encode the Δ15HER2 that includes the signal sequence as shown in SEQ ID No: 6 and mature Δ15HER2 (amino acids 23-584 of SEQ ID No: 6) that lacks the signal sequence. Examples of the sequences of these Δ15HER2 nucleic acids are, without limitation, nucleotides 1-1752 of SEQ ID No: 5, which includes the signal sequence and nucleotides 67-1752 of SEQ ID No: 5, which lacks the signal sequence.

In another embodiment, the soluble mammalian EGFR is a mammalian HER3, preferably a human HER3. For soluble human HER3, two non-limiting examples of this embodiment are nucleic acids that encode the Δ13HER3 that includes the signal sequence as shown in SEQ ID No: 8 or mature Δ13HER3 (amino acids 20-541 of SEQ ID No: 8) that lacks the signal sequence. Examples of the sequences of these Δ13HER3 nucleic acids are, without limitation, nucleotides 1-1623 of SEQ ID No: 7, which includes the signal sequence and nucleotides 58-1623 of SEQ ID No: 7, which lacks the signal sequence.

For soluble human HER3, two further non-limiting examples of this embodiment are nucleic acids that encode the Δ4HER3 that includes the signal sequence as shown in SEQ ID No: 10 or mature Δ14HER3 (amino acids 20-555 of SEQ ID No: 10) that lacks the signal sequence. Examples of the sequences of these Δ14HER3 nucleic acids are, without limitation, nucleotides 1-1665 of SEQ ID No: 9, which includes the signal sequence and nucleotides 58-1665 of SEQ ID No: 9, which lacks the signal sequence.

For soluble human HER3, two other non-limiting examples of this embodiment are nucleic acids that encode the Δ15HER3 that includes the signal sequence as shown in SEQ ID No: 12 or mature Δ115HER3 (amino acids 20-569 of SEQ ID No: 12) that lacks the signal sequence. Examples of the sequences of these Δ15HER3 nucleic acids are, without limitation, nucleotides 1-1707 of SEQ ID No: 11, which includes the signal sequence and nucleotides 58-1707 of SEQ ID No: 11, which lacks the signal sequence.

The bases of the nucleic acids of the present invention can be the conventional bases cytosine, guanine, adenine and uracil or thymidine. Optionally, modified bases can be used.

Suitable nucleic acids of the present invention include numerous alternative chemistries. For example, suitable nucleic acids of the present invention include, but are not limited to, those wherein at least one of the internucleotide bridging phosphate residues is a modified phosphate, such as phosphorothioate, methyl phosphonate, methyl phosphonothioate, phosphoromorpholidate, phosphoropiperazidate, and phosphoroamidate.

Nucleic acids of the present invention also include, but are not limited to, those wherein at least one, of the nucleotides is a nucleic acid analogue.

Nucleic acids of the present invention include, but are not limited to, modifications of the nucleic acids involving chemically linking to the nucleic acids one or more moieties or conjugates. Such moieties include, but are not limited to, lipid moieties such as a cholesterol moiety, cholic acid, a thioether, e.g. hexyl-5-tritylthiol, a thiocholesterol, an aliphatic chain, e.g., dodecandiol or undecyl residues, a phospholipids, e.g., di-hexadecyl-rac-glycerol or triethylammonium 1,2-di-O-hexadecyl-rac-glycero-3-H-phosphonate, a polyamine or a polyethylene glycol chain, an adamantane acetic acid, a palmityl moiety, an octadecylamine or hexylamino-carbonyl-oxycholesterol moiety.

IIIB. Expression and Gene-Therapy Vectors

The present invention also provides expression vectors to amplify or express DNA encoding the foregoing proteins of the current invention, as well as host cells transformed with the foregoing expression vectors. Expression vectors are replicable DNA constructs which have synthetic or cDNA-derived DNA fragments encoding soluble mammalian EGFR, particularly HER2 or HER3, or bioequivalent analogues operably linked to suitable transcriptional or translational regulatory elements derived from mammalian, microbial, viral, or insect genes. A transcriptional unit generally comprises an assembly of (a) a genetic element or elements having a regulatory role in gene expression, such as, transcriptional promoters or enhancers, (b) a structural or coding sequence which is transcribed into mRNA and translated into protein, and (c) appropriate transcription and translation initiation and termination sequences. Such regulatory elements can include an operator sequence to control transcription, and a sequence encoding suitable mRNA ribosomal binding sites. The ability to replicate in a host, usually conferred by an origin of replication, and a selection gene to facilitate recognition of transformants, can additionally be incorporated.

DNA regions are operably linked when they are functionally related to each other. For example, DNA for a signal peptide (secretory leader) is operably linked to DNA for a polypeptide if it is expressed as part of a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame. Structural elements intended for use in yeast expression systems preferably include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed protein to provide a final product.

Soluble mammalian EGFR DNA is expressed or amplified in a recombinant expression system comprising a substantially homogeneous monoculture of suitable host microorganisms, for example, bacteria such as *E. coli* or yeast such as *S. cerevisiae*, which have stably integrated (by transformation or transfection) a recombinant transcriptional unit into chromosomal DNA or which carry the recombinant transcriptional unit as a component of a resident plasmid. Recombinant expression systems as defined herein will express heterologous protein either constitutively or upon induction of the regulatory elements linked to the DNA sequence or synthetic gene to be expressed.

Transformed host cells are cells which have been transformed or transfected with soluble mammalian EGFR vectors constructed using recombinant DNA techniques. Transformed host cells ordinarily express sEGFR, but host cells transformed for purposes of cloning or amplifying sEGFR DNA do not need to express sEGFR. Suitable host cells for expression of soluble mammalian EGFR include prokaryotes, yeast, fungi, or higher eukaryotic cells. Prokaryotes include gram negative or gram positive organisms, for example *E. coli* or bacilli. Higher eukaryotic cells include, but are not limited to, established insect and mammalian cell lines. Cell-free translation systems can also be employed to produce soluble mammalian EGFR using RNAs derived from the DNA constructs of the present invention. Appropriate cloning and expression vectors for use with bacterial, fungal, yeast, and mammalian cellular hosts are well known in the art.

Prokaryotic expression hosts can be useful for expression of sEGFR that does not undergo extensive posttranslational processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera *Pseudomonas, Streptomyces*, and *Staphylococcus*, although others can also be employed as a matter of choice.

Useful expression vectors for bacterial use can comprise a selectable marker and bacterial origin of replication derived from commercially available plasmids comprising genetic elements of the well known cloning vector pBR322 (ATCC 37017). These pBR322 "backbone" sections are combined with an appropriate promoter and the structural sequence to be expressed. pBR322 contains genes for ampicillin and tetracycline resistance and thus provides simple means for identifying transformed cells. Such commercial vectors include, for example, the series of Novagen® pET vectors (EMD Biosciences, Inc., Madison, Wis.).

Promoters commonly used in recombinant microbial expression vectors include the lactose promoter system, and the $\lambda$ $P_L$ promoter, the T7 promoter, and the T7 lac promoter. A particularly useful bacterial expression system, Novagen® pET system (EMD Biosciences, Inc., Madison, Wis.) employs a T7 or T7 lac promoter and *E. coli* strain, such as BL21 (DE3) which contain a chromosomal copy of the T7 RNA polymerase gene.

sEGFR proteins can also be expressed in yeast and fungal hosts, preferably from the genus *Saccharomyces*, such as *S. cerevisiae*. Yeast of other genera, such as *Pichia* or *Kluyveromyces* can also be employed. Yeast vectors will generally contain an origin of replication from the 2μ yeast plasmid or an autonomously replicating sequence (ARS), promoter, DNA encoding sEGFR, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and *S. cerevisiae* TRP1 or URA3 gene, which provides a selection marker for a mutant strain of yeast lacking the ability to grow in tryptophan or uracil, respectively, and a promoter derived from a highly expressed yeast gene to induce transcription of a structural sequence downstream. The presence of the TRP1 or URA3 lesion in the yeast host cell genome then provides an effective environment for detecting transformation by growth in the absence of tryptophan or uracil, respectively.

Suitable promoter sequences in yeast vectors include the promoters for metallothionein, 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are well known in the art.

Preferred yeast vectors can be assembled using DNA sequences from pUC18 for selection and replication in *E. coli* (Amp$^r$ gene and origin of replication) and yeast DNA sequences including a glucose-repressible ADH2 promoter and α-factor secretion leader. The yeast α-factor leader, which directs secretion of heterologous proteins, can be inserted between the promoter and the structural gene to be expressed. The leader sequence can be modified to contain, near its 3' end, one or more useful restriction sites to facilitate fusion of the leader sequence to foreign genes. Suitable yeast transformation protocols are known to those of skill in the art.

Host strains transformed by vectors comprising the ADH2 promoter can be grown for expression in a rich medium consisting of 1% yeast extract, 2% peptone, and 1% or 4% glucose supplemented with 80 □g/ml adenine and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems are also advantageously employed to express sEGFR protein. Expression of recombinant proteins in mammalian cells is particularly preferred because such proteins are generally correctly folded, appropriately modified and completely functional. Examples of suitable mammalian host cell lines include the COS-7 lines of monkey kidney cells, and other cell lines capable of expressing an appropriate vector including, for example, L cells, such as L929, C127, 3T3, Chinese hamster ovary (CHO), HeLa and BHK cell lines. Mammalian expression vectors can comprise nontranscribed elements such as an origin of replication, a suitable promoter, for example, the CMVie promoter, the chicken beta-actin promoter, or the composite hEF1-HTLV promoter, and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are known to those of skill in the art.

The transcriptional and translational control sequences in expression vectors to be used in transforming vertebrate cells can be provided by viral sources. For example, commonly used promoters and enhancers are derived from Polyoma, Adenovirus 2, Simian Virus 40 (SV40), human cytomegalovirus, such as the CMVie promoter, HTLV, such as the composite hEF1-HTLV promoter. DNA sequences derived from the SV40 viral genome, for example, SV40 origin, early and late promoter, enhancer, splice, and polyadenylation sites can be used to provide the other genetic elements required for expression of a heterologous DNA sequence.

Further, mammalian genomic EGFR promoters, such as control and/or signal sequences can be utilized, provided such control sequences are compatible with the host cell chosen.

In preferred aspects of the present invention, recombinant expression vectors comprising sEGFR cDNAs are stably integrated into a host cell's DNA.

One embodiment is a method of treating a proliferative disease or condition by administering sEGFR to a subject, thereby decreasing HER2 activity. Another embodiment is a method of treating a proliferative disease or condition by administering to a subject an expression vector that encodes sEGFR, thereby decreasing HER2 activity. Another embodiment is a method of producing sEGFR.

The following aspects of the present invention apply to the foregoing embodiments.

The methods, nucleic acids, proteins, and formulations of the present invention are also useful as in vitro or in vivo tools.

In further embodiments, apoptosis in mammalian cells can be induced by administering to the mammalian cells, in an amount and under conditions sufficient to induce apoptosis, nucleic acids, proteins, and formulations of the present invention.

Embodiments of the invention can be used to treat any condition in which the medical practitioner intends to limit the effect of a signaling pathway involving EGFR. In particular, the formulations of the present invention can be used to treat a proliferative disease. Such diseases include, but are not limited to cancer and pulmonary fibrosis. In one embodiment, the condition is a cancer selected from the group consisting of breast, lung, ovarian, gastric and colon cancer. In one embodiment, the condition is a cancer which is resistant to chemotherapy. The uses of the present invention include, but are not limited to, treatment of diseases for which known HER2 antagonists, such as Herceptin, Herstatin and pertuzumab, have been shown useful.

IIIC. Use of Expression Vectors to Increase the Levels of an HER2 Antagonist in a Mammal The present invention provides a process of increasing the levels of an HER2 antagonist in a mammal. The process includes the step of transforming cells of the mammal with an expression vector described herein, which drives expression of sEGFR as described herein.

The process is particularly useful in large mammals such as domestic pets, those used for food production, and primates. Exemplary large mammals are dogs, cats, horses cows, sheep, deer, and pigs. Exemplary primates are monkeys, apes, and humans.

The mammalian cells can be transformed either in vivo or ex vivo. When transformed in vivo, the expression vector is administered directly to the mammal, such as by injection. Means for transforming cells in vivo are well known in the art. When transformed ex vivo, cells are removed from the mammal, transformed ex vivo, and the transformed cells are reimplanted into the mammal.

IV. Pharmaceutical Compositions and Preparations

Other embodiments of the present invention are pharmaceutical compositions comprising the foregoing proteins or nucleic acids.

The nucleic acids or proteins of the present invention can be admixed, encapsulated, conjugated, or otherwise associated with other molecules, molecule structures, or mixtures of compounds, as for example liposomes, and receptor targeted molecules, in oral, rectal, topical or other formulations, for assisting in uptake, distribution, and/or absorption.

Formulations of the present invention comprise nucleic acids or proteins in a physiologically or pharmaceutically acceptable carrier, such as an aqueous carrier. Thus formulations for use according to the present invention include, but are not limited to, those suitable for parenteral administration including intraperitoneal, intravenous, intraarterial, subcutaneous, intraarticular, or intramuscular injection or infusion, as well as those suitable for topical, ophthalmic, vaginal, oral, rectal or pulmonary administration (including inhalation or insufflation of powders or aerosols, including by nebulizer, intratracheal, and intranasal delivery). The formulations can conveniently be presented in unit dosage form and can be prepared by any of the methods well known in the art. The most suitable route of administration in any given case can depend upon the subject, the nature and severity of the condition being treated, and the particular active compound which is being used.

Pharmaceutical compositions of the present invention include, but are not limited to, physiologically and pharmaceutically acceptable salts, i.e., salts that retain the desired biological activity of the parent compound and do not impart undesired toxicological properties. Examples of such salts are (a) salts formed with cations such as sodium, potassium, $NH_4^+$, magnesium, calcium, polyamines such as spermine and spermidine; (b) acid addition salts formed with inorganic acids, for example, hydrochloric acid, hydrobromic acid, sulfuric acid, phosphoric acid, nitric acid and the like; and (c) salts formed with organic acids such as, for example, acetic acid, oxalic acid, tartaric acid, succinic acid, maleic acid, fumaric acid, gluconic acid, citric acid, malic acid, ascorbic acid, benzoic acid, palmitic acid, alginic acid, polyglutamic acid, napthalenesulfonic acid, methanesulfonic acid, p-toluenesulfonic acid, napthalenedisulfonic acid, polygalacturonic acid, and the like.

V. Splice-Switching Oligomers (SSOs)

In another aspect, the present invention employs splice switching oligonucleotides or splice switching oligomers (SSOs) to control the alternative splicing of either HER2 or HER3 so that the amount of a soluble form is increased, and optionally the amount of the integral membrane form is decreased. The methods and compositions of the present invention can be used in the treatment of diseases associated with excessive HER2 activity.

Accordingly, one embodiment of the present invention is a method of treating a proliferative disease or condition by administering SSOs to a patient. The SSOs that are administered alter the splicing of a pre-mRNA to produce a soluble form of either HER2 or HER3. In one embodiment, the soluble form is Δ15HER2. In another embodiment, the soluble form is Δ13HER3. In yet another embodiment, the soluble form is Δ14HER3. In yet a further embodiment, the soluble form is Δ15HER3. In another embodiment, the soluble form is the p85 form of HER3.

In another embodiment, a method of producing a soluble form of either HER2 or HER3 in a cell by administering SSOs to the cell is disclosed. In yet another embodiment, a method of inducing apoptosis in mammalian cells by administering SSOs to the mammalian cell is disclosed.

The length of the SSO (i.e., the number of monomers in the oligomer) is similar to an antisense oligonucleotide (ASON), typically between about 8 and 30 nucleotides. In preferred embodiments, the SSO will be between about 10 to 30, more preferably 15 to 25, nucleotides. In this aspect, the invention can be practiced with SSOs comprised of several chemistries that hybridize to RNA, but that do not activate the destruction of the target RNA by RNase H, as do conventional antisense 2'-deoxy oligonucleotides. The invention can be practiced using 2'O modified nucleic acid oligomers, such as where the 2'O is replaced with $-O-CH_3$, $-O-CH_2-CH_2-O-CH_3$, $-O-CH_2-CH_2-CH_2-NH_2$, $-O-CH_2-CH_2-CH_2-OH$ or $-F$, where 2'O-methyl (2'-OMe) or 2'O-methyloxyethyl (MOE) is preferred. The nucleobases do not need to be linked to sugars. So-called peptide nucleic acid oligomers or morpholine-based oligomers can be used. A comparison of these different linking chemistries is found in Sazani, P. et al., 2001, Nucleic Acids Res. 29:3695 and in Crooke, S. T. (2008) Antisense Drug Technology, Boca Raton, CRC Press The term splice-switching oligonucleotide (SSO) is intended to cover the above forms. The SSO described in the examples of the present invention include 2'-OMe and MOE oligomers. It will be obvious to one skilled in the art that additional oligomer chemistries can be used to practice the invention including phosphorodiamidate-linked morpholino oligomers (PMO) or locked nucleic acid (LNA) oligomers as described below.

The SSOs of this invention can be made through the well-known technique of solid phase synthesis. Any other means for such synthesis known in the art can additionally or alternatively be used. It is well known to use similar techniques to prepare oligonucleotides such as the phosphorothioates and alkylated derivatives.

The bases of the SSO can be the conventional cytosine, guanine, adenine and uracil or thymidine bases. Alternatively, modified bases can be used. Of particular interest are modified bases that increase binding affinity. One non-limiting example of preferred modified bases are the so-called G-clamp or 9-(aminoethoxy)phenoxazine nucleotides, cytosine analogues that form 4 hydrogen bonds with guanosine. (Flanagan, W. M., et al., 1999, Proc. Natl. Acad. Sci. 96:3513; Holmes, S. C., 2003, Nucleic Acids Res. 31:2759). Specific examples of other bases include, but are not limited to, 5-methylcytosine (MeC), isocytosine, pseudoisocytosine. 5-(1-propynyl)-cytosine, 5-bromouracil, 5-(1-propynyl)-uracil, 5-propyny-6,5-methylthiazoleuracil, 6-aminopurine, 2-aminopurine, inosine, 2,6-diaminopurine, 7-propyne-7-deazaadenine, 7-propyne-7-deazaguanine and 2-chloro-6-aminopurine.

Those skilled in the art will appreciate the relationship between antisense oligonucleotide gapmers and SSOs. Gapmers are ASON that contain an RNase H activating region (typically a 2'-deoxyribonucleoside phosphorothioate) which is flanked by non-activating nuclease resistant oligomers. In general, any chemistry suitable for the flanking sequences in a gapmer ASON can be used in an SSO. For similar reasons, ASON chemistries that induce RNase H activity and do not contain flanking nuclease resistant oligomers are also not appropriate as SSOs.

VA. Phosphorodiamidate Morpholino Oligomers as SSOs

Figure 13D:
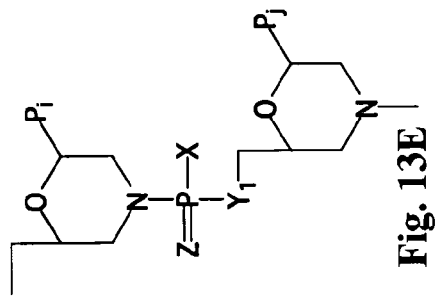
FIG. 13D-G: Repeating subunit segment of four exemplary morpholino oligonucleotides, designated D through G.
Figure 13E:
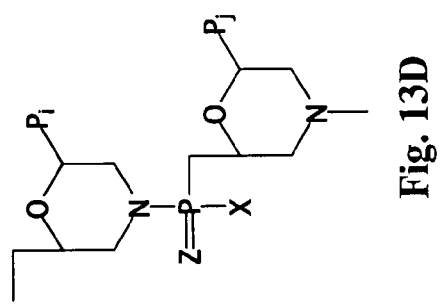
Figure 13F:
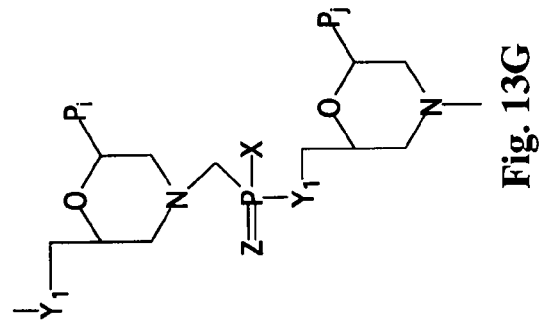
Figure 13G:
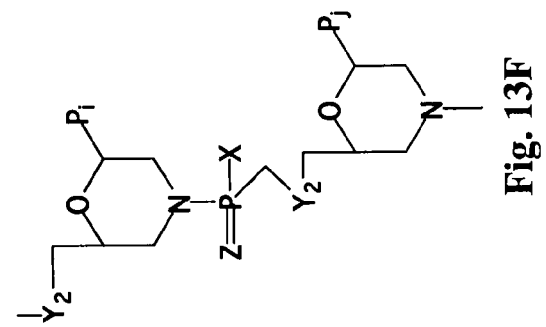
Figure 13A:
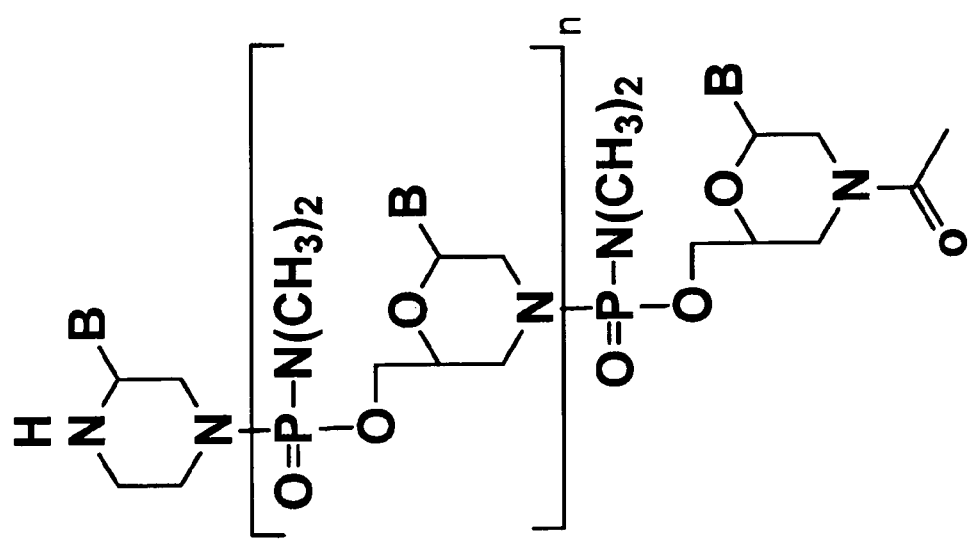
FIG. 13A-C: Exemplary structures of a phosphorodiamidate-linked morpholino oligomer (PMO) (FIG. 13A), a peptide-conjugated PMO (PPMO) (FIG. 13B), and a peptide-conjugated PMO having cationic intersubunit linkages (PPMO+) (FIG. 13C). Though multiple cationic linkage types are illustrated in FIG. 13C, a PMO+ or PPMO+ oligomer will typically include just one type of cationic linkage.
Figure 13B:
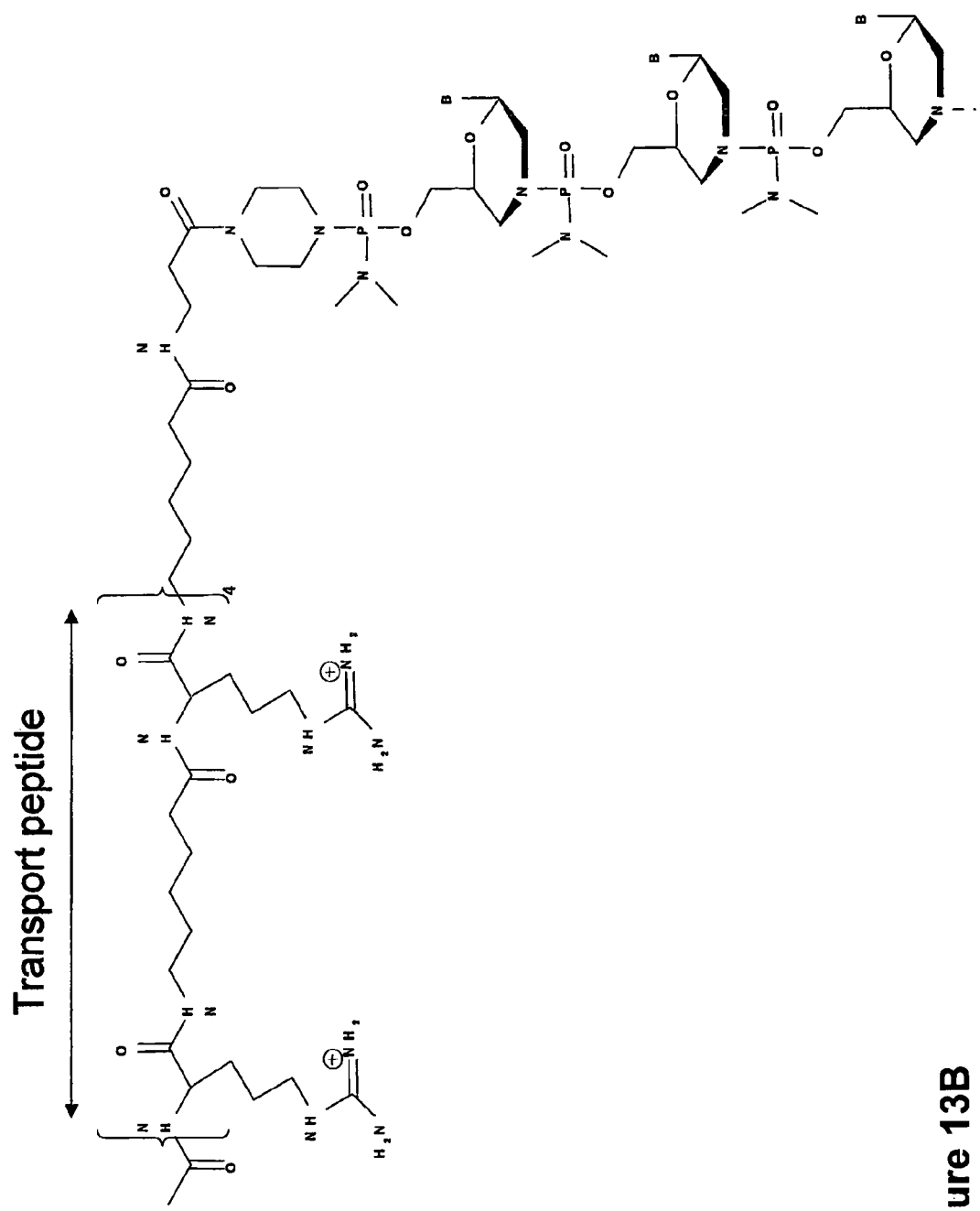
Figure 13C:
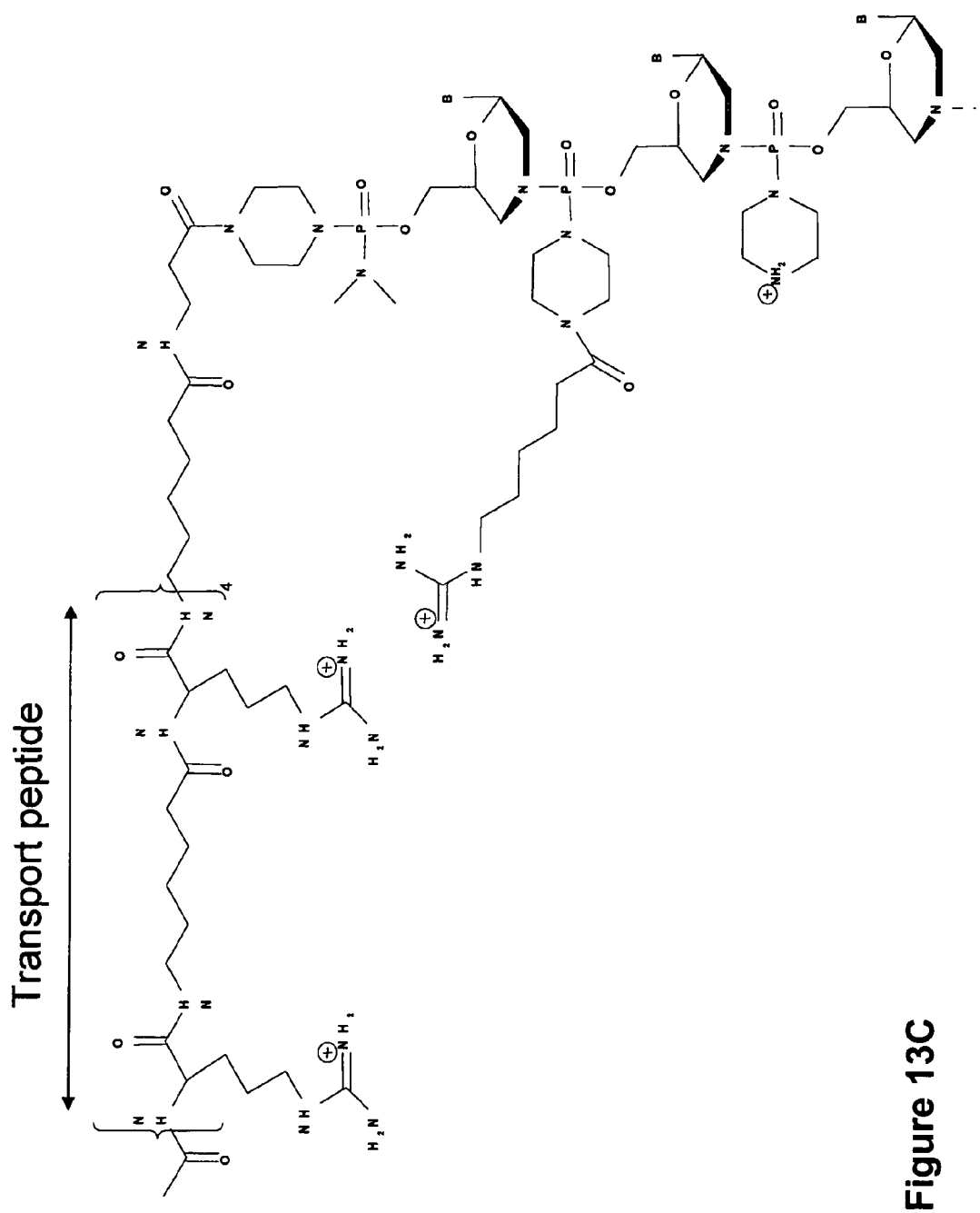

An example of a preferred SSO chemistry includes morpholino oligonucleotides having phosphorus-containing backbone linkages as illustrated in FIGS. 13A-13G. Also preferred is a phosphorodiamidate-linked morpholino oligonucleotide (PMO) such as shown in FIG. 13C, which is modified, in accordance with one aspect of the present invention, to contain positively charged groups at preferably 10%-50% of its backbone linkages. Morpholino oligonucleotides with uncharged backbone linkages, including antisense oligonucleotides, are detailed, for example, in (Summerton, J. and D. Weller (1997) Antisense Nucleic Acid Drug Dev 7(3): 187-95) and in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

Important properties of the morpholino-based subunits include: 1) the ability to be linked in a oligomeric form by stable, uncharged or positively charged backbone linkages; 2) the ability to support a nucleotide base (e.g. adenine, cytosine, guanine, thymidine, uracil and inosine) such that the polymer formed can hybridize with a complementary-base target nucleic acid, including target RNA, Tm values above about 45° C. in relatively short oligonucleotides (e.g., 10-15 bases); 3) the ability of the oligonucleotide to be actively or passively transported into mammalian cells; and 4) the ability of the antisense oligonucleotide:RNA heteroduplex to resist RNAse and RNaseH degradation, respectively.

Exemplary backbone structures for antisense oligonucleotides of the claimed subject matter include the morpholino subunit types shown in FIGS. 13D-G, each linked by an uncharged or positively charged, phosphorus-containing subunit linkage. FIG. 13D shows a phosphorus-containing linkage which forms the five atom repeating-unit backbone, where the morpholino rings are linked by a 1-atom phosphoamide linkage. FIG. 13E shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, mono-substituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

The linkages shown in FIGS. 13F and 13G are designed for 7-atom unit-length backbones. In structure 13F, the X moiety is as in Structure 13E, and the Y moiety may be methylene, sulfur, or, preferably, oxygen. In Structure 13G, the X and Y moieties are as in Structure 13E. Particularly preferred morpholino oligonucleotides include those composed of morpholino subunit structures of the form shown in FIG. 13E, where X=$NH_2$, $N(CH_3)_2$, or 1-piperazine or other charged group, Y=O, and Z=O.

As noted above, the substantially uncharged oligonucleotide may be modified, in accordance with an aspect of the invention, to include charged linkages, e.g. up to about 1 per every 2-5 uncharged linkages, such as about 4-5 per every 10 uncharged linkages. Optimal improvement in antisense activity may be seen when about 25% of the backbone linkages are cationic. Suboptimal enhancement is typically seen with a small number e.g., 10-20% cationic linkages, and where the number of cationic linkages are in the range 50-80%, and typically above about 60%, the sequence specificity of the antisense binding to its target may be compromised or lost.

The antisense compounds can be prepared by stepwise solid-phase synthesis, employing methods detailed in the references cited above, and below with respect to the synthesis of oligonucleotides having a mixture or uncharged and cationic backbone linkages. In some cases, it may be desirable to add additional chemical moieties to the antisense compound, e.g. to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense compound, it is generally of course desirable to select chemical compounds of groups that are biocompatible and likely to be tolerated by a subject without undesirable side effects.

As noted above, the antisense compound can be optionally constructed to contain a selected number of cationic linkages interspersed with uncharged linkages of the type described above. The intersubunit linkages, both uncharged and cationic, preferably are phosphorus-containing linkages, having the structure:

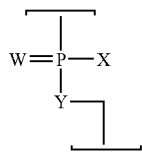

where
W is S or O, and is preferably O,
X=$NR^1R^2$ or $OR^6$,
Y=O or $NR^7$,
and each said linkage in the oligomer is selected from:
(a) uncharged linkage (a), where each of $R^1$, $R^2$, $R^6$ and $R^7$ is independently selected from hydrogen and lower alkyl;
(b1) cationic linkage (b1), where X=$NR^1R^2$ and Y=O, and $NR^1R^2$ represents an optionally substituted piperazino group, such that $R^1R^2$=CHRCHRN($R^3$)($R^4$)CHRCHR—, where
each R is independently H or $CH_3$,
$R^4$ is H, $CH_3$, or an electron pair, and
$R^3$ is selected from H, lower alkyl, e.g. $CH_3$, C(=NH)$NH_2$, Z-L-NHC(=NH)$NH_2$, and [C(O)CHR'NH]$_m$H, where: Z is C(O) or a direct bond, L is an optional linker up to 18 atoms in length, preferably up to 12 atoms, and more preferably up to 8 atoms in length, having bonds selected from alkyl, alkoxy, and alkylamino, R' is a side chain of a naturally occurring amino acid or a one- or two-carbon homolog thereof, and m is 1 to 6, preferably 1 to 4;
(b2) cationic linkage (b2), where X=$NR^1R^2$ and Y=O, $R^1$=H or $CH_3$, and $R^2$=LNR$^3$R$^4$R$^5$, where L, $R^3$, and $R^4$ are as defined above, and $R^5$ is H, lower alkyl, or lower (alkoxy)alkyl; and
(b3) cationic linkage (b3), where Y=$NR^7$ and X=$OR^6$, and $R^7$=LNR$^3$R$^4$R$^5$, where L, $R^3$, $R^4$ and $R^5$ are as defined above, and $R^6$ is H or lower alkyl;
and at least one said linkage is selected from cationic linkages (b1), (b2), and (b3).

Preferably, the oligomer includes at least two consecutive linkages of type (a) (i.e. uncharged linkages). In further embodiments, at least 5% of the linkages in the oligomer are cationic linkages (i.e. type (b1), (b2), or (b3)); for example, 10% to 60%, and preferably 20-50% linkages may be cationic linkages.

In one embodiment, at least one linkage is of type (b1), where, preferably, each R is H, $R^4$ is H, $CH_3$, or an electron pair, and $R^3$ is selected from H, lower alkyl, e.g. $CH_3$, C(=NH)$NH_2$, and C(O)-L-NHC(=NH)$NH_2$. The latter two embodiments of $R^3$ provide a guanidino moiety, either attached directly to the piperazine ring, or pendant to a linker group L, respectively. For ease of synthesis, the variable Z in $R^3$ is preferably C(O) (carbonyl), as shown.

The linker group L, as noted above, contains bonds in its backbone selected from alkyl (e.g. —$CH_2$—$CH_2$—), alkoxy (—C—O—), and alkylamino (e.g.—$CH_2$—NH—), with the proviso that the terminal atoms in L (e.g., those adjacent to carbonyl or nitrogen) are carbon atoms. Although branched linkages (e.g. —$CH_2$—CHCH$_3$—) are possible, the linker is preferably unbranched. In one embodiment, the linker is a hydrocarbon linker. Such a linker may have the structure —(CH$_2$)$_n$—, where n is 1-12, preferably 2-8, and more preferably 2-6.

The morpholino subunits have the structure:

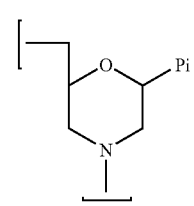

(i)

where Pi is a base-pairing moiety, and the linkages depicted above connect the nitrogen atom of (i) to the 5' carbon of an adjacent subunit. The base-pairing moieties Pi may be the same or different, and are generally designed to provide a sequence which binds to a target nucleic acid.

The use of embodiments of linkage types (b1), (b2) and (b3) above to link morpholino subunits may be illustrated graphically as follows:

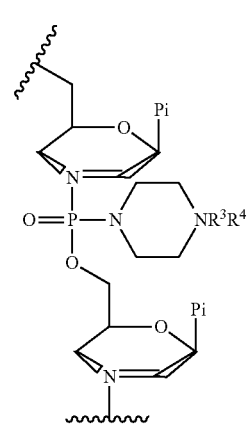

(b1)

-continued

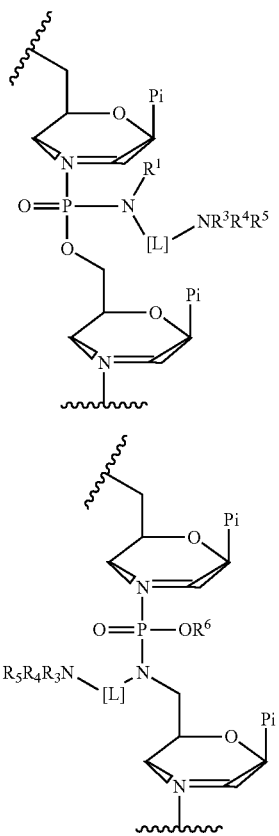

(b2)

(b3)

Preferably, all cationic linkages in the oligomer are of the same type; i.e. all of type (b1), all of type (b2), or all of type (b3).

In further embodiments, the cationic linkages are selected from linkages (b1') and (b1") as shown below, where (b1') is referred to herein as a "Pip" linkage and (b1") is referred to herein as a "GuX" linkage:

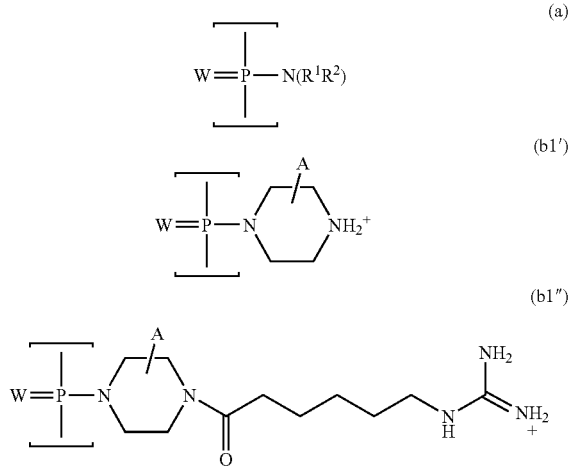

(a)

(b1')

(b1")

In the structures above, W is S or O, and is preferably O; each of $R^1$ and $R^2$ is independently selected from hydrogen and lower alkyl, and is preferably methyl; and A represents hydrogen or a non-interfering substituent on one or more carbon atoms in (b1') and (b1"). Preferably, the ring carbons in the piperazine ring are unsubstituted; however, they may include non-interfering substituents, such as methyl or fluorine. Preferably, at most one or two carbon atoms is so substituted.

In further embodiments, at least 10% of the linkages are of type (b1') or (b1"); for example, 10%-60% and preferably 20% to 50%, of the linkages may be of type (b1') or (b1").

In other embodiments, the oligomer contains no linkages of the type (b1') above. Alternatively, the oligomer contains no linkages of type (b1) where each R is H, $R^3$ is H or $CH_3$, and $R^4$ is H, $CH_3$, or an electron pair.

The morpholino subunits may also be linked by non-phosphorus-based intersubunit linkages, as described further below, where at least one linkage is modified with a pendant cationic group as described above.

Other oligonucleotide analog linkages which are uncharged in their unmodified state but which could also bear a pendant amine substituent could be used. For example, a 5'nitrogen atom on a morpholino ring could be employed in a sulfamide linkage or a urea linkage (where phosphorus is replaced with carbon or sulfur, respectively) and modified in a manner analogous to the 5'-nitrogen atom in structure (b3) above.

Oligomers having any number of cationic linkages are provided, including fully cationic-linked oligomers. Preferably, however, the oligomers are uncharged or partially charged, having, for example, 10%-80%. In preferred embodiments, about 10% to 60%, and preferably 20% to 50% of the linkages are cationic.

In one embodiment, the cationic linkages are interspersed along the backbone. The partially charged oligomers preferably contain at least two consecutive uncharged linkages; that is, the oligomer preferably does not have a strictly alternating pattern along its entire length.

Also considered are oligomers having blocks of cationic linkages and blocks of uncharged linkages; for example, a central block of uncharged linkages may be flanked by blocks of cationic linkages, or vice versa. In one embodiment, the oligomer has approximately equal-length 5', 3' and center regions, and the percentage of cationic linkages in the center region is greater than about 50%, preferably greater than about 70%.

Oligomers for use in antisense applications generally range in length from about 10 to about 40 subunits, more preferably about 10 to 30 subunits, and typically 15-25 bases. For example, an oligomer of the invention having 19-20 subunits, a useful length for an antisense compound, may ideally have two to ten, e.g. four to eight, cationic linkages, and the remainder uncharged linkages. An oligomer having 14-15 subunits may ideally have two to five, e.g. 3 or 7, cationic linkages and the remainder uncharged linkages.

Each morpholino ring structure supports a base pairing moiety, to form a sequence of base pairing moieties which is typically designed to hybridize to a selected antisense target in a cell or in a subject being treated. The base pairing moiety may be a purine or pyrimidine found in native DNA or RNA (A, G, C, T, or U) or an analog, such as hypoxanthine (the base component of the nucleoside inosine) or 5-methyl cytosine.

VB. Locked Nucleic Acids as SSOs

Another preferred chemistry appropriate for SSOs is provided by locked nucleic acids (LNA) (Koshkin, A. A., et al., 1998, Tetrahedron 54:3607; Obika, S., et al., 1998, Tetrahedron Lett. 39:5401). As used herein, the terms "LNA unit", "LNA monomer", "LNA residue", "locked nucleic acid unit", "locked nucleic acid monomer" or "locked nucleic acid residue", refer to a bicyclic nucleoside analogue. LNA units and methods of their synthesis are described in inter alia WO 99/14226, WO 00/56746, WO 00/56748, WO 01/25248, WO 02/28875, WO 03/006475 and WO 03/095467. The LNA unit can also be defined with respect to its chemical formula. Thus, an "LNA unit", as used herein, has the chemical structure shown in Formula I below:

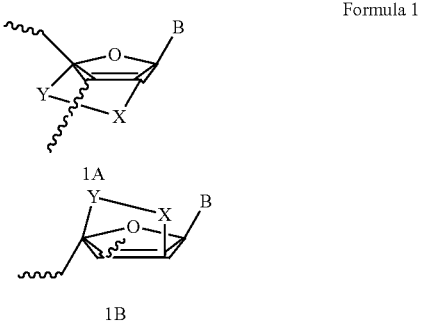

Formula 1 wherein,

X is selected from the group consisting of O, S and NRH, where R is H or $C_1$-$C_4$-alkyl;

Y is (—$CH_2$)$_r$, where r is an integer of 1-4; and

B is a base of natural or non-natural origin as described above.

In a preferred embodiment, r is 1 or 2, and in a more preferred embodiment r is 1.

When LNA nucleotides are employed in an SSO it is preferred that non-LNA nucleotides also be present. LNA nucleotides have such high affinities of hybridization that there can be significant non-specific binding, which may reduce the effective concentration of the free-SSO. When LNA nucleotides are used they can be alternated conveniently with 2'-deoxynucleotides. The pattern of alternation is not critical. Alternating nucleotides, alternating dinucleotides or mixed patterns, e.g., LDLDLD (SEQ ID NO:72) or LLDLLD (SEQ ED NO:73) or LDDLDD (SEQ ID NO:74) can be used. For example, one embodiment contains a sequence of nucleotides selected from the group consisting of: LdLddLLddLdLdLL (SEQ ID NO:75), LdLdLLLddLLLdLL (SEQ ID NO:76), LMLMMLLMMLMLMLL (SEQ ID NO:77), LMLM-LLLMMLLLMLL (SEQ ID NO:78), LFLFFLLFFLFLFLL (SEQ ID NO:79), LFLFLLLFFLLLLFLL (SEQ ID NO:80), LddLddLddL (SEQ ID NO:81), dLddLddLdd (SEQ ID NO:82), ddLddLddLd (SEQ ID NO:83), LMMLMMLMML (SEQ ID NO:84), MLMMLMMLMM (SEQ ID NO:85), MMLMMLMMLM (SEQ ID NO:86), LFFLFFLFFL (SEQ ID NO:87), FLFFLFFLFF (SEQ ID NO:88), FFLFFLFFLF (SEQ ID NO:89), dLdLdLdLdL (SEQ ID NO:90), LdLdLdLdL (SEQ ID NO:91), MLMLMLMLML (SEQ ID NO:92), LMLMLMLML (SEQ ID NO:93), FLFLFLFLFL (SEQ ID NO:94), LFLFLFLFL (SEQ ID NO:95), where L is a LNA unit, d is a DNA unit, M is 2'MOE, F is 2'fluoro.

When 2'-deoxynucleotides or 2'-deoxynucleoside phosphorothioates are mixed with LNA nucleotides it is important to avoid RNase H activation. It is expected that between about one third and two thirds of the LNA nucleotides of an SSO will be suitable to avoid RNase H activation. When affinity-enhancing modifications are used, including but not limited to LNA or G-clamp nucleotides, the skilled person will recognize that it can be necessary to increase the proportion of such affinity-enhancing modifications.

Numerous additional examples of alternative chemistries which do not activate RNase H are available. For example, suitable SSOs can be oligonucleotides wherein at least one of the internucleotide bridging phosphate residues is a modified phosphate, such as methyl phosphonate, methyl phosphonothioate, phosphoromorpholidate, phosphoropiperazidate, and phosphoroamidate. For example, every other one of the internucleotide bridging phosphate residues can be modified as described. In another non-limiting example, such SSOs are oligonucleotides wherein at least one of the nucleotides contains a 2' lower alkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides can be modified as described. (See references in U.S. Pat. No. 5,976,879 col. 4). For in vivo use, phosphorothioate linkages are preferred.

The length of the SSO will be from about 8 to about 30 bases in length. Those skilled in the art appreciate that when affinity-increasing chemical modifications are used, the SSO can be shorter and still retain specificity. Those skilled in the art will further appreciate that an upper limit on the size of the SSO is imposed by the need to maintain specific recognition of the target sequence, and to avoid secondary-structure forming self-hybridization of the SSO and by the need to enter the cell. These limitations imply that an SSO of increasing length (above and beyond a certain length which will depend on the affinity of the SSO) will be more frequently found to be less specific, inactive or poorly active.

VC. Chemical Modifications and Conjugates of SSOs

SSOs of the invention include, but are not limited to, modifications of the SSO involving chemically linking to the SSO one or more moieties or conjugates which enhance the activity, cellular distribution or cellular uptake of the SSO. Such moieties include, but are not limited to, peptides, lipid moieties such as a cholesterol moiety, cholic acid, a thioether, e.g. hexyl-5-tritylthiol, a thiocholesterol, an aliphatic chain, e.g., dodecandiol or undecyl residues, a phospholipids, e.g., di-hexadecyl-rac-glycerol or triethylammonium 1,2-di-O-hexadecyl-rac-glycero-3-H-phosphonate, a polyamine or a polyethylene glycol chain, an adamantane acetic acid, a palmityl moiety, an octadecylamine or hexylamino-carbonyl-oxycholesterol moiety.

A preferred chemical modification of SSO includes an oligonucleotide moiety conjugated to an arginine-rich peptide transport moiety effective to enhance transport of the compound into cells. The transport moiety is preferably attached to a terminus of the oligomer, as shown, for example, in FIGS. 13B and 13C. The peptide transport moiety preferably comprises 6 to 16 subunits selected from X' subunits, Y' subunits, and Z' subunits, where (a) each X' subunit independently represents lysine, arginine or an arginine analog, said analog being a cationic α-amino acid comprising a side chain of the structure $R^1N=C(NH_2)R^2$, where $R^1$ is H or R; $R^2$ is R, $NH_2$, NHR, or $NR_2$, where R is lower alkyl or lower alkenyl and may further include oxygen or nitrogen; $R^1$ and $R^2$ may together form a ring; and the side chain is linked to said amino acid via $R^1$ or $R^2$;

(b) each Y' subunit independently represents a neutral amino acid —C(O)—(CHR)$_n$—NH—, where n is 2 to 7 and each R is independently H or methyl; and (c) each Z' subunit independently represents an α-amino acid having a neutral aralkyl side chain;

wherein the peptide comprises a sequence represented by one of (X'Y'X')$_p$, (X'Y')$_m$, and (X'Z'Z')$_p$, where p is 2 to 5 and m is 2 to 8.

In selected embodiments, for each X', the side chain moiety is guanidyl, as in the amino acid subunit arginine (Arg). In further embodiments, each Y' is —CO—(CH$_2$)$_n$—CHR—NH—, where n is 2 to 7 and R is H. For example, when n is 5 and R is H, Y' is a 6-aminohexanoic acid subunit, abbreviated herein as Ahx; when n is 2 and R is H, Y' is a β-alanine subunit, abbreviated herein as B.

Preferred peptides of this type include those comprising arginine dimers alternating with single Y' subunits, where Y' is preferably Ahx. Examples include peptides having the formula (RY'R)$_p$ or the formula (RRY')$_p$, where Y' is preferably Ahx. In one embodiment, Y' is a 6-aminohexanoic acid subunit, R is arginine and p is 4.

In a further embodiment, each Z' is phenylalanine, and m is 3 or 4.

The conjugated peptide is preferably linked to a terminus of the oligomer via a linker Ahx-B, where Ahx is a 6-aminohexanoic acid subunit and B is a β-alanine subunit, as shown, for example, in FIGS. 13B and 13C.

In selected embodiments, for each X', the side chain moiety is independently selected from the group consisting of guanidyl (HN=C(NH$_2$)NH—), amidinyl (HN=C(NH$_2$)C<), 2-aminodihydropyrimidyl, 2-aminotetrahydropyrimidyl, 2-aminopyridinyl, and 2-aminopyrimidonyl, and it is preferably selected from guanidyl and amidinyl. In one embodiment, the side chain moiety is guanidyl, as in the amino acid subunit arginine (Arg).

The Y' subunits are either contiguous, in that no X' subunits intervene between Y' subunits, or interspersed singly between X' subunits. However, the linking subunit may be between Y' subunits. In one embodiment, the Y' subunits are at a terminus of the transporter; in other embodiments, they are flanked by X' subunits. In further preferred embodiments, each Y' is —CO—(CH$_2$)$_n$—CHR—NH—, where n is 2 to 7 and R is H. For example, when n is 5 and R is H, Y' is a 6-aminohexanoic acid subunit, abbreviated herein as Ahx. In selected embodiments of this group, each X' comprises a guanidyl side chain moiety, as in an arginine subunit. Preferred peptides of this type include those comprising arginine dimers alternating with single Y' subunits, where Y' is preferably Ahx. Examples include peptides having the formula (RY'R)$_4$ or the formula (RRY')$_4$, where Y' is preferably Ahx. In the latter case, the nucleic acid analog is preferably linked to a terminal Y' subunit, preferably at the C-terminus, as shown, for example, in FIGS. 13B and 13C. The preferred linker is of the structure AhxB, where Ahx is a 6-aminohexanoic acid subunit and B is a β-alanine subunit.

The transport moieties as described above have been shown to greatly enhance cell entry of attached oligomers, relative to uptake of the oligomer in the absence of the attached transport moiety, and relative to uptake by an attached transport moiety lacking the hydrophobic subunits Y'. Such enhanced uptake is preferably evidenced by at least a two-fold increase, and preferably a four-fold increase, in the uptake of the compound into mammalian cells relative to uptake of the agent by an attached transport moiety lacking the hydrophobic subunits Y'. Uptake is preferably enhanced at least twenty fold, and more preferably forty fold, relative to the unconjugated compound.

A further benefit of the transport moiety is its expected ability to stabilize a duplex between an antisense compound and its target nucleic acid sequence, presumably by virtue of electrostatic interaction between the positively charged transport moiety and the negatively charged nucleic acid. The number of charged subunits in the transporter is less than 14, as noted above, and preferably between 8 and 11, since too high a number of charged subunits may lead to a reduction in sequence specificity.

The use of arginine-rich peptide transporters (i.e., cell-penetrating peptides) are particularly useful in practicing the present invention. Certain peptide transporters have been shown to be highly effective at delivery of antisense compounds into primary leukocytes (Marshall, N. B., S. K. Oda, et al. (2007) J. Immunological Methods 325(1-2): 114-126). Furthermore, compared to other known peptide transporters such as Penetratin, the peptide transporters described herein, when conjugated to an antisense PMO, demonstrate an enhanced ability to alter splicing of several gene transcripts (Marshall, N. B., S. K. Oda, et al. (2007) J. Immunological Methods 325(1-2): 114-126). Especially preferred are the P007 and CPO6062 transport peptides listed below in Table 1 (SEQ ID NOS: 62 and 53, respectively).

Exemplary peptide transporters, including linkers (B or AhxB) are given below in Table 1. Preferred sequences are those designated P007 (SEQ ID NO: 62) and CPO6020 (SEQ ID NO: 53). Also preferred, in the present invention, are the peptide transporters identified as SEQ ID NOS: 48-50. As described in Example 4, these peptides showed superior delivery to mammary (SEQ ID NOS:56-58) and ovary (SEQ ID NO:58) tissues and may prove valuable when cancerous tissues derived from those tissues are targeted with the SSO of the present invention.

TABLE 1

Exemplary Peptide Transporters for Intracellular Delivery of PMO

| Peptide | Sequence (N-terminal to C-terminal) | SEQ ID |
|---|---|---|
| R$_8$XB | RRRRRRRR-XB | 52 |
| (RXRRBR)$_2$-XB (CPO6020) | RXRRBRRXRRBR-XB | 53 |
| (RXR)$_3$RBR-XB | RXRRXRRXRRBR-XB | 54 |
| (RB)$_5$RXRBRX-B | RBRBRBRBRBRXRBRX-B | 55 |
| (RBRBRBRX)$_2$-X | RBRBRBRXRBRBRBRX-X | 56 |
| X-(RB)$_3$RX(RB)$_3$RX | XRBRBRBRXRBRBRBR-X | 57 |
| (RBRX)$_4$B | RBRXRBRXRBRXRBRX-B | 58 |
| (RB)$_4$(RX)$_4$B | RBRBRBRBRXRXRXRX-B | 59 |
| RX(RB)$_2$RX(RB)$_3$RX-X | RXRBRBRXRBRBRBRX | 60 |
| (rXr)$_4$ | rXrrXrrXrrXr-XB | 61 |
| (RAhxR)$_4$AhxB (P007) | RAhxRRAhxRRAhXRRAhXRAhXB | 62 |
| (RRAhx)$_4$B | RRAhxRRAhxRRAhXRRAhXB | 63 |
| (AhxRR)$_4$AhxB | AhxRRAhxRRAhXRRAhXRRAhXB | 64 |
| (RAhx)$_6$B | RAhxRAhxRAhXRAhXRAhXRAhXB | 65 |
| (RAhx)$_8$B | RAhxRAhxRAhXRAhXRAhXRAhXRAhXRAhXB | 66 |
| (RAhxR)$_3$AhxB | RAhxRRAhxRRAhxR AhxB | 67 |

It is not necessary for all positions in a given SSO to be uniformly modified, and in fact more than one of the aforementioned modifications can be incorporated in a single compound or even at a single nucleoside within an SSO.

The SSOs can be admixed, encapsulated, conjugated, or otherwise associated with other molecules, molecule structures, or mixtures of compounds, as for example liposomes, receptor targeted molecules, oral, rectal, topical or other formulation, for assisting in uptake, distribution, and/or absorption.

Those skilled in the art appreciate that cellular differentiation includes, but is not limited to, differentiation of the spliceosome. Accordingly, the activity of any particular SSO can depend upon the cell type into which they are introduced. For example, SSOs which are effective in one cell type can be ineffective in another cell type.

VD. Methods and Applications of the SSOs

The methods, oligonucleotides, and formulations of the present invention are also useful as in vitro or in vivo tools to examine splicing in human or animal genes. Such methods can be carried out by the procedures described herein, or modifications thereof which will be apparent to skilled persons.

The SSOs disclosed herein can be used to treat any condition in which the medical practitioner intends to induce apoptosis in cells, or inhibit the proliferation of cells, or inhibit the signaling pathway activated by an EGFR, particularly HER2. In particular, the invention can be used to treat a proliferative disease or condition. In one embodiment, the condition is a cancer. In another embodiment, the disease is pulmonary fibrosis. In one embodiment, the condition is a cancer selected from the group consisting of breast, lung, ovarian, gastric and colon cancer. In one embodiment, the condition is a cancer which is resistant to chemotherapy.

The uses of the present invention include, but are not limited to, treatment of diseases for which known HER2 antagonists such as Herceptin, Herstatin and pertuzumab, have been shown useful.

The administration of the SSO to subjects can be accomplished using procedures developed for the administration of ASONs. ASONs have been successfully administered to experimental animals and human subjects by intravenous administration in saline in doses as high as 6 mg/kg three times a week (Yacysyhn, B. R., et al., 2002, Gut 51:30 (anti-ICAM-1 ASON for treatment of Crohn's disease); Stevenson, J., et al., 1999, J. Clinical Oncology 17:2227 (anti-RAF-1 ASON targeted to PBMC)). The pharmacokinetics of 2'O-MOE phosphorothioate ASON, directed towards TNF-α has been reported (Geary, R. S., et al., 2003, Drug Metabolism and Disposition 31:1419). The systemic efficacy of mixed LNA/DNA molecules has also been reported (Fluiter, K., et al., 2003, Nucleic Acids Res. 31:953).

The systemic activity of SSOs in a mouse model system was investigated using 2'O-MOE phosphorothioates, PMO and PNA chemistries. Significant activity was observed in all tissues investigated except brain, stomach and dermis (Sazani, P., et al., 2002, Nature Biotechnology 20, 1228).

In general any method of administration that is useful in conventional antisense treatments can be used to administer the SSOs of the invention. For testing of the SSO in cultured cells, any of the techniques that have been developed to test ASONs or SSOs can be used.

Formulations of the present invention comprise SSOs in a physiologically or pharmaceutically acceptable carrier, such as an aqueous carrier. Thus formulations for use in the present invention include, but are not limited to, those suitable for parenteral administration including intraperitoneal, intraarticular, intravenous, intraarterial, subcutaneous, or intramuscular injection or infusion, as well as those suitable for topical, ophthalmic, vaginal, oral, rectal or pulmonary (including inhalation or insufflation of powders or aerosols, including by nebulizer, intratracheal, intranasal delivery) administration. The formulations can conveniently be presented in unit dosage form and can be prepared by any of the methods well known in the art. The most suitable route of administration in any given case can depend upon the subject, the nature and severity of the condition being treated, and the particular active compound which is being used.

Pharmaceutical compositions of the present invention include, but are not limited to, physiologically and pharmaceutically acceptable salts, i.e, salts that retain the desired biological activity of the parent compound and do not impart undesired toxicological properties. Examples of such salts are (a) salts formed with cations such as sodium, potassium, $NH_4^+$, magnesium, calcium, polyamines such as spermine and spermidine; (b) acid addition salts formed with inorganic acids, for example, hydrochloric acid, hydrobromic acid, sulfuric acid, phosphoric acid, nitric acid and the like; and (c) salts formed with organic acids such as, for example, acetic acid, oxalic acid, tartaric acid, succinic acid, maleic acid, fumaric acid, gluconic acid, citric acid, malic acid, ascorbic acid, benzoic acid, palmitic acid, alginic acid, polyglutamic acid, napthalenesulfonic acid, methanesulfonic acid, p-toluenesulfonic acid, napthalenedisulfonic acid, polygalacturonic acid, and the like.

The present invention provides for the use of SSOs having the characteristics set forth above for the preparation of a medicament for increasing the ratio of a mammalian soluble form of either HER-2 or HER-3 to its corresponding membrane bound form, in a patient afflicted with a proliferative disorder, as discussed above. In the manufacture of a medicament according to the invention, the SSOs are typically admixed with, inter alia, an acceptable carrier. The carrier must, of course, be acceptable in the sense of being compatible with any other ingredients in the formulation and must not be deleterious to the patient. The carrier can be a solid or liquid. SSOs are incorporated in the formulations of the invention, which can be prepared by any of the well known techniques of pharmacy consisting essentially of admixing the components, optionally including one or more accessory therapeutic ingredients.

Formulations of the present invention can comprise sterile aqueous and non-aqueous injection solutions of the active compounds, which preparations are preferably isotonic with the blood of the intended recipient and essentially pyrogen free. These preparations can contain anti-oxidants, buffers, bacteriostats, and solutes which render the formulation isotonic with the blood of the intended recipient. Aqueous and non-aqueous sterile suspensions can include, but are not limited to, suspending agents and thickening agents. The formulations can be presented in unit dose or multi-dose containers, for example, sealed ampoules and vials, and can be stored in freeze-dried (lyophilized) condition requiring only the addition of the sterile liquid carrier, for example, saline or water-for-injection immediately prior to use.

In the formulation the SSOs can be contained within a particle or vesicle, such as a liposome, or microcrystal, which can be suitable for parenteral administration. The particles can be of any suitable structure, such as unilamellar or plurilameller, so long as the SSOs are contained therein. Positively charged lipids such as N-[1-(2,3-dioleoyloxy)propyl]-N,N,N-trimethyl-ammoniummethylsulfate, or "DOTAP," are particularly preferred for such particles and vesicles. The preparation of such lipid particles is well known. [See references in U.S. Pat. No. 5,976,879 col. 6]

The SSO can be targeted to any element or combination of elements that regulate splicing, including the 3' splice site, the 5' splice site, the branch point, the polypyrimidine tract, exonic splicing enhancers, exonic splicing silencers, intronic splicing enhancers, and intronic splicing silencers.

Those skilled in the art can appreciate that the invention as directed toward human HER2 can be practiced using SSOs having a sequence that is complementary to at least 8, to at least 9, to at least 10, to at least 11, to at least 12, to at least 13, to at least 14, to at least 15, preferably between 10 and 20 nucleotides of the portions of the human HER2 gene comprising exon 15 and its adjacent introns. SEQ ID No: 15 contains the sequence of exon 15 of human HER2 and 50 adjacent nucleotides of the flanking introns. For example, SSOs targeted to human HER2 can have a sequence selected from the sequences with splice-switching activity listed in Table 2. SSO that target (i.e., are complementary to) exon and adjacent intron regions of Exon 15 in the HER2 pre-mRNA (SEQ ID NO: 15) are useful in practicing the invention. More preferred are SSOs that target the HER2 pre-mRNA in the vicinity of the Exon 15 splice donor and splice acceptor junctions. These target sequence regions are defined as 50 nucleotides upstream (i.e., 5') and downstream (i.e., 3') of the splice acceptor and splice donor junctions (SEQ ID NOS: 44 and 45, respectively).

Those skilled in the art can appreciate that the invention as directed toward human HER3 can be practiced using SSOs having a sequence that is complementary to at least 8, to at least 9, to at least 10, to at least 11, to at least 12, to at least 13, to at least 14, to at least 15, preferably between 10 and 20 nucleotides of the portions of the human HER3 gene comprising exons 13, 14 and 15 and its adjacent introns, as well as the region containing the polyadenylation signal in exon 28. SEQ ID No: 16 contains the human HER3 sequence of exons 13 through 15 including the intervening introns and 50 adjacent nucleotides of the flanking introns. SEQ ID No: 17 contains the sequence of the region containing the polyadenylation signal in exon 28 of human HER3. For example, SSOs targeted to human HER3 can have a sequence selected from the sequences with splice-switching activity listed in Table 3. SSO that target (i.e., are complementary to) exon and adjacent intron regions of HER3 pre-mRNA in the vicinity of Exons 13, 14 and 15 (SEQ ID NO: 16) are useful in practicing the invention. More preferred are SSOs that target the HER3 pre-mRNA in the vicinity of the Exon 13, 14 and 15 splice donor and splice acceptor junctions. These preferred target sequence regions are defined as 50 nucleotides upstream (i.e., 5') and downstream (i.e., 3') of the splice acceptor and splice donor junctions (SEQ ID NOS: 46 to 51, respectively).

When affinity-enhancing modifications are used, including but not limited to LNA or G-clamp nucleotides, the skilled person recognizes the length of the SSO can be correspondingly reduced. The pattern of alternation of LNA and conventional nucleotides is not important.

Those skilled in the art will also recognize that the selection of SSO sequences must be made with care to avoid a self-complementary SSO, which may lead to the formation of partial "hairpin" duplex structures. In addition, high GC content should be avoided to minimize the possibility of non-specific base pairing. Furthermore, SSOs matching off-target genes, as revealed for example by BLAST, should also be avoided.

In some situations, it can be preferred to select an SSO sequence that can target a human and at least one other species. These SSOs can be used to test and to optimize them in the other species before being used in humans, thereby being useful for regulatory approval and drug development purposes.

It will be appreciated by those skilled in the art that various omissions, additions and modifications may be made to the invention described above without departing from the scope of the invention, and all such modifications and changes are intended to fall within the scope of the invention, as defined by the appended claims. All references, sequence citations, patents, patent applications or other documents cited are herein incorporated by reference.

Example 1

Materials and Methods

Cell culture and transfections: SK-BR-3 cells were maintained in McCoy's 5A media supplemented with 10% fetal bovine serum. MCF-7 cells were maintained in modified essential media supplemented with 10% fetal bovine serum, 1 mM sodium pyruvate, and 0.1 mM nonessential amino acids. For transfection, treatment, the cells were plated either in 2 mL of media in 6-well plates at a density of $2 \times 10^5$ cells/well, or in 1 mL of media in 24-well plates at a density of $1 \times 10^5$ cells/well and transfected 24 hours later. Oligonucleotides were complexed, at the indicated concentrations, with Lipofectamine™ 2000 (Invitrogen), and the cationic lipid complexes were applied to the cells according to the manufacturer's directions.

RT-PCR: Total RNA was isolated 24 hours after transfection, by harvesting the cells in 800 µL of TRI-reagent (Molecular Research Center, Inc.). Approximately 200 ng of RNA was used per reaction with rTth enzyme (PerkinElmer Life Sciences) in the presence of 0.02 mM Cy5-AP3-dCTP (GE Healthcare) and forward and reverse primers flanking the targeted mRNA region. The reaction mixture was incubated at 70° C., 15 min for the RT step followed by PCR: 95° C., 3 min, 1 cycle; 22 cycles of 95° C. for 30 sec, 56° C. for 30 sec, 72° C. for 1 min; and final extension at 72° C. for 7 min. The PCR products were separated on a 10% pre-cast TBE-Urea polyacrylamide gel (Invitrogen), and bands were visualized on Typhoon™ Variable Mode Imager (GE Healthcare). The density of the bands was quantified with ImageQuant™ software (GE Healthcare).

Cell viability assay: Cell viability post oligo treatment was measured by CellTiter 96® $AQ_{ueous}$ One Solution Cell Proliferation Assay (Promega). Cells (~$2 \times 10^4$/well) were plated in 96-well plates. On the next day, cells were transfected with 100 nM of the indicated SSOs. After 48 hours, CellTiter 96® $AQ_{ueous}$ One Solution reagent was added into each well of the 96-well plate. The plate was incubated at 37° C. for 1-4 hours. The absorbance was recorded at 490 nm using a 96-well plate reader. Cell viability was normalized to untreated cells.

PARP cleavage assay: Cells were plated in 6-well plates and transfected with the designated SSOs. After 48 hours, cells were harvested in RIPA buffer (radioimmune precipitation assay buffer; 50 mM Tris-HCl, 150 mM NaCl, 5 mM EDTA, 1% Triton X-100, 0.1% SDS, and 1% sodium deoxycholate) (Sigma) and a mixture of protease inhibitors (Sigma). Total protein (20 µg) was electrophoresed on a 4-12% NuPAGE Novex Bis-Tris gel (Invitrogen) and electrotransferred to polyvinylidene difluoride (PVDF) membranes (Invitrogen). Membranes were blocked for 30 min with StartingBlock (PBS) blocking buffer (Pierce) and incubated overnight at 4° C. with mouse PARP monoclonal antibody (1:10,000 dilution; Invitrogen), followed by 2-hour incubation with horseradish peroxidase-conjugated anti-mouse (1:100,000; Invitrogen) secondary antibodies. Blots were developed with ECL Plus™ reagents (GE Healthcare) and exposed to Kodak film. Full-length and cleaved PARP proteins migrated at ~116 and 85 kDa, respectively.

Plasmid constructs and purification of Δ15HER2-His protein: The Δ15HER2 sequence was reverse-transcribed and amplified from the total RNA isolated from SK-BR-3 cells treated with SSO111. The forward and reverse primers used were CACCATGGAGCTGGCGGCCT (SEQ ID NO: 68) and TCCAGGTCCACACAGCGGTCC (SEQ ID NO: 69), respectively. The Δ15HER2 sequence was cloned into the pcDNA™3.1, a directional TOPO expression vector (Invitrogen), which encodes six histidine residues at the carboxy terminus of the expressed protein. The Δ15HER2-His expression plasmid was transfected into MCF-7 cells with Lipofectamine™ 2000 (Invitrogen) in serum-free medium. After 48 hours, the medium was collected, concentrated, purified with HisPur™ Cobalt spin columns (Pierce), and desalted using Zeba™ Desalt spin columns to yield the soluble Δ15HER2-His protein. Purity of the protein was confirmed by SDS-PAGE, and the yield was determined by Bradford Assay. Inhibition of SK-BR-3 cell growth by the Δ15HER2-His protein was evaluated by plating cells at ~2×10$^4$ cells/well in 96 well plates for 24 hours, and then treated with 60, 120 or 240 nM Δ15HER2-His protein for 72 hours. Cell viability was normalized to mock-treated cells and analyzed using CellTiter 960 Aqueous Solution reagent (Promega).

Western blots: Transfected cells were harvested 48 hours post transfection (or at the indicated time points) in RIPA buffer (radioimmune precipitation assay buffer 50 mM Tris-HCl, 150 mM NaCl, 5 mM EDTA, 1% Triton X-100, 0.1% SDS, and 1% sodium deoxycholate) (Sigma) and a mixture of protease inhibitors (Sigma). Total protein (20 μg for PARP, β-actin, HER2, p-HER2, HER3 and p-HER3) from the cells was electrophoresed on a 4-10% pre-cast Bis-Tris gel (Invitrogen) and electrotransferred to polyvinylidene difluoride membranes. Membranes were blocked for 30 min in StartingBlock (PBS) blocking buffer (Pierce) and incubated overnight at 4° C. with rabbit anti-erbB2 polyclonal antibody (1:1000 dilution; Abcam), rabbit anti-erbB3 polyclonal antibody (1:1000 dilution; Abcam), rabbit phospho-HER2/erbB2 (Tyr877) polyclonal antibody (1:4000 dilution; Cell Signaling), rabbit phospho-HER3/erbB3 (Tyr1289) monoclonal antibody (1:4000 dilution; Cell Signaling), or mouse anti-PARP monoclonal antibody (1:1000 dilution; Invitrogen), followed by 1-hour incubation with horseradish peroxidase-conjugated anti-rabbit (1:100,000 dilution; Abcam) or anti-mouse (1:100,000 dilution; Invitrogen) secondary antibodies. Blots were developed with ECL™ Plus reagents (GE Healthcare) and exposed to Kodak film. HER2, HER3, full-length PARP, cleaved PARP, and β-actin migrated at ~180, 185, 116, 85, 42 kDa, respectively. β-actin was used as a loading control.

Example 2

HER2 Splice Variants

Exemplary splice switching oligonucleotides (SSOs) containing phosphorothioate internucleotide bonds and targeted to regions of human HER2 pre-mRNA (FIG. 1, Table 2) were synthesized.

TABLE 2

Splice switching Oligonucleotides Targeted to HER2

| SEQ ID. | Name | Sequence (5'-3') | Modification | Activity |
|---|---|---|---|---|
| 18 | 106 | ggg cag aaa aga ttt gtg gg | 2'-OMe, PS | + |
| 19 | 107 | cac act ggt cag cct cct gg | 2'-OMe, PS | + |
| 20 | 108 | gcc aca cac tgg tca gcc tc | 2'-OMe, PS | + |
| 21 | 109 | ctc acg agt ggg tgc agt tg | 2'-OMe, PS | + |
| 22 | 110 | gtt gga ctc acg agt ggg tg | 2'-OMe, PS | + |
| 23 | 111 | gac cgt tgg act cac gag tg | 2'-OMe, PS | + |
| 24 | M111 | gac cgt tgg act cac gag tg | MOE, PS | + |
| 25 | L111 | CgTtGgAcTcAcGaGt | Upper case: LNA; lower case: deoxyribose, PS | + |

2'-OMe, 2'-O-methyl oligoribonucleotide; MOE, 2'-O-methoxyethyl oligoribonucleotide; LNA, locked nucleic acid oligonucleotide; PS, phosphorothioate internucleotide linkage.

These oligonucleotides were transfected into SK-BR-3 human breast cancer cells with the cationic transfection reagent Lipofectamine™ 2000 (Invitrogen) as per the manufacturer's directions. After 24 hours, the total RNA was collected and RT-PCR was used to determine the ratio of HER2 lacking exon 15 (sHER2) and full length HER2 (mHER2) mRNA.

Figure 2:
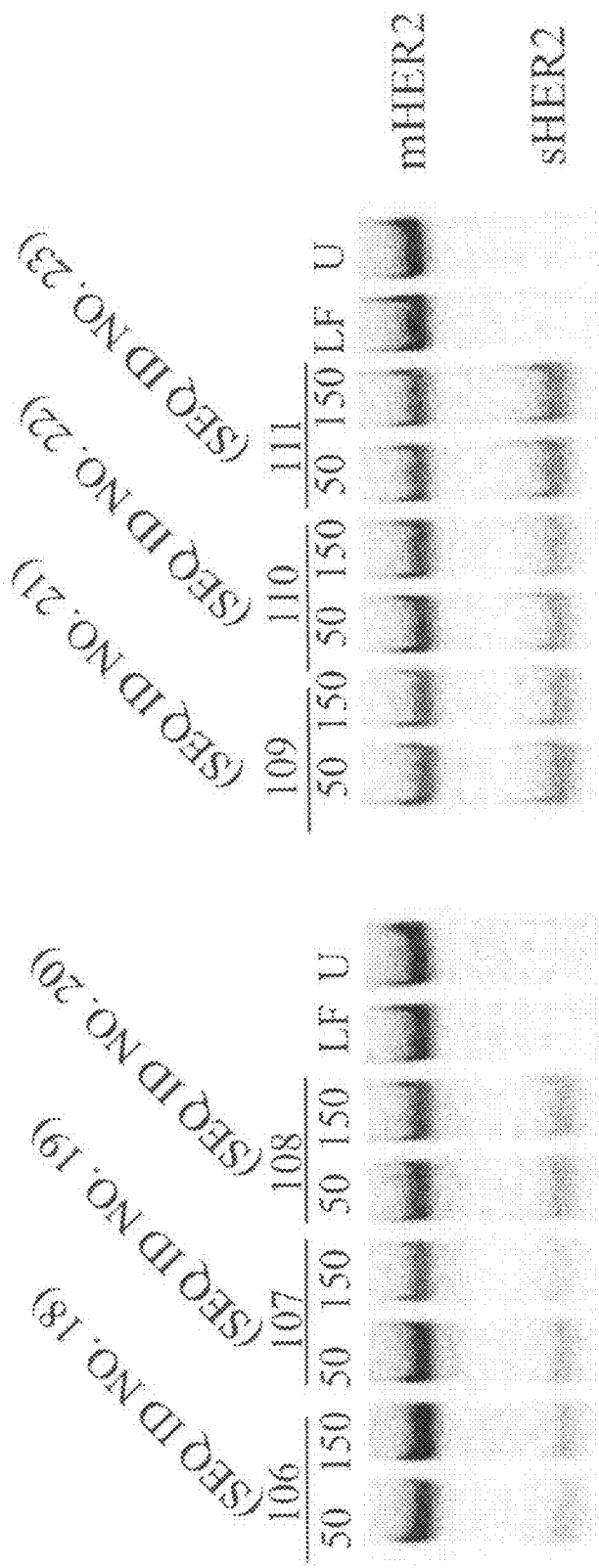
FIG. 2: SK-BR-3 cells were transfected with the indicated concentration (50 or 150 nM) of the indicated oligonucleotide. Twenty-four hours later total RNA was isolated and RT-PCR was used to amplify a fragment of HER2 mRNA. Full length Her2 transcripts are represented by a 307 bp band (mHER2), and transcripts lacking exon 15 are represented by a 246 bp band (sHER2). LF, Lipofectamine™ 2000 only; U, untreated cells.
Figure 3:
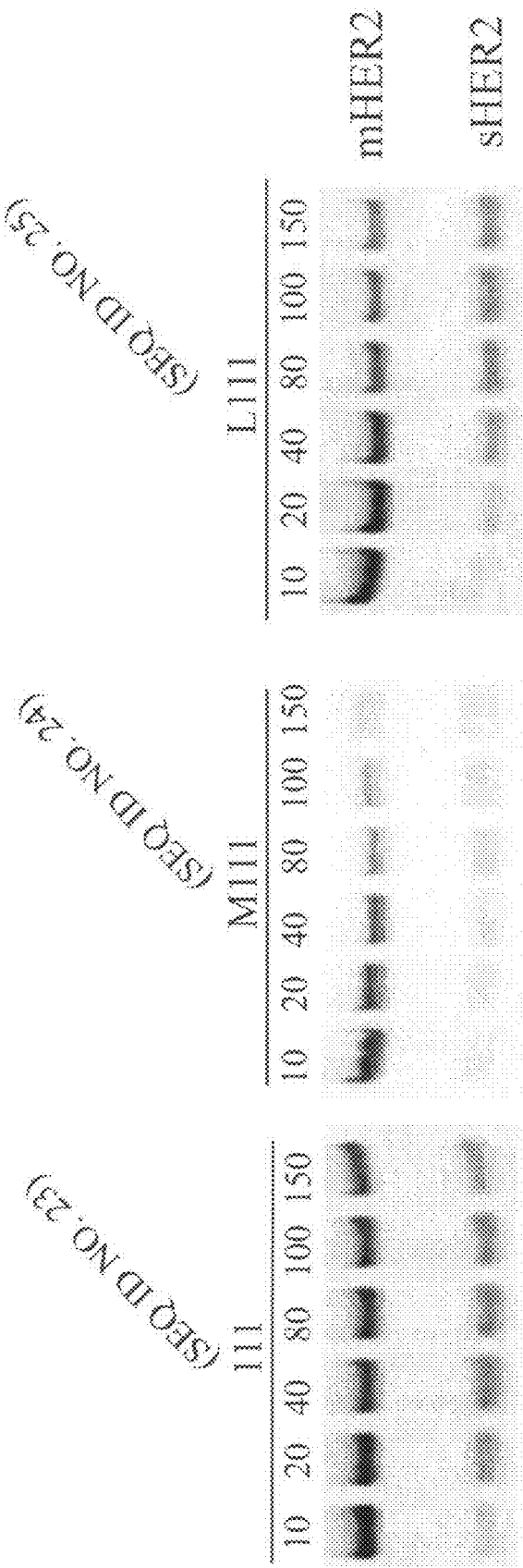
FIG. 3: SK-BR-3 cells were transfected with the indicated concentration (10, 20, 40, 80, 100, 150 nM) of either oligonucleotide 111, M111 or L111 as described in FIG. 2.

As shown in FIG. 2 and FIG. 3 these SSOs, especially SSO111, (SEQ ID NO. 23) caused skipping of exon 15, leading to reduced levels of mHER2 mRNA and increased levels of sHER2 mRNA. This same sequence was also effective at skipping exon 15 in a dose dependant manner, when synthesized as a 2'-OMe (SEQ ID NO. 23), an MOE (SEQ ID NO. 24) or an LNA (SEQ ID NO. 25) oligomer (FIG. 3).

Figure 4:
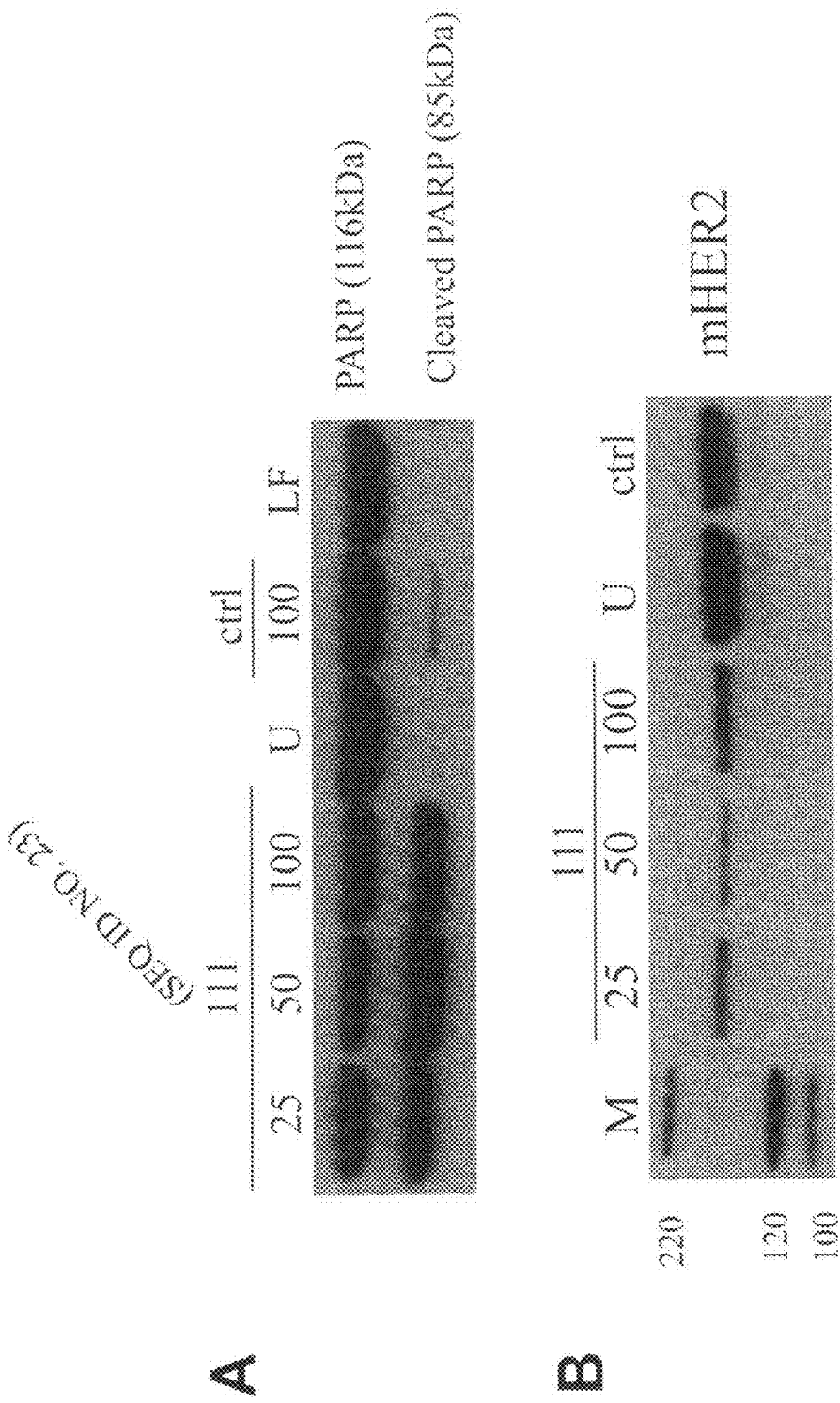
FIG. 4: SK-BR-3 cells were transfected with the indicated concentration (25, 50, 100 nM) of SSO111 as described in FIG. 2. After 48 hours, lysates were analyzed by western blot for A) poly(ADP ribose) polymerase (PARP) cleavage and B) mHER2 protein expression. LF, Lipofectamine™ 2000 only; U, untreated cells.

SSO111 (SEQ ID NO. 23) was transfected into SK-BR-3 human breast cancer cells with the cationic transfection reagent Lipofectamine™ 2000 (Invitrogen) as per the manufacturer's directions. After 48 hours, cells were collected in RIPA lysis buffer (Sigma) and the lysates were analyzed by western blot for poly (ADP ribose) polymerase (PARP) cleavage and mHER2 protein expression (FIG. 4). PARP is involved with DNA repair and is cleaved by caspases early in apoptosis. Therefore, PARP cleavage is indicative of apoptosis. The SSO111-induced upregulation of sHER2 protein caused the induction of poly(ADP ribose) polymerase (PARP) cleavage, an apoptotic marker, in transfected SK-BR-3 cells (FIG. 4A), and a simultaneous downregulation of mHER2 protein (FIG. 4B).

Figure 5:
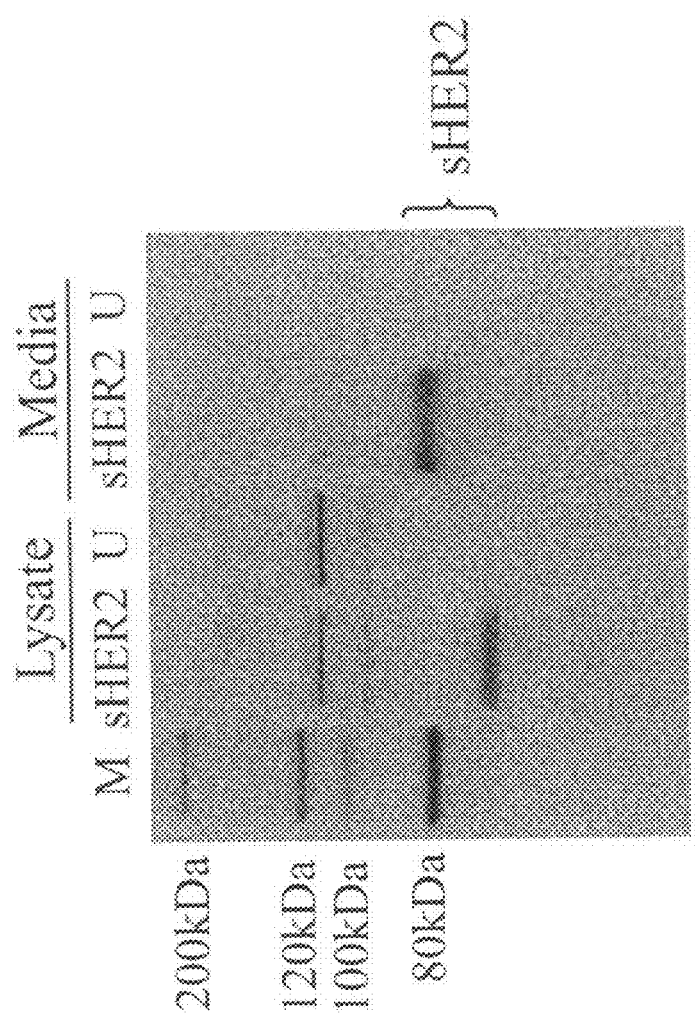
FIG. 5: MCF-7 cells were transfected with mammalian expression plasmids containing Δ15HER2 (sHER2) cDNA. After 48 hours, cell lysates and extracellular media were analyzed by western blot. Unglycosylated (~64 kD) and glycosylated (~80 kD) sHER2 protein was detected in the lysate (Lysate) and extracellular media (Media), respectively.

The cDNA encoding Δ15HER2 (sHER2) was cloned into a mammalian expression vector, which was then transfected into and expressed in MCF-7 cells. After 48 hours, cell lysates and concentrated extracellular media were collected and analyzed by western blot for the presence of HER2 isoforms. Unglycosylated (~64 kDa) and glycosylated (~80 kDa) sHER2 protein was detected only in sHER2 plasmid transfected cells, in the lysate (Lysate) and extracellular media (Media), respectively (FIG. 5). As shown in FIG. 5, the sHER2 protein was produced, processed and secreted from cells.

Figures 6A, 6B:
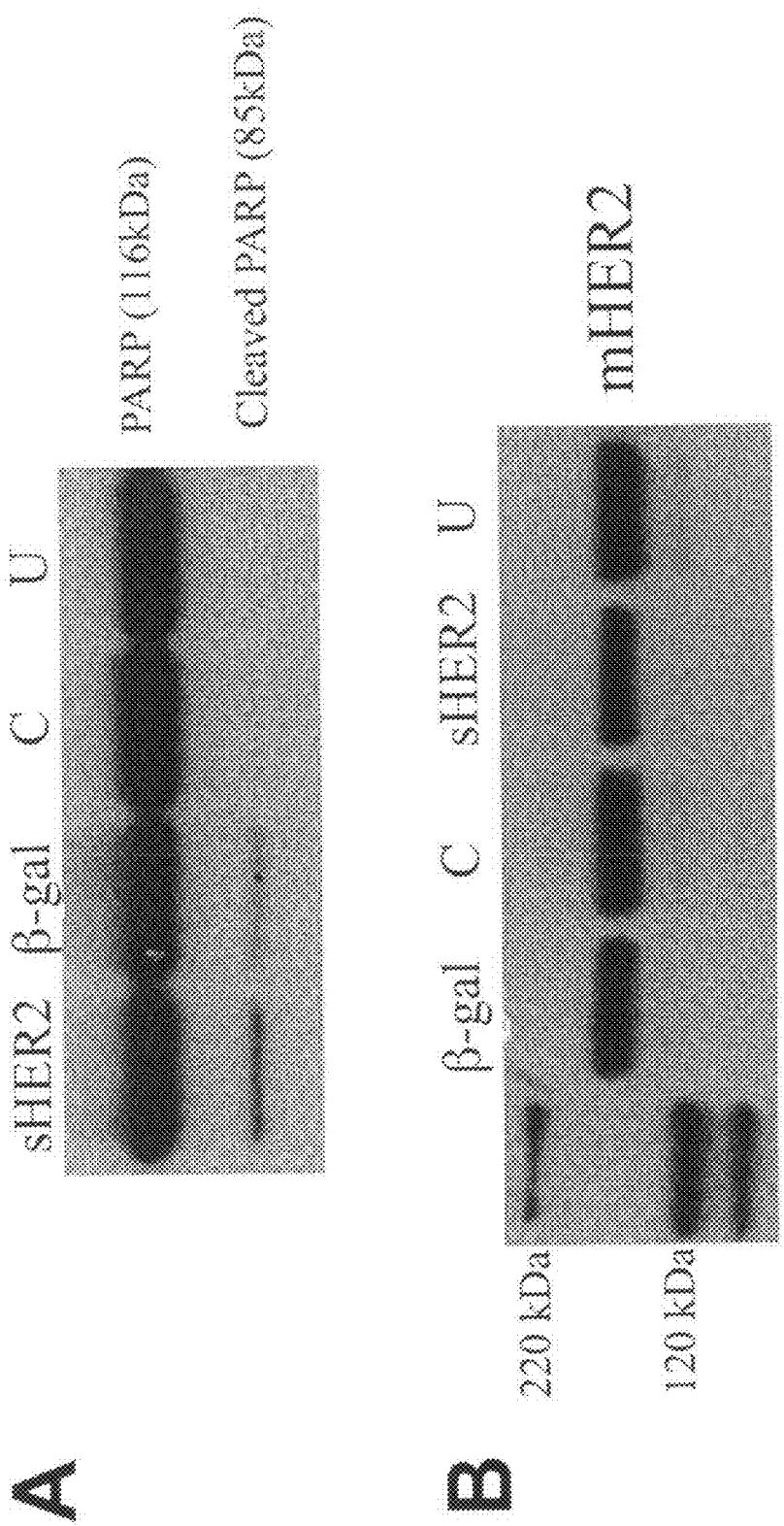
FIG. 6: MCF-7 cells were transfected with the sHER2 plasmid, or a control plasmid expressing β-galactosidase. The extracellular media was then transferred to the extracellular media of cultured SK-BR-3 cells and incubated for 48 hours. The SK-BR-3 cells were then analyzed for A) PARP cleavage (FIG. 6A) and B) mHER2 expression as in previous figures (FIG. 6B). SK-BR-3 cells were treated with purified Δ15HER2-His protein at designated concentrations and analyzed for HER2, HER3, and their phosphorylation status (FIG. 6C).
FIG. 6D shows growth inhibition of SK-BR-3 cells by Δ15HER2-His protein treatment after 72 hours incubation analyzed by an MTS assay. Shown are the mean±standard deviation of triplicates.

The extracellular media from the MCF-7 cells expressing sHER2 was transferred to the media of SK-BR-3 cells. After 48 hours, cells were collected in RIPA lysis buffer (Sigma) and the lysates were analyzed by western blot for PARP cleavage and mHER2 protein expression (FIG. 6). Incubation with sHER2 resulted in the induction of apoptosis in those cells, as shown by PARP cleavage assays (FIG. 6A). The application of exogenous sHER2 protein to cultured SK-BR-3 cells also caused a reduction in HER2 expression levels (FIG. 6B). Relative to the intensity of the mHER2 band for untreated SK cells, the band intensities for 1-gal, control (C), and sHER2 were 82%, 92%, and 73%, respectively.

Figure 6C:
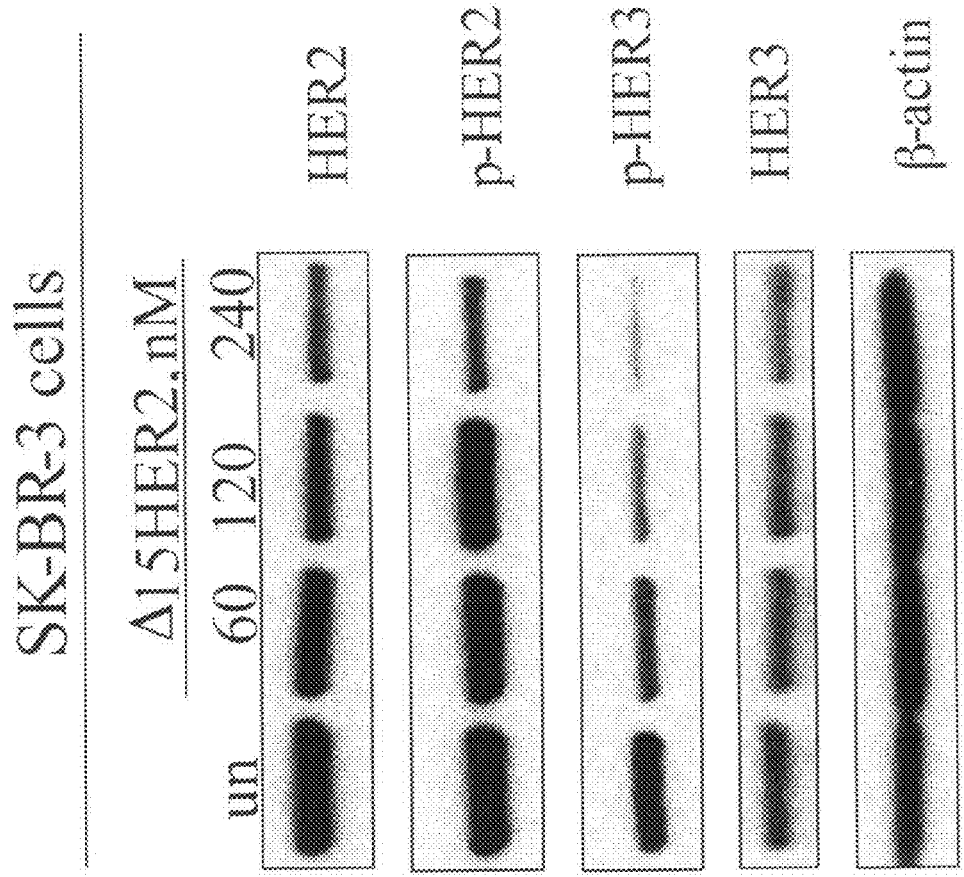
Figure 6D:
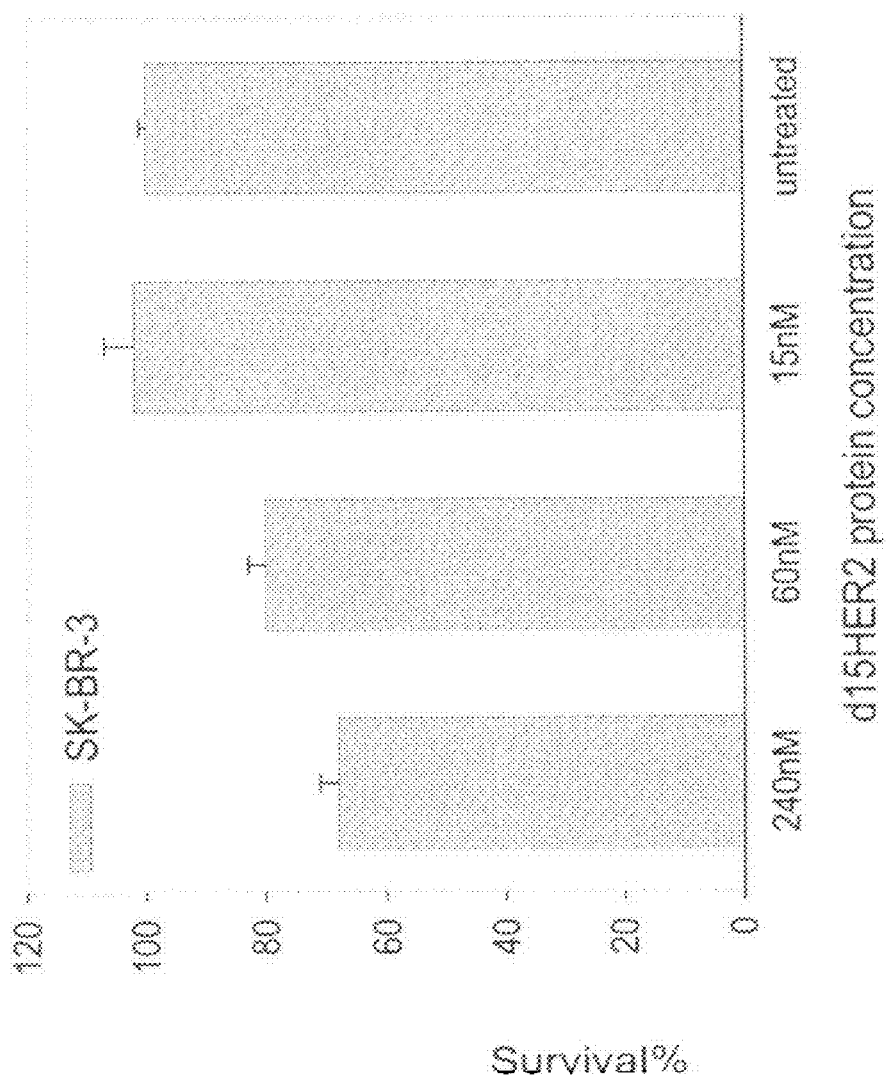

A cloned and purified C-terminal 6-His tag bearing version of the sHER2 protein (Δ15HER2-His) was applied at concentrations of 60, 120, or 240 nM to the culture media of SK-BR-3 cells, and after 48 hours incubation, cells were analyzed by Western blot for HER2, HER3, and their phosphorylation status. Increasing concentrations of Δ15HER2-His protein decreased total HER2 protein in the cells by up to 80% while phosphorylated HER2 (p-HER2) decreased up to 80% by 240 nM Δ15HER2-His. In agreement with established importance of HER2 in HER3 phosphorylation in SK-BR-3 cells, phosphorylated HER3 (p-HER3) also decreased in a dose-dependent manner in parallel with HER2 protein while the affect on HER3 was minimal (FIG. 6C). The densities of the bands shown in the gels in FIG. 6 were quantified with ImageQuant™ (GE Healthcare) software. Growth inhibition of SK-BR-3 cells by Δ15HER2-His protein treatment after 72 hours incubation was analyzed by MTS assay. Inhibition was evaluated by plating cells at ~2×10$^4$ cells/well in 96 well plates for 24 hours, and then treated with 60, 120 or 240 nM Δ15HER2-His protein for 72 hours. Cell viability was normalized to mock-treated cells and analyzed using CellTiter 96® Aqueous Solution reagent (Promega). Shown in FIG. 6D are the mean±standard deviation of triplicates (FIG. 6D). The Δ15HER2-His protein treatment decreased viability of SK-BR-3 cells in a dose-dependent manner.

Example 3

HER3 Splice Variants

Figure 7:
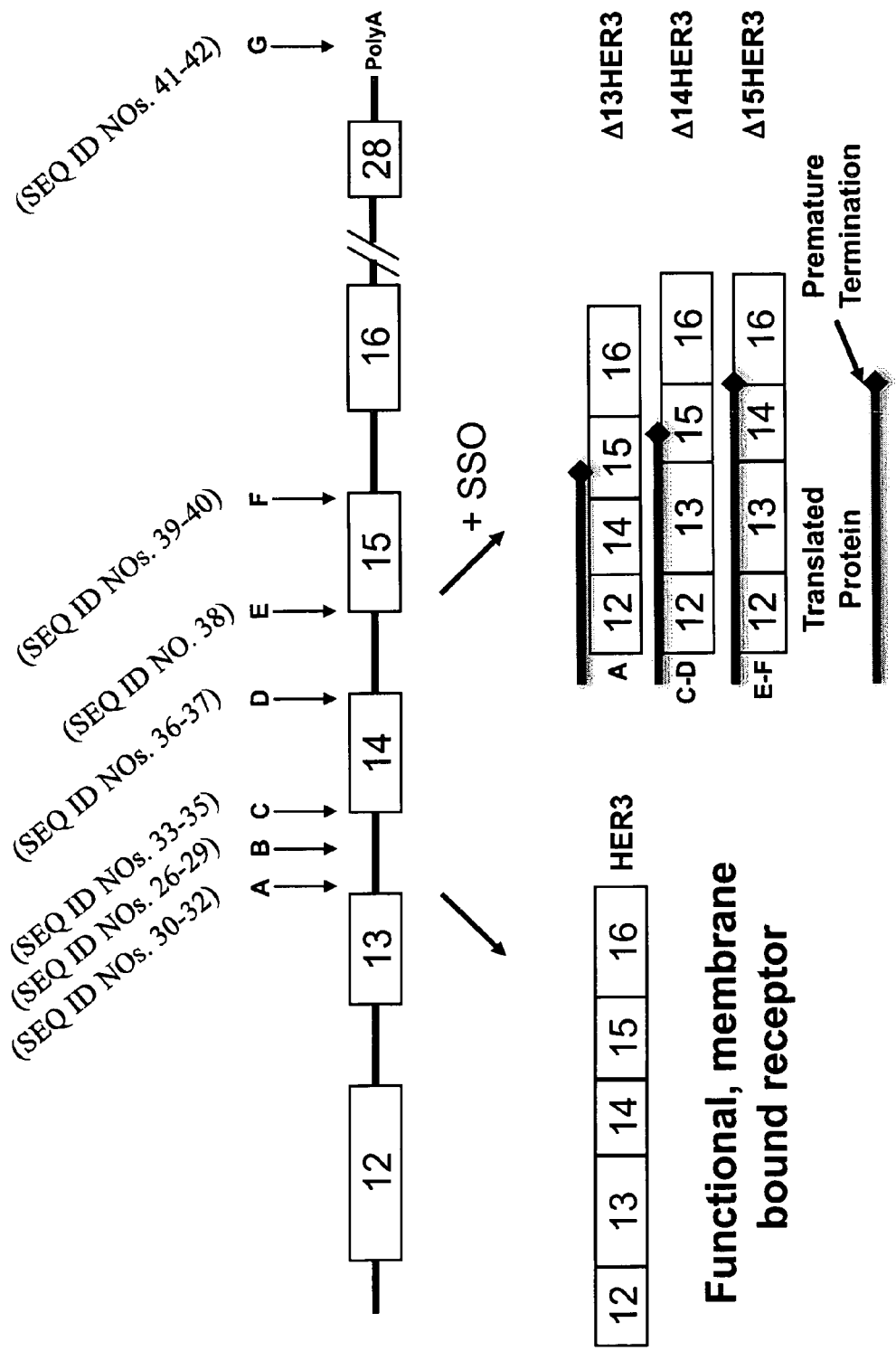
FIG. 7: Oligonucleotides directed toward splicing elements (Arrows) elicit the induction of the indicated novel HER3 mRNAs, such that downstream exons have an improper reading frame, leading to soluble truncated HER3 splice variants that are terminated, as indicated by the arrows over the downstream ends of the soluble receptors.

Exemplary splice switching oligonucleotides (SSOs) containing phosphorothioate internucleotide bonds and targeted to regions of human HER3 pre-mRNA (FIG. 7, Table 3) were synthesized.

TABLE 3

Splice switching Oligonucleotides Targeted to HER3

| SEQ ID. | Name | Sequence (5'-3') | HER3 Target Site | Modification |
|---|---|---|---|---|
| 26 | 1 | GGGTCACTTCCAAGTCCTGA | Putative branch site | 2'-OMe, PS |
| 27 | 2 | GTCACTTCCAAGTCCTGACC | Putative branch site | 2'-OMe, PS |
| 28 | 3 | CACTTCCAAGTCCTGACCTT | Putative branch site | 2'-OMe, PS |
| 29 | 4 | CTTCCAAGTCCTGACCTTCA | Putative branch site | 2'-OMe, PS |
| 30 | 5 | CCCTTACTGTACCCATTCAG | 5' splice site of intron 13 | 2'-OMe, PS |
| 31 | 6 | CTCCCCTTACTGTACCCATT | 5' splice site of intron 13 | 2'-OMe, PS |
| 32 | 7 | TGGCTCCCCTTACTGTACCC | 5' splice site of intron 13 | 2'-OMe, PS |
| 33 | 8 | CTCGAGGCTCCCTGTAGTGG | 3' splice site of intron 13 | 2'-OMe, PS |
| 34 | 9 | ATTCTCGAGGCTCCCTGTAG | 3' splice site of intron 13 | 2'-OMe, PS |
| 35 | 10 | CAAATTCTCGAGGCTCCCTG | 3' splice site of intron 13 | 2'-OMe, PS |
| 36 | 11 | CTAGTATACCGAGCCATTGC | 5' splice site of intron 14 | 2'-OMe, PS |

TABLE 3-continued

Splice switching Oligonucleotides Targeted to HER3

| SEQ ID. | Name | Sequence (5'-3') | HER3 Target Site | Modification |
|---|---|---|---|---|
| 37 | 12 | GTGCTACTAGTATACCGAGC | 5' splice site of intron 14 | 2'-OMe, PS |
| 38 | 13 | CAAGTATCAGAGCCCTGAGT | 3' splice site of intron 14 | 2'-OMe, PS |
| 39 | 14 | TTATCCCATCACTGACCCCT | 5' splice site of intron 15 | 2'-OMe, PS |
| 40 | 15 | TATTATCCCATCACTGACCC | 5' splice site of intron 15 | 2'-OMe, PS |
| 41 | 16 | ATTTCATCTCTTTAAGGCTC | PolyA signal site | 2'-OMe, PS |
| 42 | 17 | CTGGATCTACTGCTTAATTT | PolyA signal site | 2'-OMe, PS |

2'-OMe, 2'-O-methyl oligoribonucleotide; PS, phosphorothioate internucleotide linkage.

Figure 8:
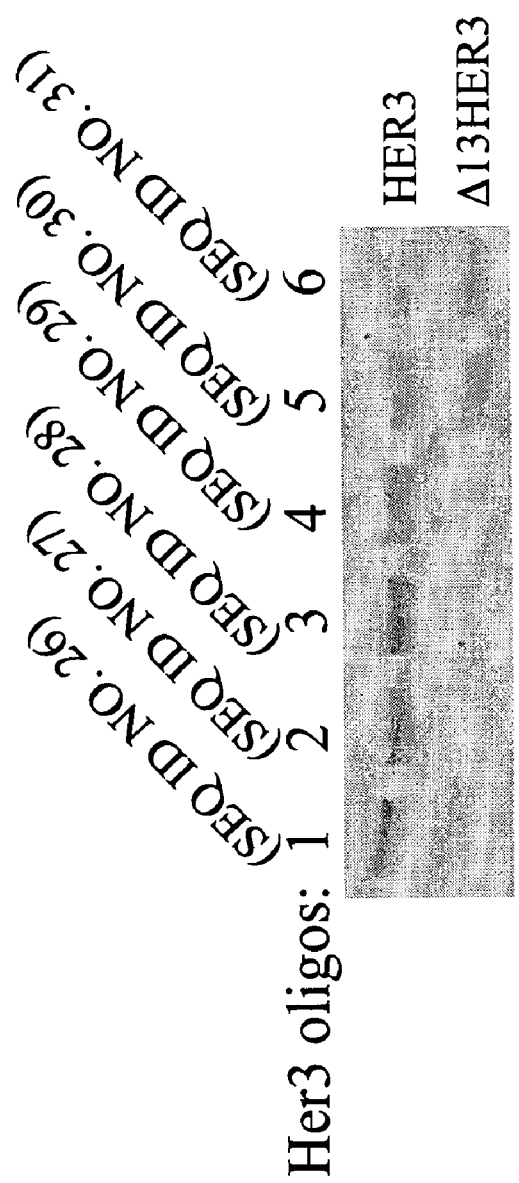
FIG. 8: MCF-7 cells were transfected with 100 nM of the indicated SSO. After 24 hours, total RNA was isolated and RT-PCR was used to amplify a fragment of HER3 mRNA. Full length HER3 transcripts are represented by a 619 bp band (HER3), and transcripts lacking exon 13 are represented by a 486 bp band (Δ13HER3).
Figure 9:
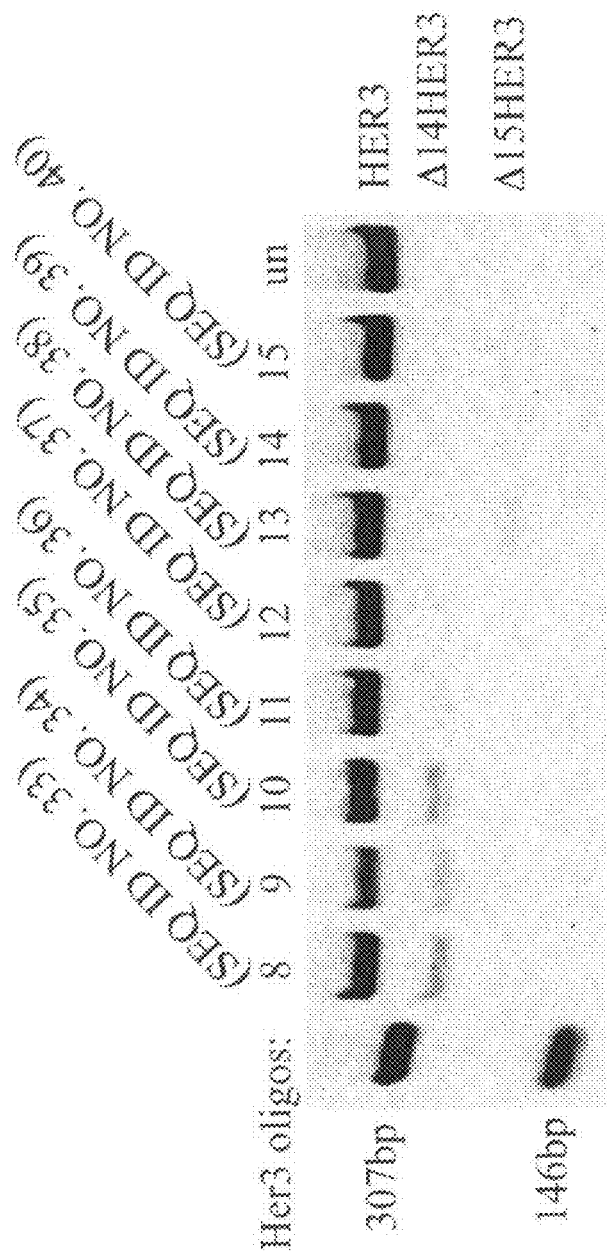
FIG. 9: MCF-7 cells were transfected with the indicated SSO as in FIG. 8. Full length HER3 transcripts are represented by a 353 bp band, and transcripts lacking exon 14 (Δ14HER3) or exon 15 (Δ15HER3) are represented by 262 bp and 198 bp bands, respectively.

These oligonucleotides were transfected into MCF-7 human breast cancer cells with the cationic transfection reagent Lipofectamine™ 2000 (Invitrogen) as per the manufacturer's directions. After 24 hours, the total RNA was collected and RT-PCR was used to determine the ratio of splice variants and full length HER3 mRNA. As shown in FIG. 8 certain SSOs caused skipping of exon 13 (e.g., SSO 5 (SEQ ID NO. 30) and 6 (SEQ ID NO. 31)), leading to reduced levels of HER3 mRNA and increased levels of Δ13HER3 mRNA. As shown in FIG. 9, SSOs 8, 9 and 10 (SEQ ID NOs. 33 thru 35, respectively) all induced Δ14HER3 mRNA, while SSO 13 (SEQ ID NO. 38) induced Δ15HER3 mRNA.

Figure 10:
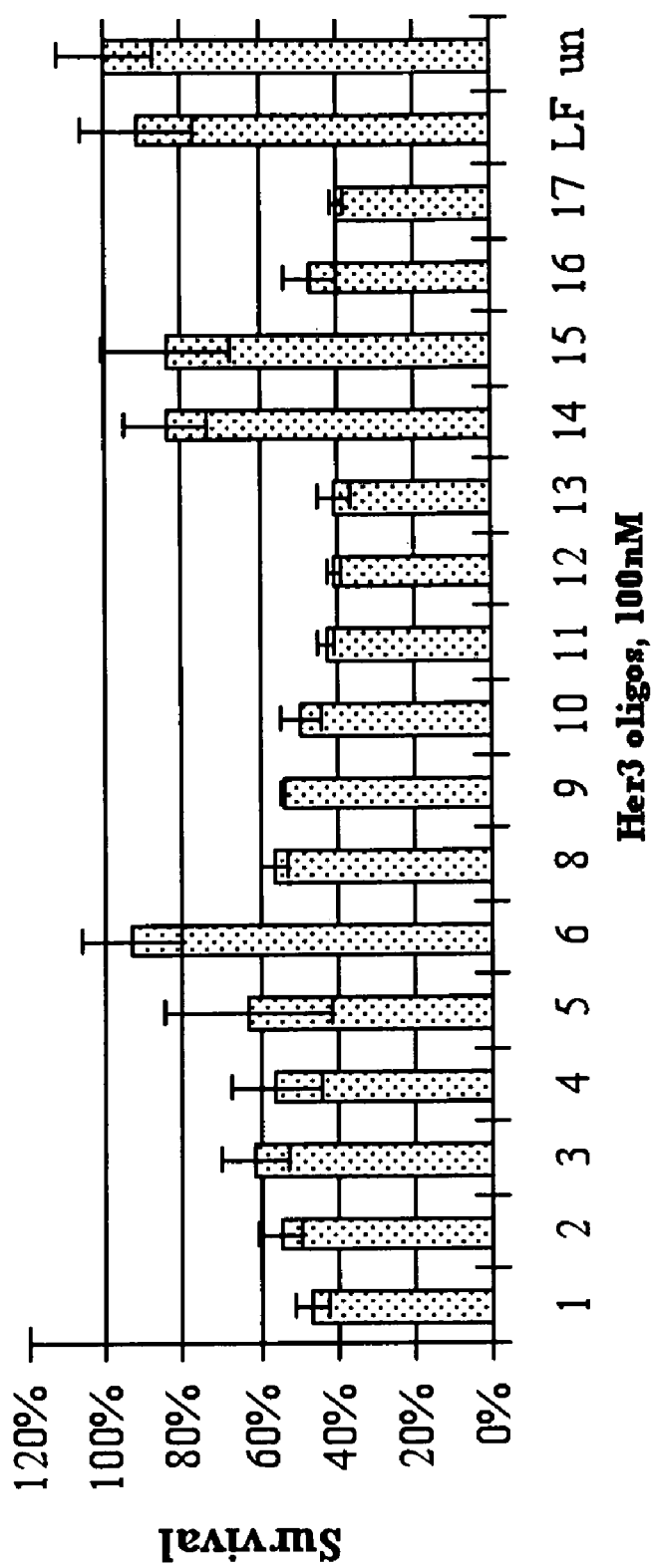
FIG. 10: SK-BR-3 cells were transfected with 100 nM of the indicated SSO as described in the previous figures. After 48 hours, cell viability was measured and expressed as percent of untreated cells.

SK-BR-3 cells were transfected with 100 nM of SSOs 1 thru 17 (SEQ ID NOs. 26 thru 42). After 48 hours, cell viability was measured by the addition of MTS reagent (Promega) (FIG. 10). As shown in FIG. 10, the induction of HER3 splice variants in SK-BR-3 cells by the SSOs, including SSOs 8, 9 and 10 (SEQ ID NOs. 33 thru 35, respectively), all of which induce Δ14HER3 mRNA, caused reduced cell viability compared to mock or untransfected cells.

Example 4

Evaluation of Carrier Peptide Conjugated PMOs in the EGFP-654 Transgenic Mouse

A PMO (654; 5'-GCT ATT ACC TTA ACC CAG-3'; SEQ ID NO: 43) designed to restore correct splicing in the enhanced green fluorescent protein (EGFP) gene was conjugated to various carrier peptides (SEQ ID NOS:44-54) to produce peptide-conjugated PMOs (P-PMOs) and evaluated in vivo for their splice-correction activity and toxicity in the EGFP-654 transgenic mouse model (Sazani, P., F. Gemignani, et al. (2002) Nat Biotechnol 20(12): 1228-33). In this model, the EGFP-654 gene encoding for functional EGFP is interrupted by an aberrantly-spliced mutated intron, and cellular uptake of EGFP-654 targeted P-PMOs can be evaluated by RT-PCR detection of the restored EGFP-654 splice product in tissues.

Female EGFP-654 transgenic mice were injected intraperitoneally once daily for 4 consecutive days with saline or a 12.5 mg/kg dose of P-PMO. Post treatment on day 4, the heart, muscles, liver, kidney, lungs, small intestine, colon, stomach, mammary gland, thymus, spleen, ovary, skin, bone marrow, and brain were harvested, and extracted RNA was evaluated by RT-PCR and densitometry of PCR products for percentage of corrected splice products of the EGFP-654 gene in tissues versus 100% EGFP-654 splice-corrected diaphragm controls.

Figure 14A:
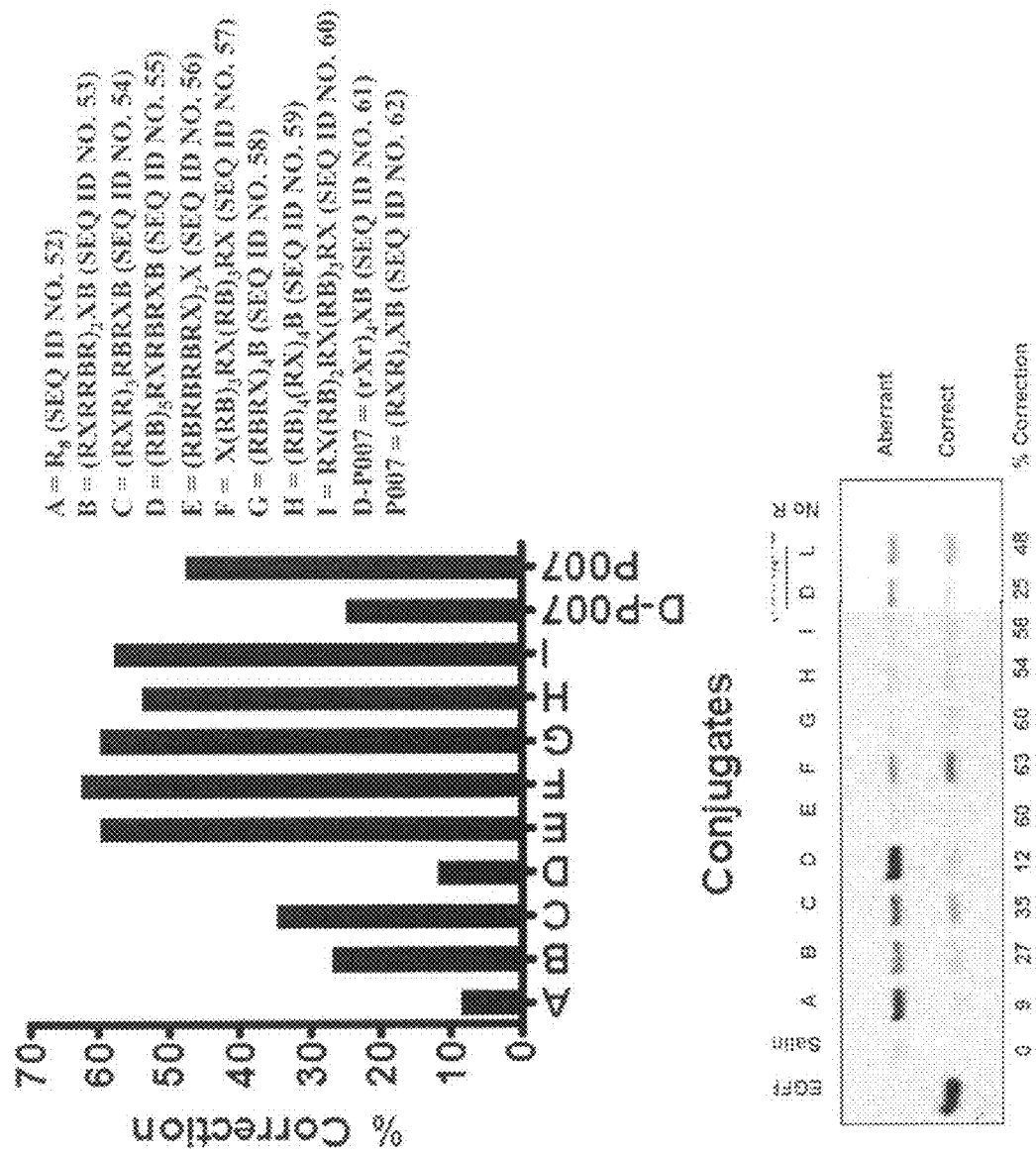
FIG. 14A-B: Splice-correction activity in organs from EGFP-654 transgenic mice treated with various EGFP-654-targeted carrier peptide-PMOs as measured in mammalian gland (FIG. 14A) and ovary and prostate (FIG. 14B).
Figure 14B:
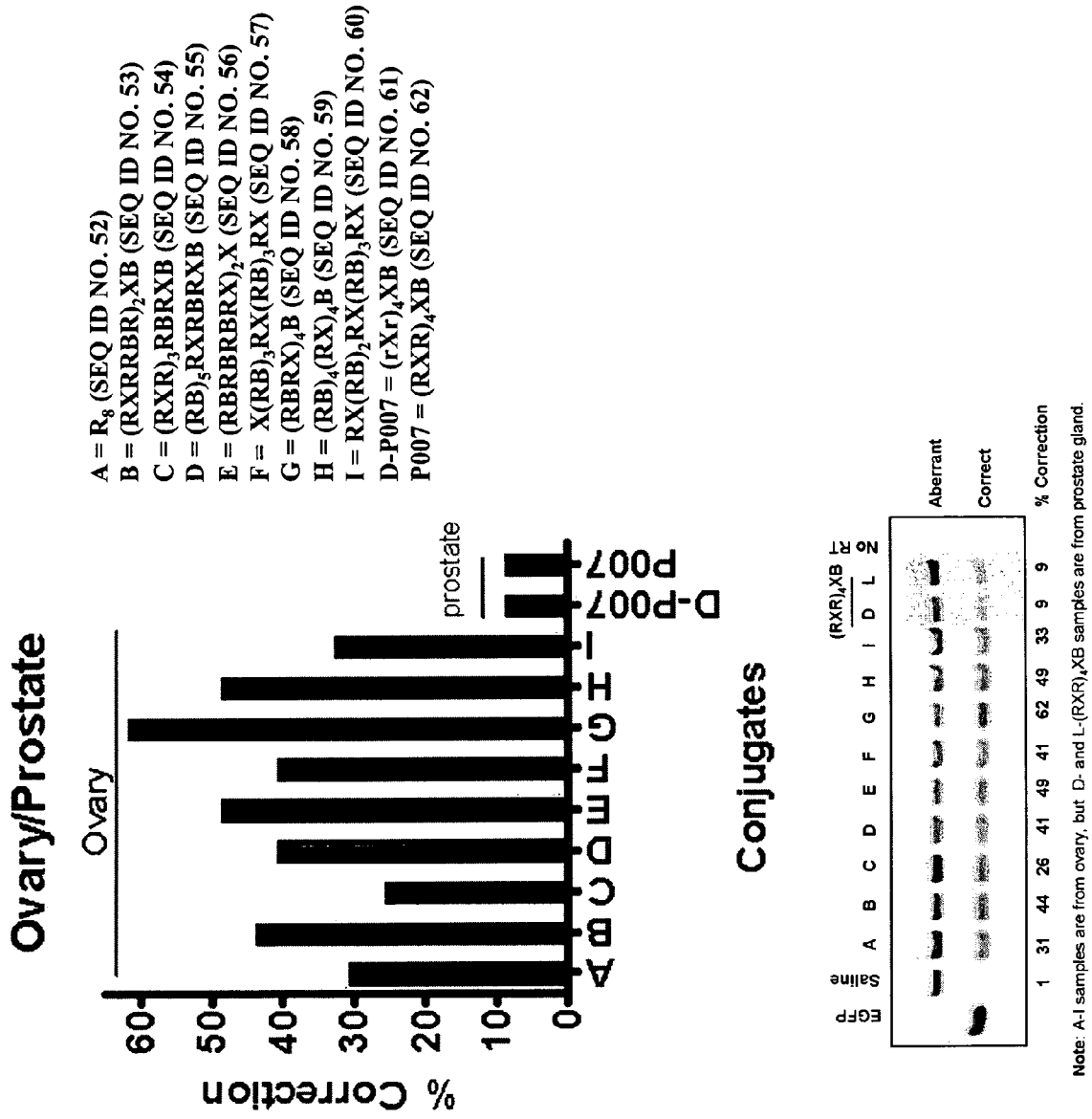

Restoration of functional EGFP splice products post-treatment with various P-PMOs based on RT-PCR analysis of selected tissues including mammary and ovary tissues is shown in FIGS. 14A and 14B. Optimal carrier peptide uptake for mammary (SEQ ID NOS:56-58) and ovary (SEQ ID NO: 58) tissues based on these and similar results is summarized in Table 4 below (indicated by a *). Further examples of tissue-specific peptide delivery of antisense oligonucleotides is described in Sazani, et al, Mol Therapy (2008), in press)

TABLE 4

| Carrier Peptide Uptake in Tissues | | | | | | | | | | | |
|---|---|---|---|---|---|---|---|---|---|---|---|
| Tissue | Optimal Tissue Targeting Peptides: SEQ ID NO. | | | | | | | | | | |
| (%) | 52 | 53 | 54 | 55 | 56 | 57 | 58 | 59 | 60 | 61 | 62 |
| Mammary Gland (≧60%) | | | | | * | * | | | * | | |
| Ovary (>60%) | | | | | | | * | | | | |

It is claimed:

1. An isolated, soluble epidermal growth factor receptor-2 (HER2) protein consisting of the sequence set forth in SEQ ID NO:6 or amino acids 23-584 of SEQ ID NO:6.

2. The protein of claim 1, which is modified by protein pegylation.

3. An isolated nucleic acid encoding an epidermal growth factor receptor-2 (HER2) protein according to claim 1.

4. The nucleic acid of claim 3, consisting of the sequence set forth in SEQ ID NO: 5 or nucleotides 67-1755 of SEQ ID NO:5.

* * * * *

UNITED STATES PATENT AND TRADEMARK OFFICE
CERTIFICATE OF CORRECTION

PATENT NO.         : 7,884,194 B2
APPLICATION NO.    : 12/157094
DATED              : February 8, 2011
INVENTOR(S)        : Ryszard Kole et al.

It is certified that error appears in the above-identified patent and that said Letters Patent is hereby corrected as shown below:

Item 56
"WO WO 02/28875 A3 5/2002" should read, --WO WO 02/28875 A3 4/2002--.

Item 56
"WO WO 03/006475 A3 2/2004" should read, --WO WO 03/006475 A3 1/2003--.

Item 56
"Geary. R.S., et al., "Pharmacokinetics of a tumor necrosis factor-alpha. phosphorothioate 2'-O-(2-methoxyethyl) modified antisense oligonucleotide: comparison across species", *Drug Metabolism and Disposition*, 31(11):1419-1428 (2003)." should read, --Geary. R.S., et al., "Pharmacokinetics of a tumor necrosis factor-alpha phosphorothioate 2'-O-(2-methoxyethyl) modified antisense oligonucleotide: comparison across species", *Drug Metabolism and Disposition,* 31(11):1419-1428 (2003).--.

Item 56
"Slamon, D., et al., "Studies of the HER-2/neu proto-oncogene in human breast and ovarian cancer", *Science*, 244(4905):707-712 1989." should read, --Slamon, D., et al., "Studies of the HER-2/neu proto-oncogene in human breast and ovarian cancer", *Science*, 244(4905)707-712 (1989).--.

Item 56
"Slamon, D., et al., "Use of chemotherapy plus a monoclonal antibody against HER2 for metastatic breast cancer that overexpresses HER2", *N. Engl. J. Med.* 344(11):783-792 2001." should read, --Slamon, D., et al., "Use of chemotherapy plus a monoclonal antibody against HER2 for metastatic breast cancer that overexpresses HER2", *N. Engl. J. Med.* 344(11):783-792 (2001).--.

Column 113
Claim 1, Line 57, "(HER2) protein consisting of the sequence set forth in SEQ" should read --(HER2) protein, consisting of the sequence set forth in SEQ--.

Signed and Sealed this
Twenty-first Day of June, 2011

David J. Kappos
*Director of the United States Patent and Trademark Office*